(12) United States Patent
Goldberg et al.

(10) Patent No.: US 9,050,163 B2
(45) Date of Patent: Jun. 9, 2015

(54) URETHRAL ANASTOMOSIS DEVICE AND METHOD

(75) Inventors: Roger P. Goldberg, Evanston, IL (US); Douglas S. Scherr, Scarsdale, NY (US); Anthony J. Wirtel, III, Malvern, PA (US); Rahul S. Nair, Kerala (IN); Nikhil R. Katre, Maharashtra (IN); Debasish Pradhan, Orissa (IN); Athar Solkar, Maharashtra (IN); Salman Kapadia, Madhya Pradesh (IN); Arvind K. Gupta, Uttar Pradesh (IN); Dinesh A. Diwakar, Mumbai (IN); Rajesh T. Shelke, Bangalore (IN); Jithin Ambujan, Maharashtra (IN)

(73) Assignee: Endo Pharmaceuticals Inc., Chadds Ford, PA (US)

( * ) Notice: Subject to any disclaimer, the term of this patent is extended or adjusted under 35 U.S.C. 154(b) by 336 days.

(21) Appl. No.: 13/425,059

(22) Filed: Mar. 20, 2012

(65) Prior Publication Data

US 2012/0245606 A1  Sep. 27, 2012

Related U.S. Application Data

(60) Provisional application No. 61/454,805, filed on Mar. 21, 2011.

(51) Int. Cl.
*A61B 17/08* (2006.01)
*A61F 2/00* (2006.01)
(Continued)

(52) U.S. Cl.
CPC ....... *A61F 2/0022* (2013.01); *A61B 2017/1107* (2013.01); *A61B 17/00491* (2013.01);
(Continued)

(58) Field of Classification Search
CPC ........... A61B 17/11; A61B 2017/1107; A61B 2017/0403; A61B 2017/0408; A61B 2017/0464; A61B 2017/06176; A61B 2017/0641; A61B 2017/0647; A61B 2017/1135; A61B 17/00491; A61B 17/0643; A61F 2/0022; A61F 2/0036; A61F 2/064; A61F 2/95; A61F 2002/047; A61F 2002/048; A61F 2002/9505; A61F 2002/9517
USPC .......................... 606/153–156, 151, 213, 215
See application file for complete search history.

(56) References Cited

U.S. PATENT DOCUMENTS 4,157,378 A  6/1979  Tomlinson et al.
4,233,981 A  11/1980  Schomacher
(Continued)

FOREIGN PATENT DOCUMENTS

JP  08-019597  1/1996
WO  99/17662  4/1999
(Continued)

OTHER PUBLICATIONS

Obora, Yoshiro, Nonsuture Microvascular Anastomosis Using Magnet Rings, 1980, Neural Med Chir, 20, 497-505.*
(Continued)

*Primary Examiner* — Julian W Woo
*Assistant Examiner* — Lucas Paez
(74) *Attorney, Agent, or Firm* — DLA Piper LLP (US)

(57) ABSTRACT

Provided herein is a two-part coupling assembly for re-connecting a first hollow body part to a second body part and an instrument and method for emplacement. The coupling assembly comprises coupling parts having securement elements that are actuated by separate deployment mechanisms of the instrument and attach to the first and second body parts. The first and second coupling parts having interconnecting elements that couple the two-part assembly together and re-connect the first and second body parts.

21 Claims, 72 Drawing Sheets

(51) Int. Cl.
  *A61F 2/06* (2013.01)
  *A61B 17/11* (2006.01)
  *A61B 17/00* (2006.01)
  *A61B 17/064* (2006.01)
  *A61B 17/04* (2006.01)
  *A61B 17/06* (2006.01)
  *A61F 2/04* (2013.01)
  *A61F 2/95* (2013.01)

(52) U.S. Cl.
  CPC ............. *A61B17/0643* (2013.01); *A61B 17/11* (2013.01); *A61B 2017/0403* (2013.01); *A61B 2017/0408* (2013.01); *A61B 2017/0464* (2013.01); *A61B 2017/06176* (2013.01); *A61B 2017/0641* (2013.01); *A61B 2017/0647* (2013.01); *A61B 2017/1135* (2013.01); *A61F 2/0036* (2013.01); *A61F 2002/047* (2013.01); *A61F 2002/048* (2013.01); *A61F 2002/9505* (2013.01); *A61F 2002/9517* (2013.01); *A61F 2/064* (2013.01); *A61F 2/95* (2013.01)

(56) References Cited

U.S. PATENT DOCUMENTS

| | | | |
|---|---|---|---|
| 4,429,691 A | 2/1984 | Niwa et al. | |
| 4,612,053 A | 9/1986 | Brown et al. | |
| 4,684,673 A | 8/1987 | Adachi | |
| 4,737,411 A | 4/1988 | Graves, Jr. et al. | |
| 4,849,193 A | 7/1989 | Palmer et al. | |
| 4,880,610 A | 11/1989 | Constantz | |
| RE33,161 E | 2/1990 | Brown et al. | |
| 4,917,702 A | 4/1990 | Scheicher et al. | |
| RE33,221 E | 5/1990 | Brown et al. | |
| 4,938,938 A | 7/1990 | Ewers et al. | |
| 4,959,104 A | 9/1990 | Iino et al. | |
| 4,976,715 A | 12/1990 | Bays et al. | |
| 5,034,059 A | 7/1991 | Constantz | |
| 5,037,639 A | 8/1991 | Tung | |
| 5,047,031 A | 9/1991 | Constantz | |
| 5,053,212 A | 10/1991 | Constantz et al. | |
| 5,085,861 A | 2/1992 | Gerhart et al. | |
| 5,129,905 A | 7/1992 | Constantz | |
| 5,149,368 A | 9/1992 | Liu et al. | |
| 5,152,836 A | 10/1992 | Hirano et al. | |
| 5,164,187 A | 11/1992 | Constantz et al. | |
| 5,178,845 A | 1/1993 | Constantz et al. | |
| 5,262,166 A | 11/1993 | Liu et al. | |
| 5,273,964 A | 12/1993 | Lemons | |
| 5,279,831 A | 1/1994 | Constantz et al. | |
| 5,281,265 A | 1/1994 | Liu | |
| 5,286,763 A | 2/1994 | Gerhart et al. | |
| 5,322,501 A | 6/1994 | Mahmud-Durrani | |
| 5,336,233 A | 8/1994 | Chen | |
| 5,336,264 A | 8/1994 | Constanz et al. | |
| 5,350,104 A | 9/1994 | Main et al. | |
| 5,427,754 A | 6/1995 | Nagata et al. | |
| 5,432,395 A | 7/1995 | Grahn | |
| 5,456,714 A | 10/1995 | Owen | |
| 5,470,803 A | 11/1995 | Bonfield et al. | |
| 5,496,399 A | 3/1996 | Ison et al. | |
| 5,516,532 A | 5/1996 | Atala et al. | |
| 5,522,893 A | 6/1996 | Chow et al. | |
| 5,525,148 A | 6/1996 | Chow et al. | |
| 5,542,973 A | 8/1996 | Chow et al. | |
| 5,545,254 A | 8/1996 | Chow et al. | |
| 5,562,895 A | 10/1996 | Tung | |
| 5,565,502 A | 10/1996 | Glimcher et al. | |
| 5,605,713 A | 2/1997 | Boltong | |
| 5,650,176 A | 7/1997 | Lee et al. | |
| 5,658,593 A | 8/1997 | Orly et al. | |
| 5,665,120 A | 9/1997 | Ohtsuka et al. | |
| 5,691,397 A | 11/1997 | Glimcher et al. | |
| 5,700,289 A | 12/1997 | Breitbart et al. | |
| 5,782,971 A | 7/1998 | Constantz | |
| 5,797,934 A | 8/1998 | Rygaard | |
| 5,846,312 A | 12/1998 | Ison et al. | |
| 5,904,697 A | 5/1999 | Gifford, III et al. | |
| 5,931,842 A | 8/1999 | Goldsteen et al. | |
| 6,117,148 A | 9/2000 | Ravo et al. | |
| 6,371,965 B2 | 4/2002 | Gifford, III et al. | |
| 6,428,550 B1 | 8/2002 | Vargas et al. | |
| 6,461,367 B1 * | 10/2002 | Kirsch et al. | 606/144 |
| 6,503,259 B2 | 1/2003 | Huxel et al. | |
| 6,506,190 B1 | 1/2003 | Walshe | |
| 6,524,322 B1 | 2/2003 | Berreklouw | |
| 6,666,873 B1 * | 12/2003 | Cassell | 606/153 |
| 6,726,694 B2 | 4/2004 | Blatter et al. | |
| 6,736,824 B2 | 5/2004 | Borghi | |
| 6,752,938 B2 | 6/2004 | Wang et al. | |
| 6,776,785 B1 * | 8/2004 | Yencho et al. | 606/153 |
| 7,112,211 B2 | 9/2006 | Gifford, III et al. | |
| 7,182,771 B1 | 2/2007 | Houser et al. | |
| 7,452,363 B2 | 11/2008 | Ortiz | |
| 7,527,185 B2 | 5/2009 | Harari et al. | |
| 7,553,317 B2 | 6/2009 | Weisenburgh, II et al. | |
| 7,559,938 B2 | 7/2009 | Hess et al. | |
| 7,666,197 B2 * | 2/2010 | Orban, III | 606/153 |
| 7,691,113 B2 | 4/2010 | Ortiz et al. | |
| 7,771,443 B2 * | 8/2010 | Copa et al. | 606/153 |
| 7,824,421 B2 | 11/2010 | Weisenburgh, II et al. | |
| 7,871,418 B2 | 1/2011 | Thompson et al. | |
| 7,901,417 B2 | 3/2011 | Blatter et al. | |
| 8,048,443 B2 | 11/2011 | Benedict et al. | |
| 8,048,857 B2 | 11/2011 | McKay et al. | |
| 2002/0091397 A1 | 7/2002 | Chen | |
| 2004/0230209 A1 | 11/2004 | Masroor | |
| 2005/0021085 A1 | 1/2005 | Abrams et al. | |
| 2005/0165426 A1 | 7/2005 | Manzo | |
| 2006/0217748 A1 | 9/2006 | Ortiz | |
| 2008/0114385 A1 | 5/2008 | Byrum et al. | |
| 2009/0302089 A1 | 12/2009 | Harari et al. | |
| 2010/0082049 A1 | 4/2010 | Orban | |
| 2010/0114129 A1 | 5/2010 | Wheatley et al. | |
| 2010/0130993 A1 | 5/2010 | Paz et al. | |
| 2010/0137999 A1 | 6/2010 | Shohat | |
| 2010/0318109 A1 | 12/2010 | Granja Filho | |

FOREIGN PATENT DOCUMENTS

| | | |
|---|---|---|
| WO | 00/27312 | 5/2000 |
| WO | 2004/000093 | 12/2003 |
| WO | 2008/135083 | 11/2008 |
| WO | 2009/046998 | 4/2009 |

OTHER PUBLICATIONS

Biomaterials Science: An Introduction to Materials Medicine 64-73 (Buddy D. Ratner ed., Academic Press, Ltd., 1996).
International Search Report dated Jun. 18, 2012.

* cited by examiner

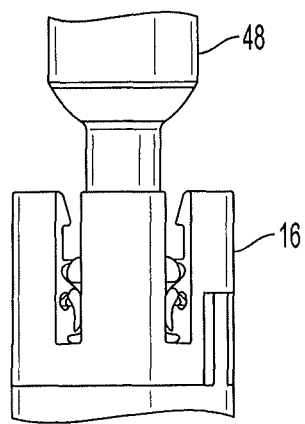
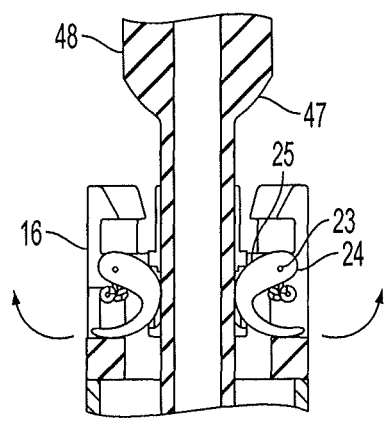
FIG. 24        FIG. 25
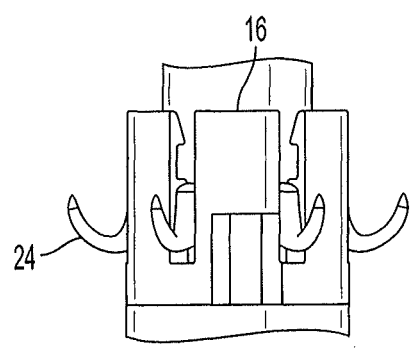
FIG. 26

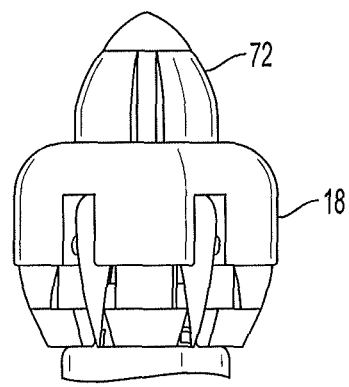
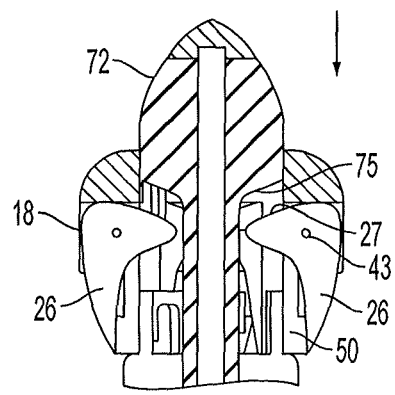
FIG. 29    FIG. 30
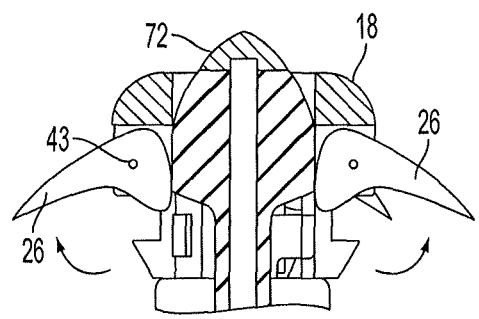
FIG. 31

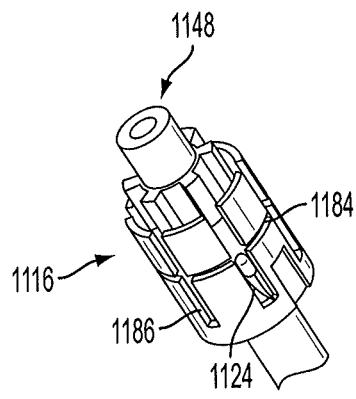
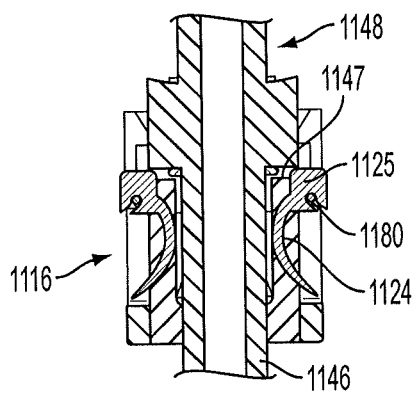
FIG. 67A  FIG. 67B
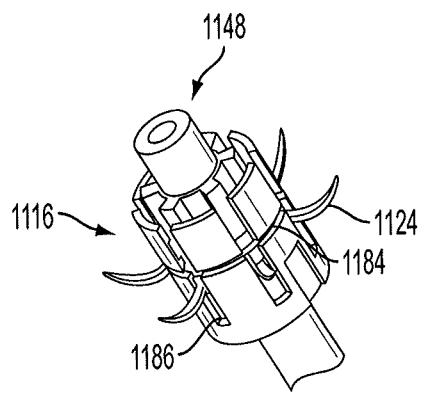
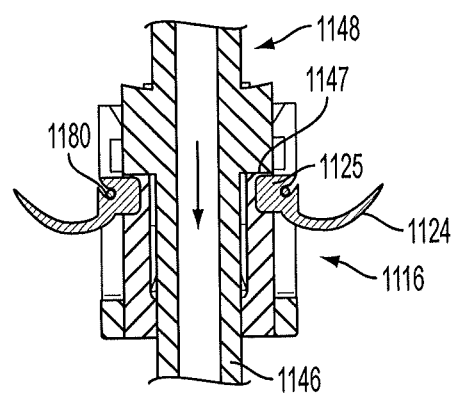
FIG. 68A  FIG. 68B

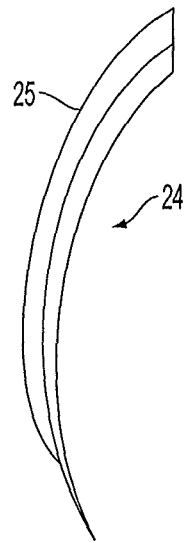
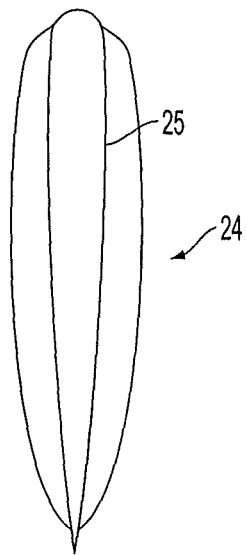
FIG. 83A　　　　　　　　　FIG. 83B
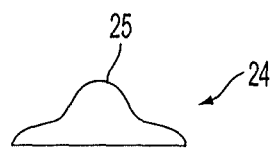
FIG. 83C

URETHRAL ANASTOMOSIS DEVICE AND METHOD

CROSS REFERENCE TO RELATED APPLICATIONS

This application claims to the benefit of U.S. Provisional Patent Application No. 61/454,805, filed Mar. 21, 2011, the entire contents of which are incorporated by reference, as if fully set forth herein.

TECHNICAL FIELD

This disclosure relates generally to the field of medical devices and, in particular, to devices and methods for reconnecting two hollow body parts such as a urethra to a bladder.

BACKGROUND

The prostate gland is a semen-producing organ located in the abdomen of males. Cancer of the prostate gland is an extremely common ailment among older American men. In fact, prostate cancer is the second-leading cause of cancer-related deaths and the most common cancer diagnosed in men. In 2010, an estimated 90,000 American men underwent radical prostatectomy, a surgery in which their prostate gland was removed. If past experience holds, nearly one-third of these men suffered complications, which at the least were painful and at most required further invasive surgery.

The most common complication, known as bladder-neck contracture, is caused by leakage of urine into the abdomen. During a radical prostatectomy, after the prostate is removed, it is necessary to re-attach the bladder (where the body stores urine) to the urethra (the passage carrying urine from the bladder to the penis). Unfortunately, the conventional hand-sewn five- to six-suture re-attachment (an anastomosis) often does not result in a leak-proof seal. Consequently, urine can leak from the bladder into the abdomen until the anastomosis is sealed, which can take up to five days. Such leakage causes scarring, which in turn leads to bladder-neck contractures. A patient suffering from such a contracture typically is unable to urinate and requires painful and expensive intervention.

In addition, with the robotic approach, the urethral vesicle anastamosis can be one of the most challenging components of the surgery. In the most-experienced hands, this can add thirty minutes to the operation, and in the hands of a novice, it can add one hour to the operation.

Accordingly, it can be seen that needs exist for improved ways to re-attach the urethra to the bladder. It is to this and other solutions that the embodiments of the present invention are primarily directed.

SUMMARY

We provide an instrument for re-connecting a first hollow body part to a second body part with a two-part coupling assembly, the two coupling parts each having securement elements. The instrument comprises a handle assembly, at least two elongate coaxial members longitudinally slidable with respect to each other, deployment mechanisms for deploying the securement elements of the coupling parts, and at least one release mechanism for releasing the two-part coupling assembly from the elongate members.

We also provide a two-part coupling assembly for re-connecting a first hollow body part to a second body part. The coupling assembly comprises coupling parts having securement elements that are actuated by separate deployment mechanisms and attach to the first and second body parts. The first and second coupling parts have interconnecting elements that couple the two-part assembly together and re-connect the first and second body parts.

We also provide a method of connecting a first hollow body part to a second hollow body part comprising inserting a first coupling into the first hollow body part and deploying the securement elements of the first coupling to secure the first coupling in place. Subsequently, the second coupling part is extended into the second hollow body part and the securement elements of the second coupling are deployed to secure the second coupling part in place. The second coupling is then retracted into an interconnecting relationship with the first coupling and the first and second coupling parts are released from the instrument.

BRIEF DESCRIPTION OF THE DRAWINGS

FIG. 24 is a side view of an exemplary embodiment of a lower ring in place on a handle tube.

FIG. 25 is cross-sectional view of the lower ring depicted in FIG. 24, shown with the securement elements in the retracted position.

FIG. 26 is a side view of an exemplary embodiment of the lower ring depicted in FIG. 24, shown with the securement elements in the deployed position.

FIG. 29 is a side view of an exemplary embodiment of an upper ring in place on a deployer element.

FIG. 30 is cross-sectional view of the upper ring depicted in FIG. 29, shown with the securement elements in the retracted position.

FIG. 31 is a cross-sectional view of the upper ring depicted in FIG. 29, shown with the securement elements in the deployed position.

FIG. 67A is a perspective view of a further alternative exemplary embodiment of an anastomosis device showing a lower coupling part with securement elements in the undeployed position and a lower ring securement element deployer.

FIG. 67B is a cross sectional view of the embodiment of the anastomosis device depicted in FIG. 67A.

FIG. 68A is a perspective view of the anastomosis device depicted in FIG. 67A with securement elements in the deployed position and a lower ring securement element deployer.

FIG. 68B is a cross sectional view of the anastomosis device depicted in FIG. 68A.

FIG. 83A is a side view of a further alternative embodiment of a securement element for use in an anastomosis device.

FIG. 83A is a top view of the securement element depicted in FIG. 83A.

FIG. 83C is a cross sectional view of the securement element depicted in FIG. 83A.

FIG. 101D is a side view of the bladder neck and urethra neck of a patient at twelve weeks post-implantation of the ring assembly of the anastomosis system depicted in FIG. 100.

DETAILED DESCRIPTION

Figure 1:
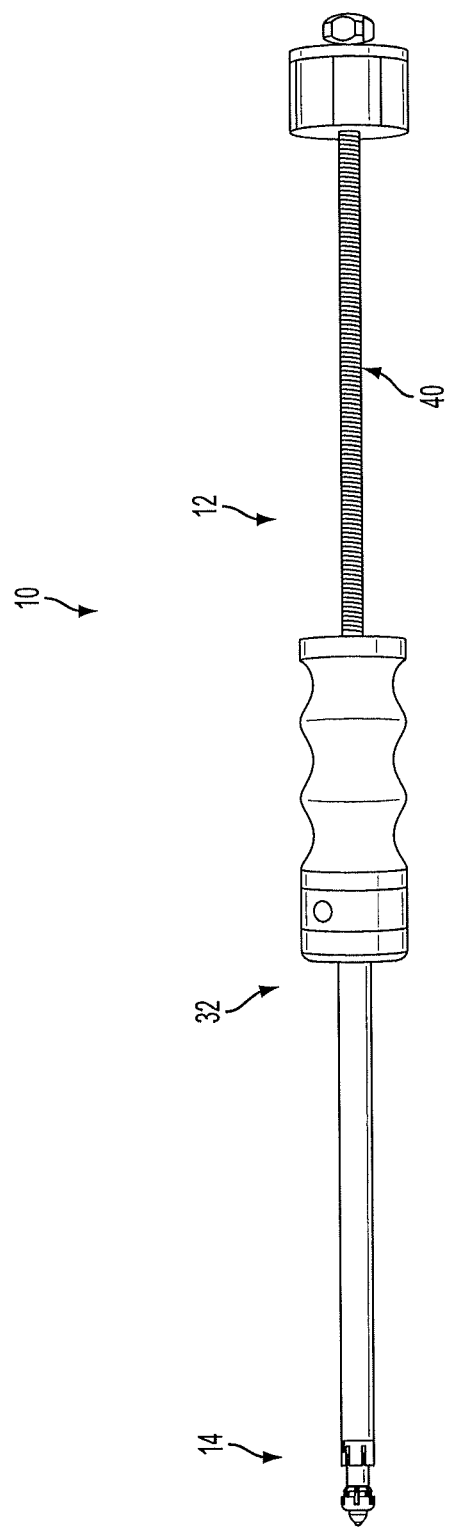
FIG. 1 is a side view of an exemplary embodiment of an assembled anastomosis system.

The present disclosure generally relates to anastomosis systems and methods. In the depicted embodiments, the systems and methods relate to urethral anastomosis systems and methods. Persons of ordinary skill in the art will appreciate that the teachings herein can be readily adapted to other types of anastomosis systems and methods. Accordingly, as used herein, the terms such as urethra and bladder are not intended to be limiting of the embodiments of the present invention. Instead, it will be understood that the embodiments of the present invention relate generally to the field of medical devices and, in particular to devices and methods for reconnecting two hollow body parts or vessels, such as the urethra and the bladder, or two portions of any other body vessel. As used herein, the terms "proximal" and "distal" refer respectively to the directions closer to and further from the operator of the anastomosis device. For purposes of clarity, the distal portion of the device is inserted furthest into an anastomosis patient and the proximal portion of the device remains at least partly outside of the patient. Likewise, the term "lower" is generally used to refer to a portion of the device that is proximally located with respect to a corresponding portion of the device. The term "upper" is generally used to refer to a portion of the device that is distally located with respect to a corresponding portion of the device.

The anastomosis systems of the present disclosure generally include a coupling assembly for connecting and sealing the two body parts and a surgical implement for emplacing the coupling assembly. In typical embodiments, the couplings each include two rings, each ring with securement elements that attach to the respective body part and each ring with interconnecting elements that attach to each other. For example, in some of the depicted embodiments for urethral anastomosis, the couplings include two rings each made of a degradable/absorbable material and interconnected to form a leak-proof seal between the bladder and the urethra. The coupling assembly, which may also be referred to as a ring assembly herein, eliminates urine leakage, removing the cause of the most common post-operative complication, bladder-neck contracture. Also, the anastomosis is performed entirely within the urethra and thus there is no risk of damaging the neurovascular bundles that lie directly outside the urethra.

In addition, the surgical instrument of the anastomosis system can be used laparoscopically/robotically as well. Currently, a laparoscopic/robotic prostatectomy requires a hand-sewn urethral anastomosis that can take up to three hours and does not result in an immediate water-tight seal. There has been an enormous increase in robotic-assisted radical prostatectomies during the last five years. This surgical instrument can be used with the coupling assembly to form a seal between the bladder and the urethra in only approximately fifteen minutes (rather than three hours) and the resulting seal is leak-proof. This system and method also presents the potential to perform the procedure without a urethral catheter, which is normally left in place for seven to ten days. Finally, the system and method will only compromise about 4 mm of urethra, thereby maximizing "functional urethral length," which is known to be one of the most important determinants of post-operative continence.

In the figures, in which like numerals indicate like elements throughout, there is shown an embodiment of an anastomosis system. The first embodiment of the anastomosis system is generally referred to by the numeral 10.

Turning now to the drawings, FIG. 1 shows an anastomosis system 10, including a surgical instrument 12 and a ring coupling assembly 14, according to a first exemplary embodiment of the present invention. The anastomosis system 10 is designed for connecting and sealing a bladder to a urethra, but can be adapted for connecting other hollow body parts.

Referring generally to FIGS. 2-5, the ring coupling assembly 14 includes a lower (or first or urethra) ring 16 and an upper (or second or bladder) ring 18, each defining an internal coaxial lumen. The lower ring 16 has securement elements 24 that are pivotable on pivot pin 23 (see FIG. 25) between a stored/retracted/delivery position in which they are recessed into the lower ring body and a deployed/extended position in which they extend outward from the lower ring body so that they engage and secure to the wall of the urethra or other hollow body part. The lower ring securement elements 24 have cam surfaces 25 (see FIG. 25) on the inner facing surfaces that extend within the lumen of the lower ring 16. Similarly, the upper ring 18 has securement elements 26 that are pivotable on pivot pin 43 (see FIG. 31) between a stored/retracted/delivery position in which they are recessed into the upper ring body and a deployed/extended position in which they extend outward from the upper ring body so that they engage and secure to the wall of the bladder. The upper ring securement elements 26 have cam surfaces 27 (see FIG. 30) on the inner facing surfaces that extend within the lumen of the upper ring 18. In typical embodiments, the lower securement elements 24 pivot downward less than 90 degrees from the stored to the deployed position, and the upper securement elements 26 pivot upward less than 90 degrees from the stored to the deployed position, such that, in the deployed position, the securement elements are oriented towards each other in order to engage the walls of the urethra and the bladder to maintain a compression fit between the urethra and the bladder for good sealing.

As shown, the upper and lower rings 18, 16 of the ring coupling assembly 14 define a central lumen that permits the passage of fluid therethrough. The ring assembly 14 has a generally circular cross-section; however, other shapes are possible, including octagonal or hexagonal cross-sectional shapes. In some embodiments for anastomosis of a bladder and urethra, the upper ring 18 may have an outer diameter of approximately 9.0 mm, an inner diameter defining a lumen of approximately 5.0 mm, and a height of approximately 8.0 mm and the lower ring 16 may have an outer diameter of approximately 9.0 mm, an inner diameter defining a lumen of approximately 6.0 mm, and a height of approximately 8.5 mm. However, larger or smaller dimensions are possible so long as the ring assembly (i) can be received within and securely engage to the hollow body parts being joined together by anastomosis and (ii) provides a lumen that permits the passage of fluid therethrough.

Figure 3:
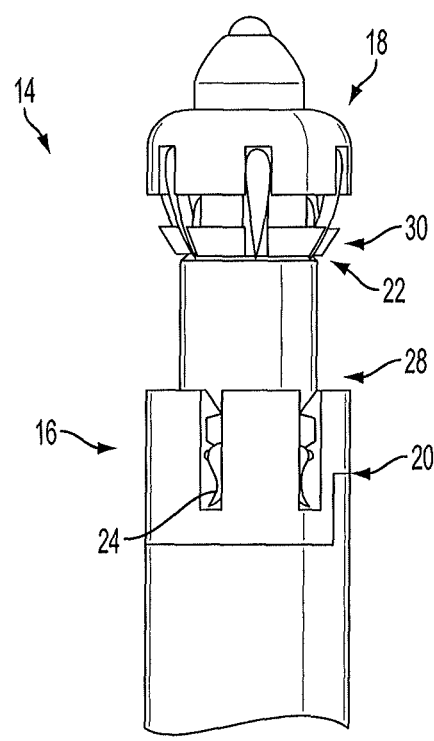
FIG. 3 is a side view of a portion of the anastomosis system depicted in FIG. 1 showing a two-part coupling assembly with securement elements in the retracted position.
Figure 4:
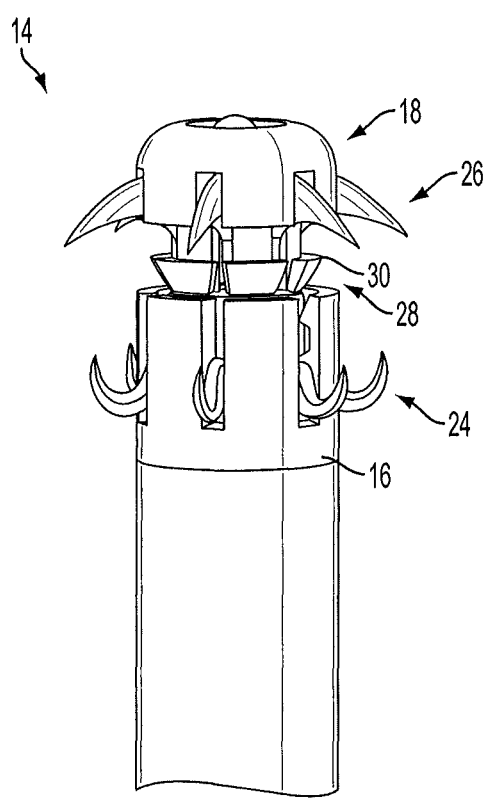
FIG. 4 is a side view of the two-part coupling assembly of FIG. 3, with the securement elements in the deployed position.
Figure 5:
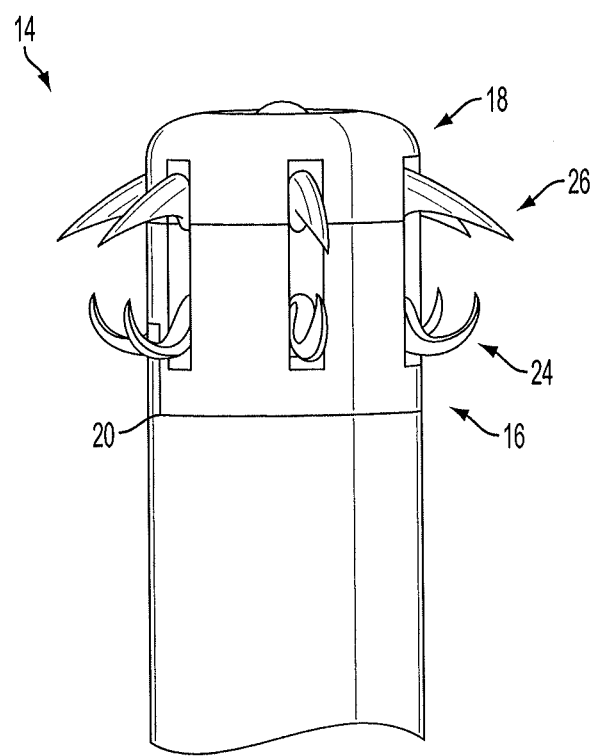
FIG. 5 is a side view of the two-part coupling assembly of FIG. 3, with securement elements in the deployed position and the upper and lower rings coupled together.
Figure 7:
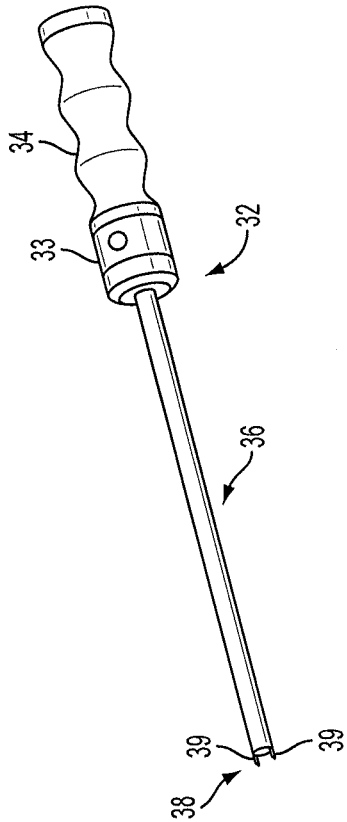
FIG. 7 is a perspective view of a portion of the anastomosis system depicted in FIG. 1 showing a handle assembly.

Referring specifically to FIGS. 3 and 4, the interconnector elements 28 and 30 of the rings 16 and 18, respectively, can be provided by snap-fit connectors, screw-together connectors, or other conventional connector assemblies, whether detachable for decoupling or intended for one-time connection only. In typical embodiments, the snap- or press—fit connector elements 28 and 30 are provided by resiliently deflectable arms 31 with releasably interlocking catch surfaces (as depicted in FIGS. 35-38), detents, push-pin assemblies, or other types of connectors for coupling two parts together. Additional details of examples of the interconnecting (by interconnector elements 28 and 30) of the rings 16 and 18, and of their mounting to the surgical instrument 12 (by ring-mounting connectors 20 and 22), are provided in the further description of the operation of the system 10 below.

Figure 6:
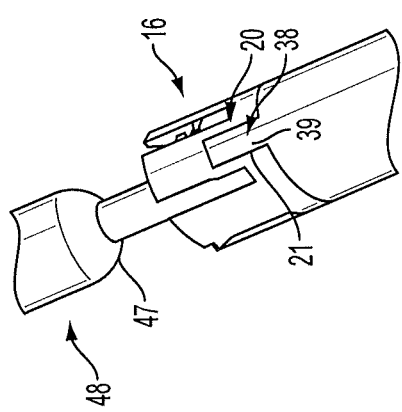
FIG. 6 is a perspective view of a portion of the anastomosis system depicted in FIG. 1 showing a lower coupling part mounted on the distal end of a handle tube.

Referring now to FIGS. 1, 2, 7, 8, 13A, 14, and 16, the surgical instrument 12 includes a handle assembly 32, an intermediate applicator assembly 40, and an inner applicator assembly 64. The handle assembly 32 includes a hollow grip member 34 and a hollow elongate handle tube 36 extending distally from the grip member 34, which together define an internal handle lumen 37 (see FIG. 8). The grip member 34 includes a lock ring 33 with a lock button 77 and has inner screw threads 35 (see FIGS. 8 and 39-42), as described in detail below. The handle tube 36 includes at least one ring-mounting connector 38 that mounts to the at least one ring-mounting connector 20 of the lower ring 16 (see FIGS. 5 and 6). For example, in the depicted embodiment, the handle tube ring-mounting connector 38 is provided by two strip projections 39 extending from the distal end of the handle tube 36 and the lower ring ring-mounting connector 20 is provided by two recesses 21 adapted to releasably receive the projections with a friction fit (see FIGS. 6 and 7). A detent can be included on either of the strip projections 29 or within the recess 21 to help hold the lower ring 16 on the handle tube 36, so long as the axial force needed to overcome the detent forces and detach the parts does not interfere with intended detachment of the lower ring 16 during operation.

Figure 2:
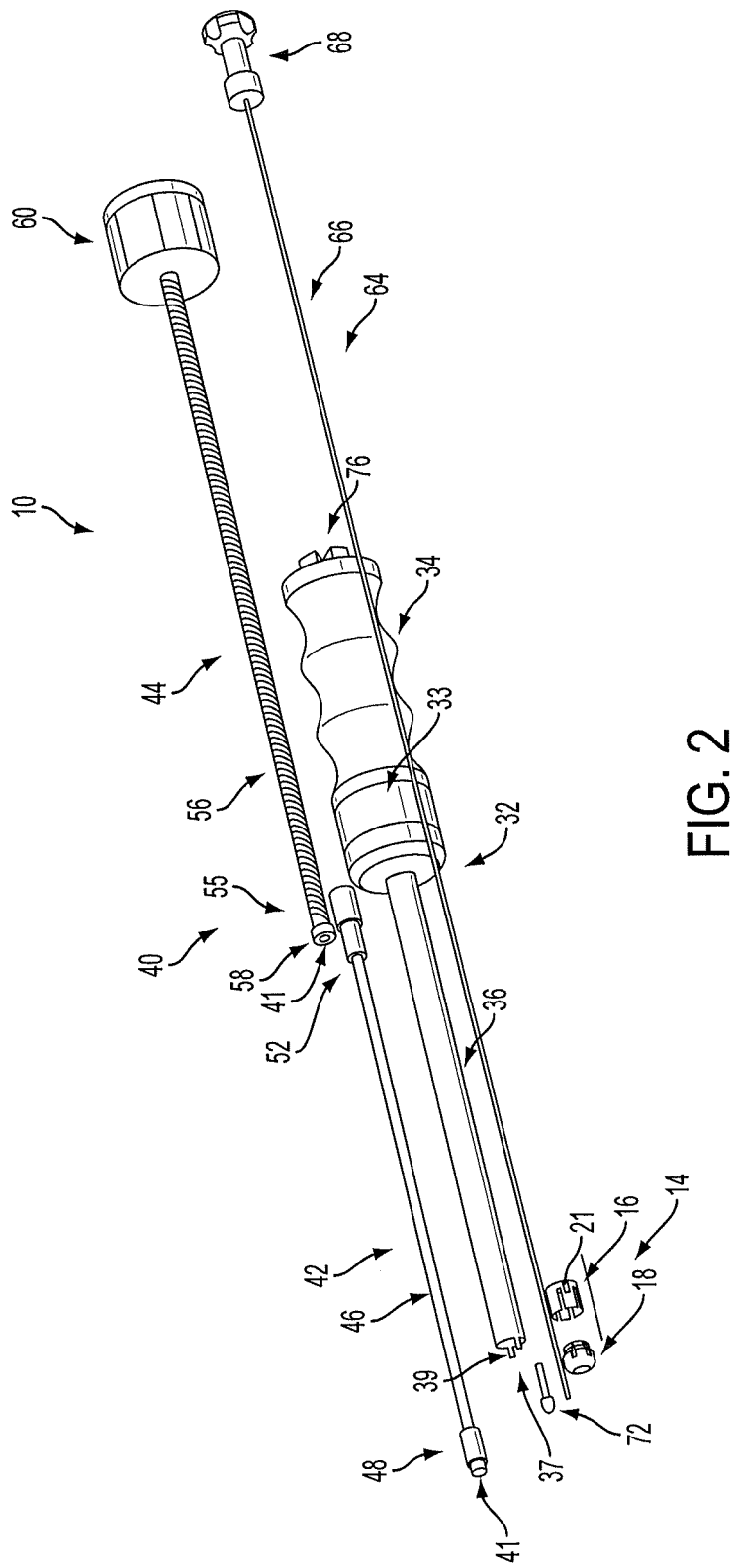
FIG. 2 is an exploded view of the embodiment of the anastomosis system depicted in FIG. 1.
Figure 8:
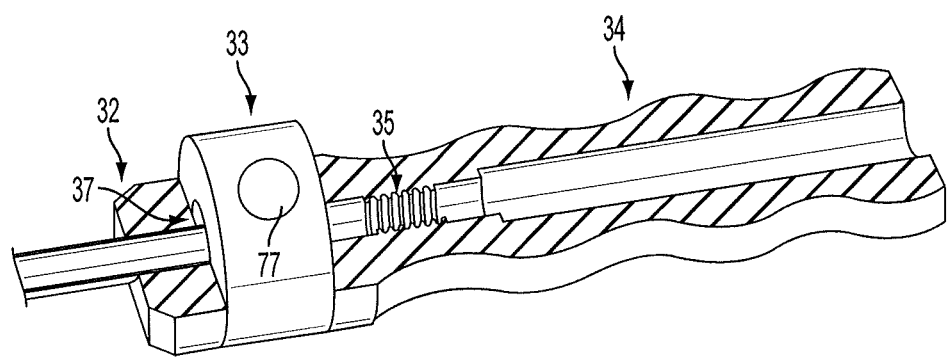
FIG. 8 is partial cross-sectional view of the handle assembly of FIG. 7.

As shown in FIG. 1, portions of the handle assembly 32, intermediate applicator assembly 40, and inner applicator assembly 64 form coaxial elongate members when the anastomosis system 10 is assembled. At least a portion of the handle assembly 32 and intermediate applicator assembly 40 define lumens 37, 41 forming passageways therethrough. As shown in FIGS. 2 and 8, the handle assembly 32 has a lumen 37 that is sized and shaped to receive at least a portion of the intermediate applicator assembly 40. Additionally, the intermediate applicator assembly 40 has a lumen 41 (see FIG. 2) that is sized and shaped to receive at least a portion of the inner applicator assembly 64. Thus, when the respective members 40, 64 are received within the appropriate lumens 41, 37, as the instrument 12 is assembled, the handle assembly 32, intermediate applicator assembly 40, and inner applicator assembly 64 provide coaxial arrangement of the members 32, 40 and 64.

As can best be seen in FIGS., 2, 13A, and 15, in the present embodiment, the intermediate applicator assembly 40 comprises two separate assemblies, an upper tube assembly 42 and a lower tube assembly 44, that work together but can be detached for storage. Thus, the intermediate applicator assembly 40 includes a proximal rotary control 60, a distal end 48 adapted to mount the upper ring 18 thereto and to deploy the lower urethra ring 16 securement elements 24 (i.e., a combination applicator and deployer), and a rotary-to-translating motion converter positioned between the proximal rotary control 60 and distal end 48. In alternative embodiments, the intermediate applicator assembly 40 may be provided as a single assembly of parts not intended to be detachable after use.

Figure 9:
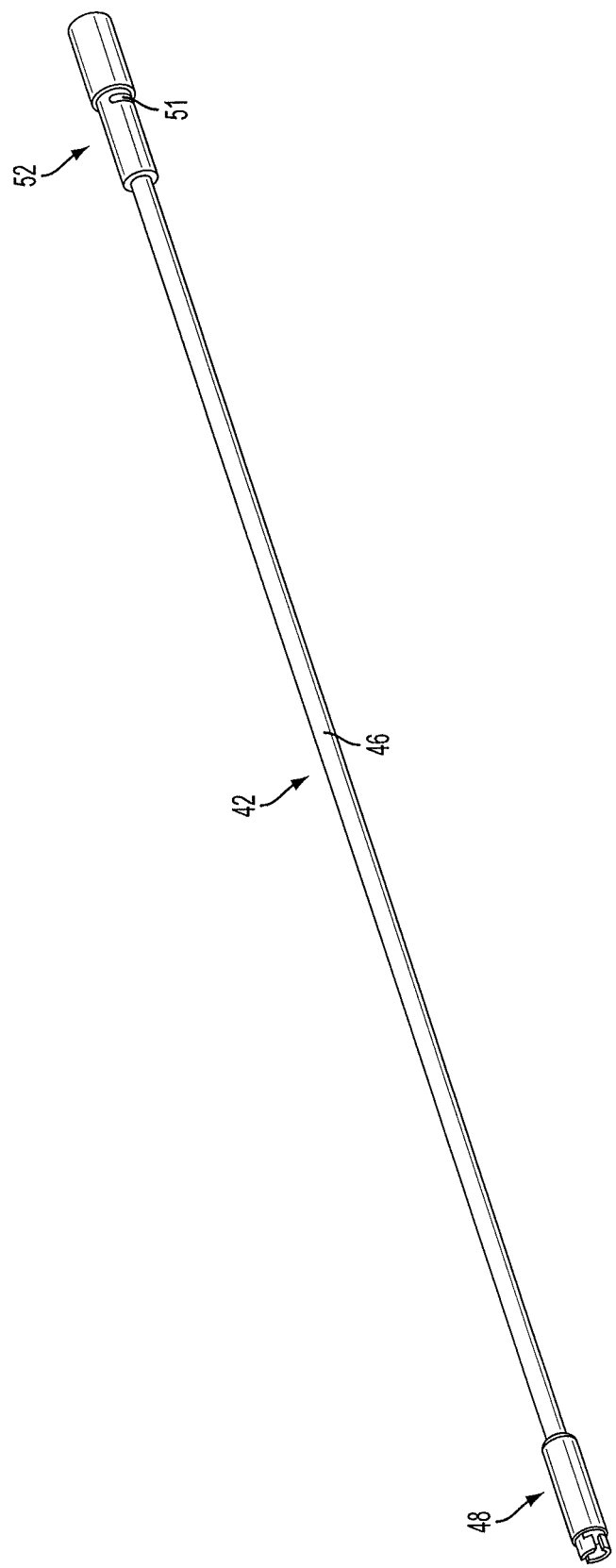
FIG. 9 is a perspective view a portion of the anastomosis system depicted in FIG. 1 showing a portion of an applicator assembly.
Figure 12:
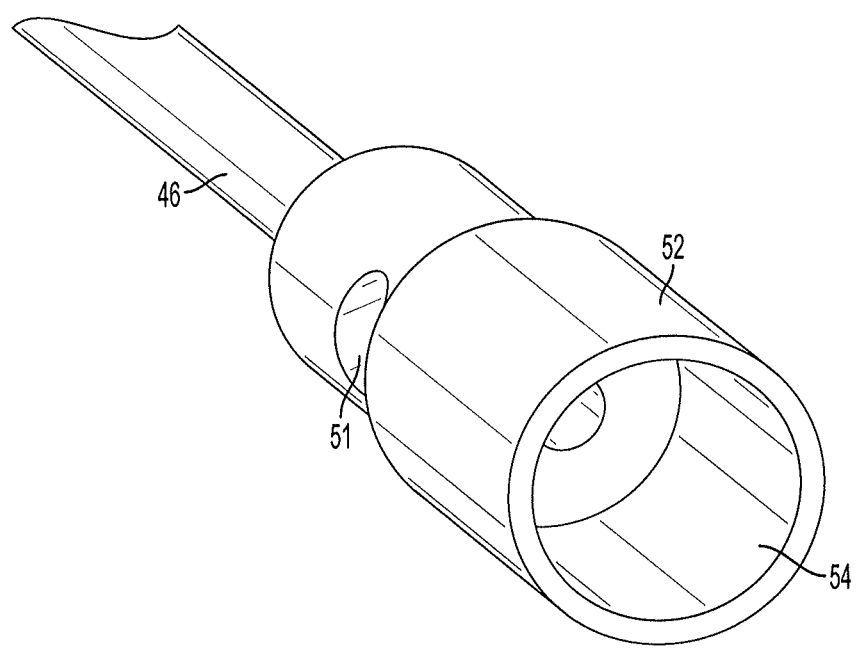
FIG. 12 is a perspective view of a portion of the anastomosis system depicted in FIG. 1 showing a proximal end of an intermediate applicator assembly.
Figure 13A:
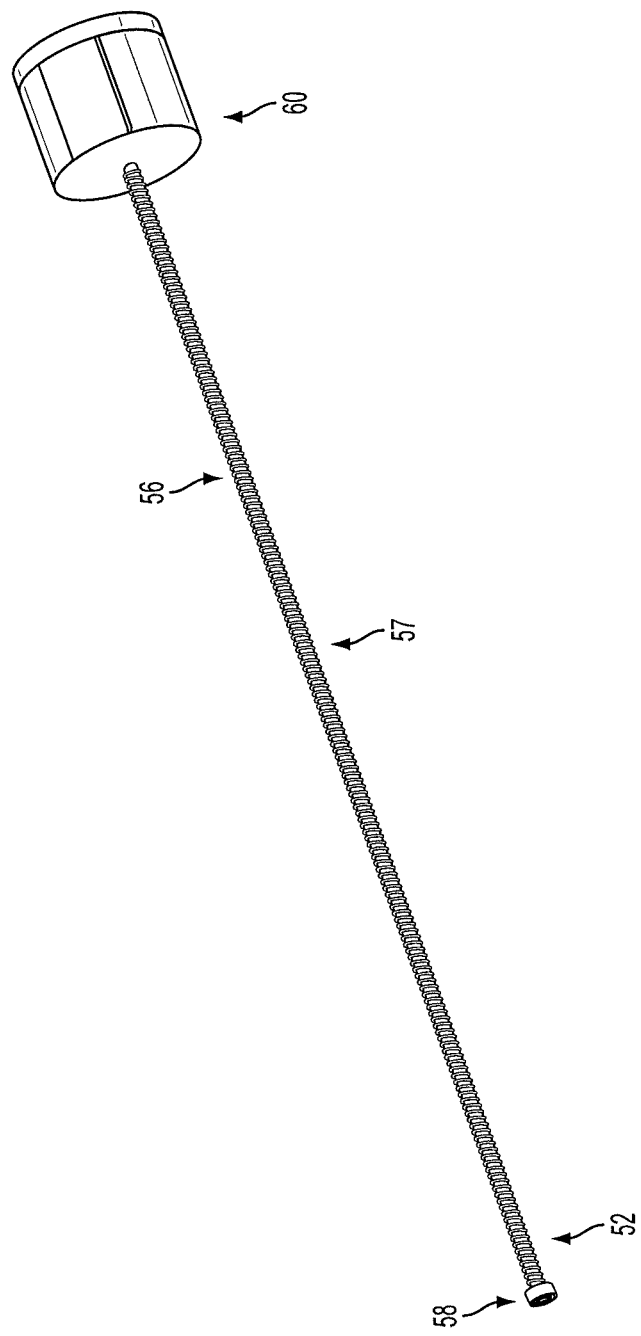
FIG. 13A is a perspective view of a portion of the anastomosis system depicted in FIG. 1 showing a lower tube assembly of the intermediate applicator assembly.
Figure 13B:
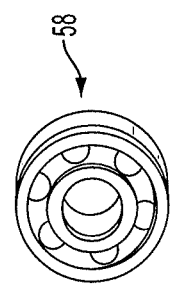
FIG. 13B is a perspective view of a portion of the anastomosis system depicted in FIG. 1 showing an exemplary rotary bearing.
Figure 14:
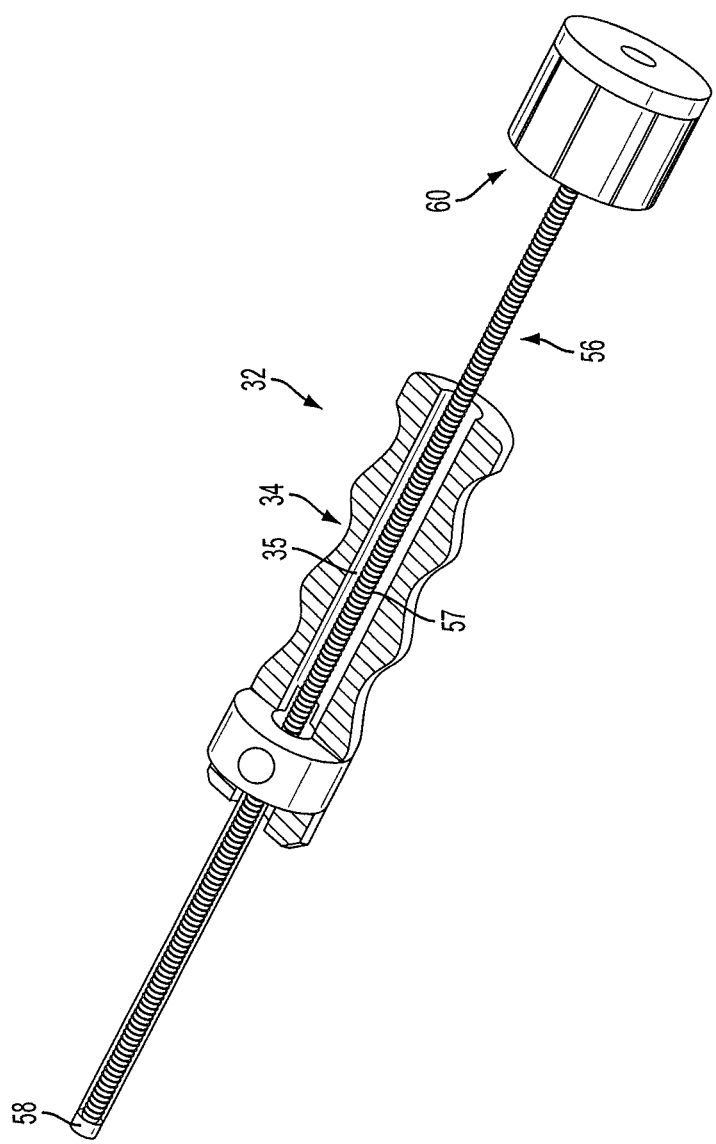
FIG. 14 a partial cross-sectional view of a portion of the anastomosis system depicted in FIG. 1 showing a handle assembly with the lower tube assembly positioned within a portion of the handle assembly.
Figure 15:
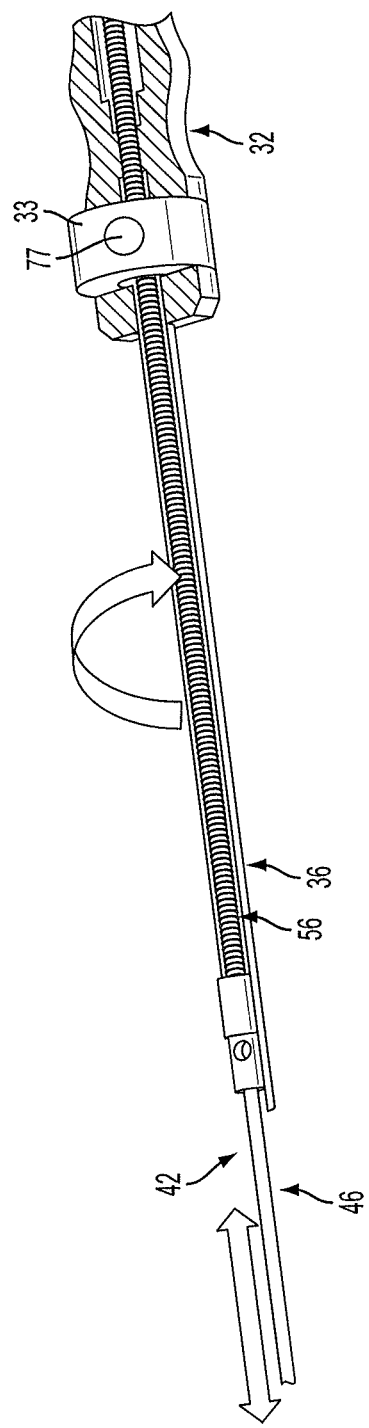
FIG. 15 is partial cross-sectional view of a portion of the anastomosis system depicted in FIG. 1 showing a handle assembly with the lower tube assembly positioned within a portion of the handle assembly.
Figure 16:
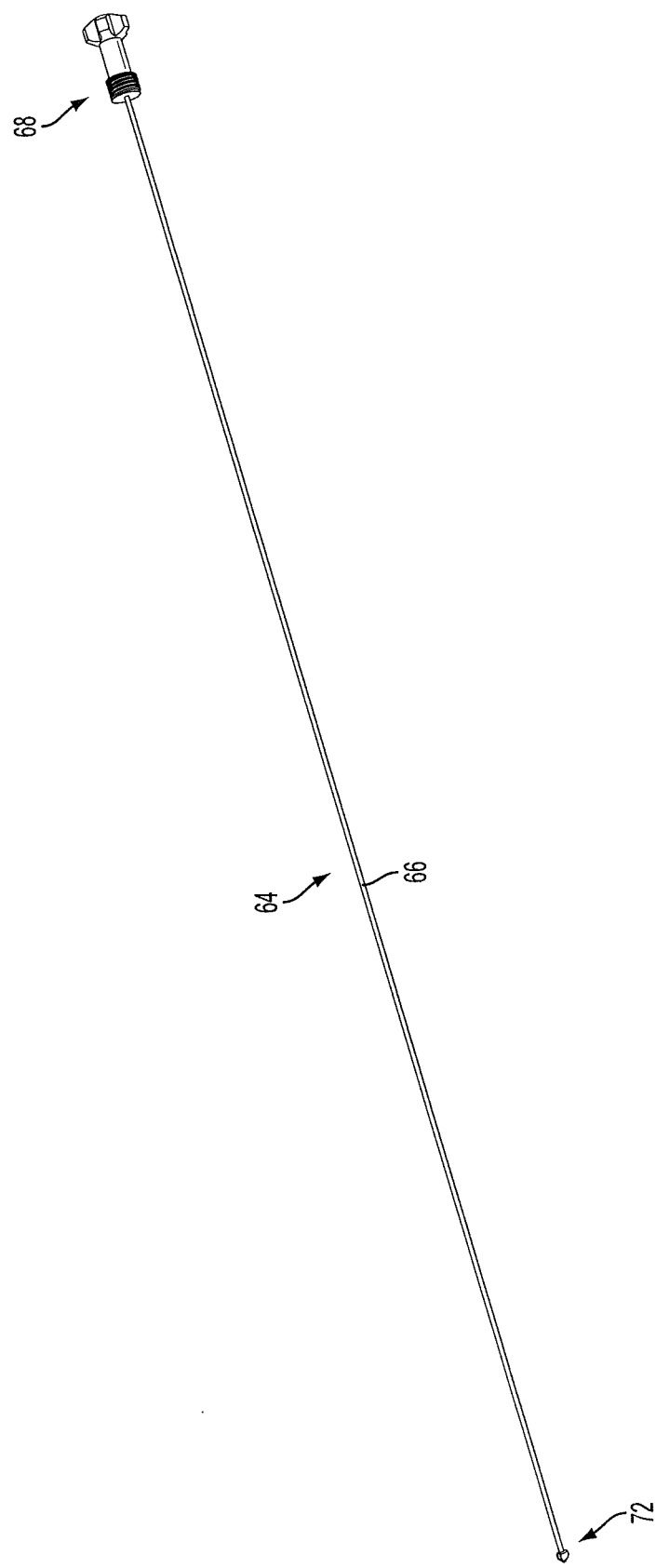
FIG. 16 is a perspective view of a portion of the anastomosis system depicted in FIG. 1 showing an inner applicator assembly.

Referring to FIGS. 2 and 9, the upper tube assembly 42 includes the distal end applicator/deployer (referred to as the lower ring securement element deployer 48), a hollow upper tube 46, and a proximal end 52. As depicted in FIG. 13A, the lower tube assembly 44 includes a distal end 55, a hollow lower tube 56, and the proximal rotary control (e.g., knob) 60. The hollow upper tube 46 and the hollow lower tube 56 are axially alignable and sized so that they are coaxially receivable through the lumen 37 of the handle assembly 32 and cooperatively define a lumen 41 therethrough. Referring now also to FIGS. 12 and 13, the proximal end 52 of the upper tube 46 includes an axial recess 54 and the distal end 55 of the lower tube 56 has a rotary bearing 58 that is received in the axial recess 54 (such as by a press-fit connection). The outer surface of the lower tube 56 has outer (male) screw threads 57 which cooperate with the rotary bearing 58, to convert rotational motion of the rotary control knob 60 to axial movement of the upper tube 46, as described below.

As seen best in FIGS. 14, 15, and 40-42, the handle assembly 32 comprises a handle grip member 34 that includes a portion of the lumen 37 and has inner (female) threads 35. When assembled, the outer threads 57 of the lower tube 56 engage the inner threads 35 of the handle grip member 34. During operation, when the knob 60 is rotated, the outer threads 57 of lower tube 56 engage the inner threads 35 of the handle grip member 34 to translate the lower tube 56 axially with respect to the handle assembly 32 (see FIG. 14). However, the rotary bearing 58 does not transmit the rotation force to the upper tube 46 via the axial recess 54. As a result, the upper tube translates axially, but does not rotate (see FIG. 15). In an exemplary embodiment of a bladder-urethra anastomosis surgical instrument, the rotary bearing 58 may be a deep groove ball bearing having an outer diameter of 7.0 mm and an internal diameter of 3.0 mm (see FIG. 13B). Alternatively, another known motion-converting mechanism can be used for converting the rotary and axial motion of the lower tube 56 to the desired axial motion of the upper tube 46, such as known nut-and-screw mechanisms.

Figure 10:
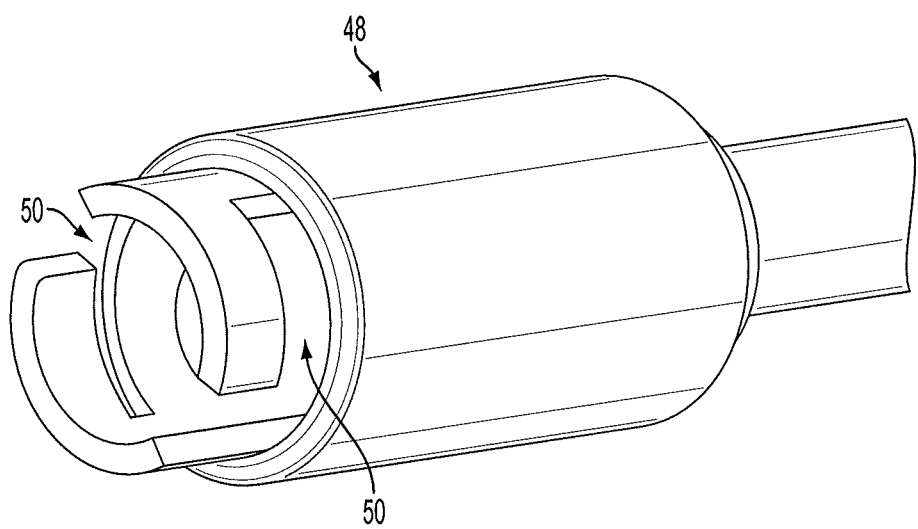
FIG. 10 is a perspective view of a portion of the anastomosis system depicted in FIG. 1 showing a lower ring securement element deployer.
Figure 11:
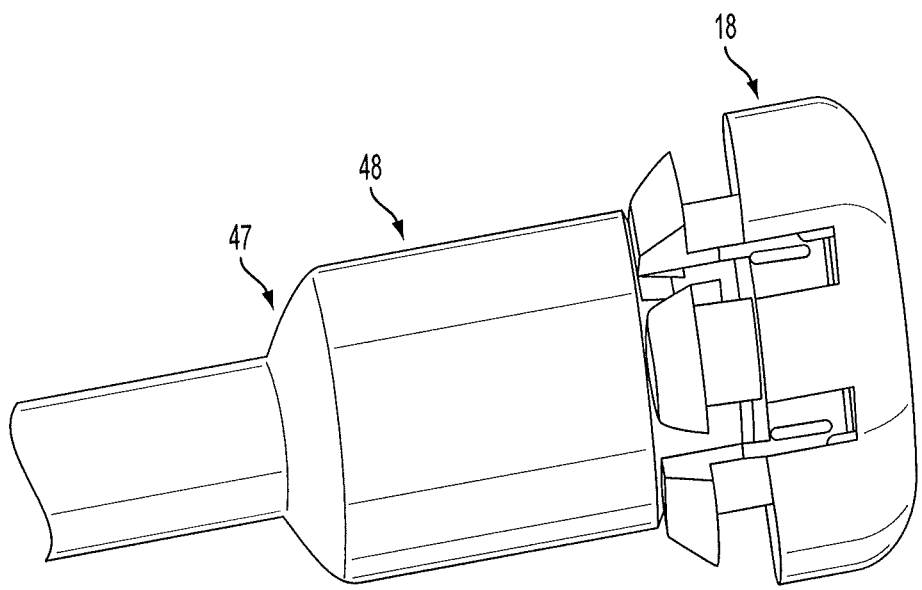
FIG. 11 is a perspective view of a portion of the anastomosis system depicted in FIG. 1 showing a portion of the lower ring securement element deployer with the upper ring included thereon.

Referring to FIGS. 9-11, the distal end of the upper tube 46 comprises the lower ring securement element deployer 48, which extends distally therefrom and is adapted to deploy the lower ring securement elements 24 upon the axial translation of the upper tube 46 with respect to the grip member 34. The lower ring securement element deployer 48 defines a tapered surface extending from the upper tube 46 and forming cam surface 47. The narrower portion of the tapered cam surface 47 of the lower ring securement element deployer 48 is oriented towards the proximal direction and the diameter of the wider portion of the tapered cam surface 47 is sized to be receivable within the lumen of the lower ring 16, but wide enough to engage the cooperating cam surfaces 25 of the lower ring securement elements 24. As shown, the cam surface 47 (seen best in FIG. 11) engages cooperating cam surfaces 25 of the lower ring securement elements 24 to pivot securement elements 24 towards the deployed position when the upper tube 46 is axially retracted with respect to the handle assembly 32 (as described in further detail with respect to FIGS. 24 and 25).

Figure 36:
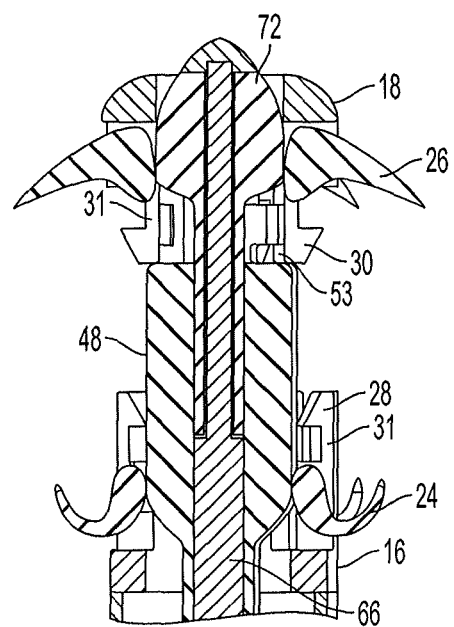
FIG. 36 is a cross-sectional view of the two-part coupling ring assembly depicted in FIG. 35, with securement elements in the deployed position.

The lower ring securement element deployer 48 translates axially with respect to the handle portion 34 as the control knob 60 is rotated. As mentioned, the lower ring securement element deployer 48 is adapted to both mount thereto the upper bladder ring 18 and to deploy the lower urethra ring securement elements 24, using cam surface 27. The lower ring securement element deployer 48 and the upper ring 18 have cooperating ring-mounting connectors such that the upper ring 18 is releasably mounted to the deployer 48. As best seen in FIGS. 10 and 11, the ring-mounting connectors of the lower ring securement element deployer 48 can be provided by angular slots 50, for example, two circumferential slots each in communication with a respective axial slot, as depicted. Referring now to FIGS. 10 and 36, the ring-mounting connectors of the upper ring 18 may be provided with radially inward extending tabs 53 that slide within the angular slots of the deployer 48. As such, the depicted cooperating ring-mounting connectors form a conventional bayonet fitting that is released by rotating the deployer 48 with respect to the upper ring 18. Alternatively, other types of releasable ring-mounting connectors known in the art can be provided.

Referring now to FIGS. 39-42, the proximal end 52 of the upper tube assembly 42 of the intermediate applicator assembly 40 includes at least one lock element that engages with at least one lock element of the handle 32. As shown, the lock element consists of two radial recesses 51 located within the proximal end 52 of the upper tube assembly 42 (see FIGS. 9 and 12), and extending generally perpendicular to the longitudinal axis of the upper tube assembly 42. The recesses 51 are adapted to engage two radially-movable lock buttons 77 in the rotary lock ring 33 of the handle 32, when the device 12 is assembled. The buttons 77 include narrow inner portions 77a, for engaging the radial recesses 51, and generally wider outer portions 77b that are sized for manual operation by a user. In order to disengage the upper ring 18, the buttons 77 are depressed inwardly towards the longitudinal axis of the device, such that the inner portions 77a are slid into the recesses 51, thereby engaging the lock ring 33 and the upper tube assembly 42 and hence, the intermediate applicator assembly 40 together so that they rotate together to release the upper ring 18 from the lower ring securement element deployer 48.

Referring now to FIGS. 16-20, the inner applicator assembly 64 includes an elongate rod 66, a proximal rotary control, such as a knob 68, and a distal end having a deployer element 72. These components can be provided as separate pieces assembled together. By way of example, the embodiment depicted herein, and shown best in FIG. 2, provides for the rod 66 and the deployer element 72 to be detachable. Alternatively, the rod 66 and deployer element 72 can be of unitary construction. During assembly, the elongate rod 66 is coaxially receivable within the lumen 41 of the tubes 46 and 56 of the intermediate applicator assembly 40. In the depicted embodiment, the rotary control is provided by a knob 68 with outer screw threads 70 that mate with inner screw threads of knob 60. In this way, rotating the knob 68 causes the elongate rod 66 to translate relative to the tubes 46 and 56 of the intermediate applicator assembly 40 (see FIGS. 18-20). In other embodiments, the controls of the two applicator assemblies are interconnected by other conventional structures for producing translating relative motion.

Figure 17:
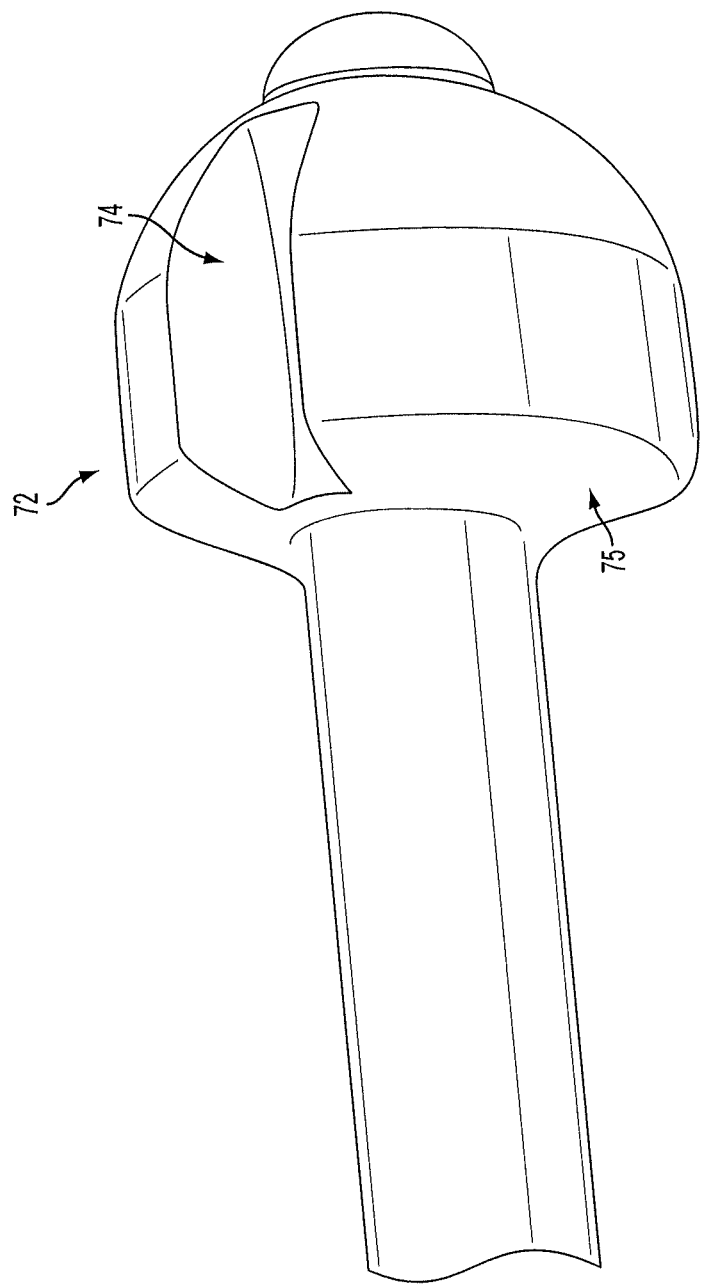
FIG. 17 is a perspective view of a portion of the anastomosis system depicted in FIG. 1 showing an upper coupling part securement element deployer on the distal end of an inner applicator assembly.
Figure 18:
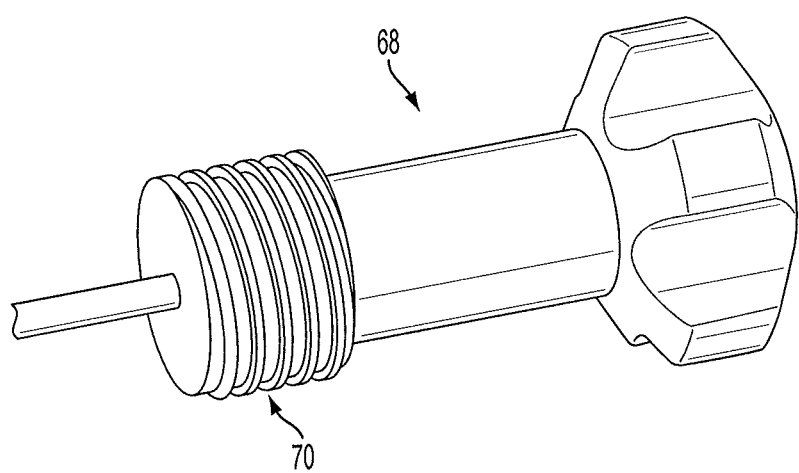
FIG. 18 is a perspective view of a portion of the anastomosis system depicted in FIG. 1 showing a knob on the proximal end of an inner applicator assembly.
Figure 19:
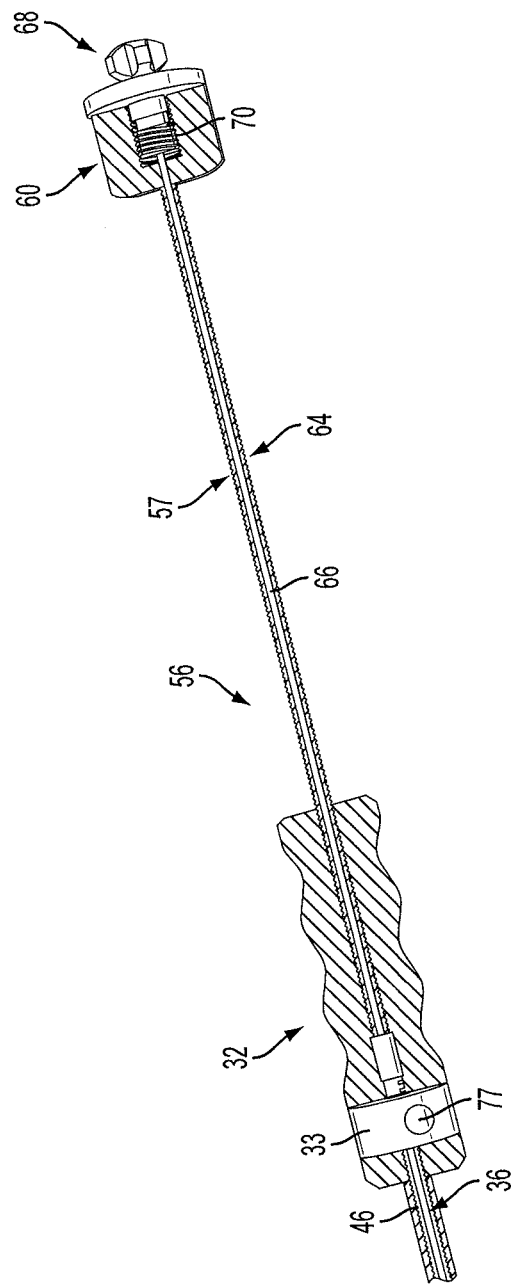
FIG. 19 is a partial cross-sectional view of a portion of the anastomosis system depicted in FIG. 1 showing the inner applicator assembly coaxially received within a portion of the intermediate applicator assembly and handle assembly.
Figure 20:
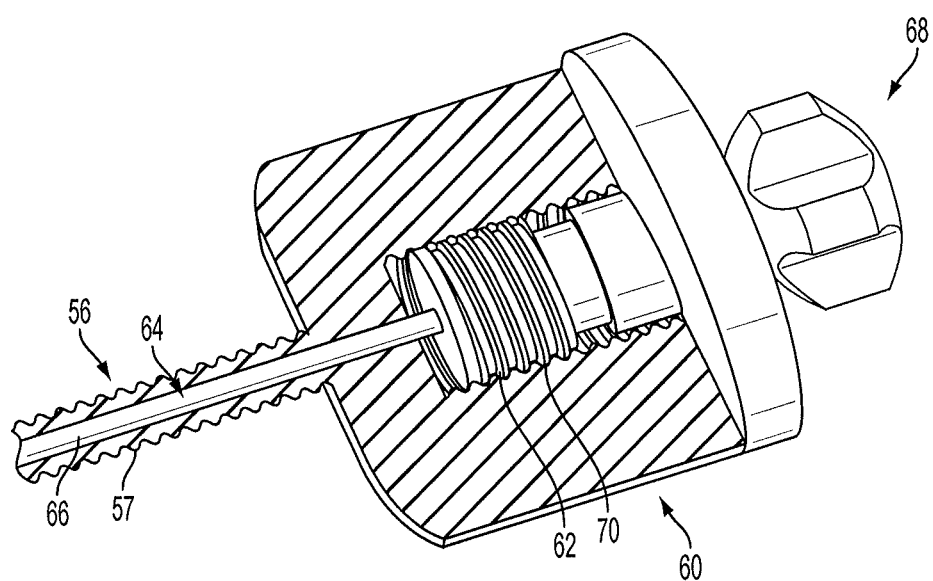
FIG. 20 is a partial cross sectional view of a portion of the anastomosis system depicted in FIG. 1 showing a knob on the proximal end of the inner applicator assembly.

Referring now to FIG. 17, the distal end of the rod 66, which includes the upper ring securement element deployer 72, is adapted to deploy the upper ring securement elements 26 upon the axial translation of the rod 66. The upper ring securement element deployer 72 defines a tapered surface extending from the rod 66 and forming cam surface 75. The narrower portion of the tapered cam surface 75 of the upper ring securement element deployer 72 is oriented towards the proximal direction and the diameter of the wider portion of the tapered cam surface 75 is sized to be receivable within the lumen of the upper ring 18, but wide enough to engage the cam surfaces 27 of the upper ring securement elements 26. As shown in FIGS. 30 and 31, the cam surface 75 engages cooperating cam surfaces 27 of the upper ring securement elements 26 to pivot the upper ring securement elements 26 towards the deployed position when the rod 66 is axially retracted with respect to the handle assembly 34. The upper ring securement element deployer 72 can also include anti-rotation mounting features, such as axial channel 74 that receives an inwardly protruding element of the upper ring 18, for preventing rotation between the deployer 72 and the upper ring 18.

Figure 22:
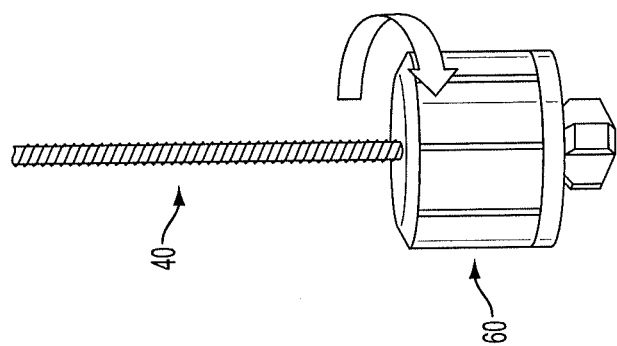
FIG. 22 is a side view of a portion of the anastomosis system depicted in FIG. 1 showing a proximal end of the intermediate applicator assembly.
Figure 21:
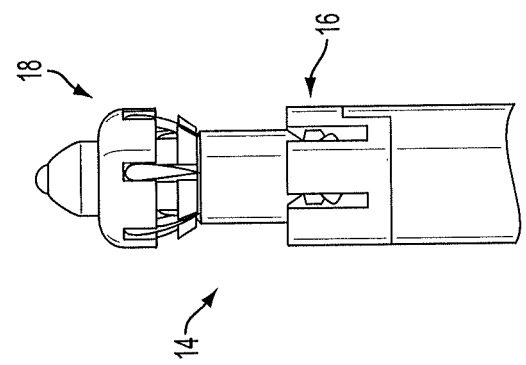
FIG. 21 is a side view of a portion of the anastomosis system depicted in FIG. 1 showing a two-part coupling assembly with securement elements in the retracted position.

The operation of the instrument 12 and ring assembly 14 of the first example embodiment, as well as example anastomosis methods, are shown in FIGS. 21-43. As depicted in FIG. 21, the instrument 12 is inserted through the urethra (not shown) to position lower ring 16 within urethra neck by pushing grip member 34 of handle assembly 32 to advance the lower ring 16 coupled to the instrument 12 into the urethra neck. Once the lower ring 16 is aligned at a suitable position within the urethra neck, the knob 60 of intermediate applicator assembly 40 is rotated counter-clockwise, as shown in FIG. 22. Counter-clockwise rotation of the knob 60 causes the lower ring securement element deployer 48 defining cam surface 47 to axially retract in the proximal direction (i.e., translate axially with respect to the handle assembly 32) through the lumen of the lower ring 16. As the tapered portion of the lower ring securement element deployer 48 forming the cam surface 47 further advances through the lumen of the lower ring 16 in the proximal direction, the cam surface 47 engages cooperating cam surfaces 25 on the inner facing surface of the lower ring securement elements 24 (see FIGS. 24-26). Engagement of the cam surface 47 with the cam surfaces 25 of the lower ring securement elements 24 displaces the lower securement elements 24, thereby urging the securement elements 24 to pivot around a pivot pin 23 and extend outward towards the deployed position.

Figure 23:
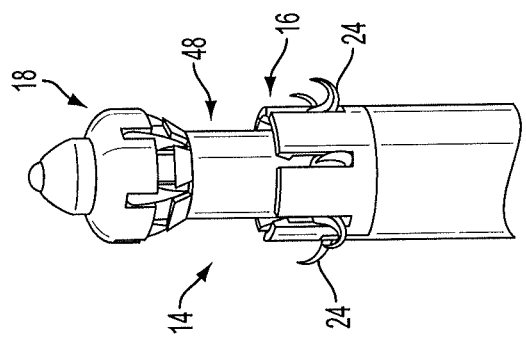
FIG. 23 is a side view of a portion of the anastomosis system depicted in FIG. 1 showing a two-part coupling assembly.

FIG. 23 shows the arrangement of the anastomosis system 10 with the lower securement elements 24 in the deployed position with the upper securement elements 26 remaining in the retracted position. FIG. 24-26 show in detail the lower ring 16, with lower ring securement elements 24 in the retracted position (FIGS. 24 and 25) and deployed position (FIG. 26). Arrows in FIG. 25 illustrate the direction of movement of the deployment of the lower securement elements 24. The outward movement of the lower ring securement elements 24 to the deployed position causes the securement elements 24 to engage the urethra neck, such as by piercing the urethral wall tissue. The surgeon may compress the urethra tissue around the lower ring 16 to ensure that the securement elements 24 securely engage the urethra.

At this point in the procedure, the lower ring 16 mounted on the surgical instrument 12 securely engages the urethra neck by the lower ring securement elements 24. To maintain engagement of the securement elements 24 with the urethra tissue, the surgeon may apply gentle pressure to the grip member 34 in the distal direction such that the lower ring securement elements 24 are pushed generally in the direction of the curvature of the securement elements 24.

Figure 27:
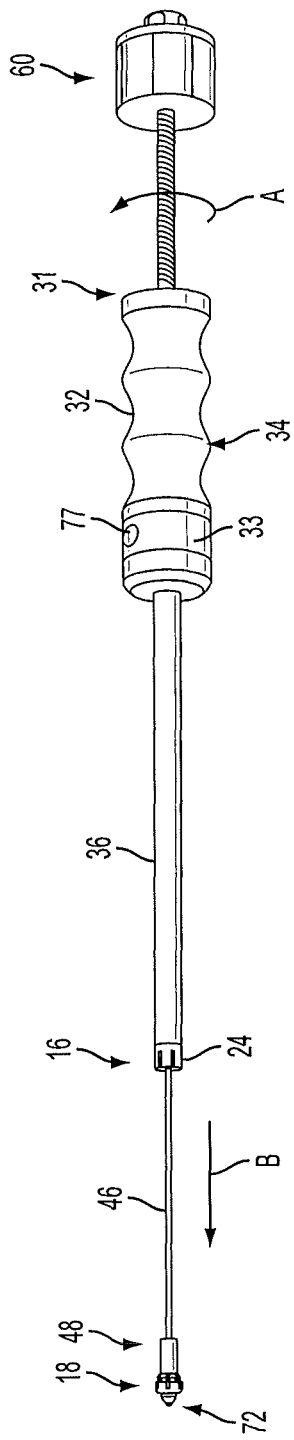
FIG. 27 is a perspective view of the anastomosis system depicted in FIG. 1.

Turning now to FIG. 27, after the deployment of the lower securement elements 24, the surgeon may press slightly forward (i.e., distally) on grip member 34 to maintain engagement of lower ring securement elements 24 and rotate the knob 60 of the intermediate applicator assembly 40 clockwise to cause the lower ring securement element deployer 48 to translate forward with respect to the handle assembly 32 (i.e., axially extend). In FIG. 27, arrow "A" illustrates the clockwise rotation of the knob 60 and arrow "B" illustrates the direction of movement of the axial extension of the lower ring securement element deployer 48. Axial extension of the lower ring securement element deployer 48 carries the upper ring 18 forward and, if necessary, after manipulation of the angle or position of the surgical instrument 12, into the bladder neck. FIG. 27 shows the arrangement of the anastomosis system 10 after the knob 60 is rotated and the upper ring 18 is axially extended. The lower ring securement elements 24 remain in the deployed position and, in use, would be engaged with the urethra neck such as through continued application of gentle pressure on grip member 34 to maintain engagement of lower ring securement elements 24.

Figure 28:
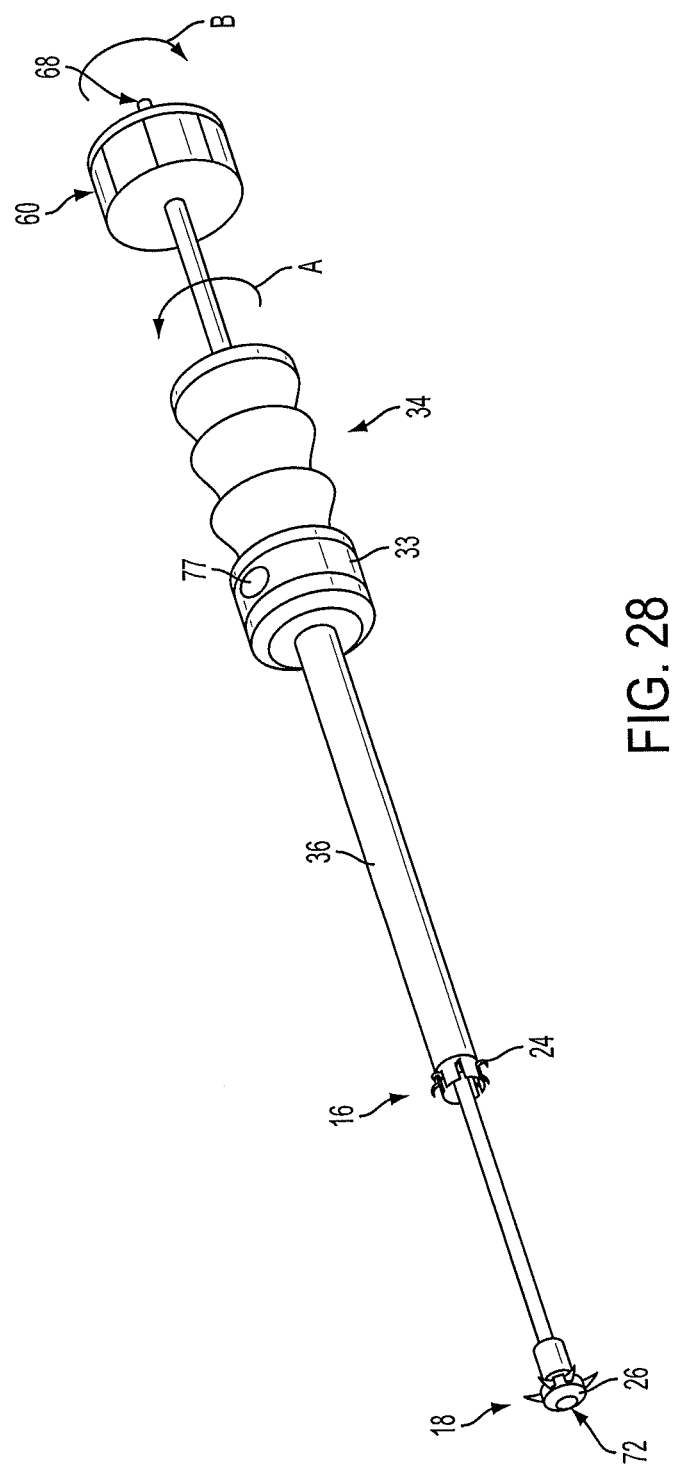
FIG. 28 is a perspective view of the anastomosis system depicted in FIG. 1.
Figure 32:
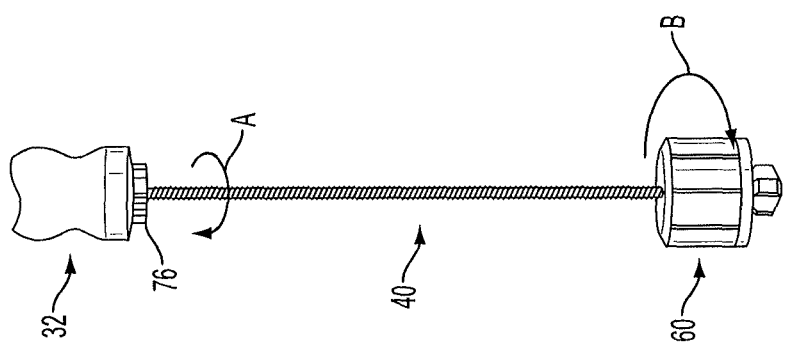
FIG. 32 is a side view of a portion of the anastomosis system depicted in FIG. 1, showing a knob on the proximal end of the intermediate applicator assembly.
Figure 35:
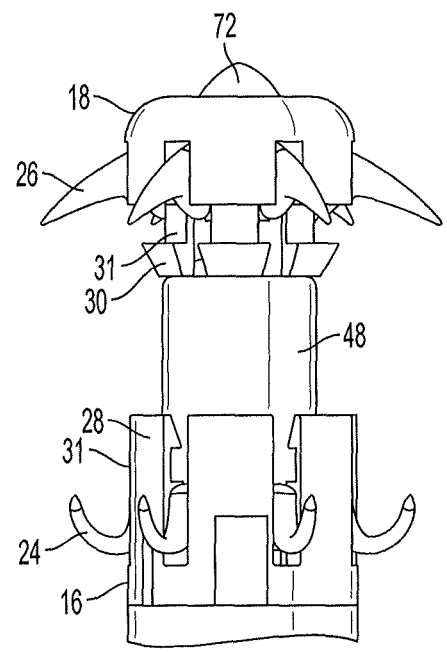
FIG. 35 is a side view of a portion of the anastomosis system depicted in FIG. 1, showing a two-part coupling assembly with securement elements in the deployed position.

As shown in FIG. 28, when the upper ring 18 is in a desired position within the bladder neck (not shown), the surgeon rotates the lock nut 76 on the proximal end 31 of the handle assembly 32 in a first angular direction, for example clockwise. Arrow "A" in FIGS. 28 and 32 illustrates clockwise rotation of the lock nut 76. The rotation of lock nut 76 restricts or prevents rotation of the intermediate applicator assembly 40 with respect to the handle assembly 32. The surgeon then rotates the knob 68 counter-clockwise, as shown by arrow "B" in FIGS. 28 and 32, thereby causing the inner applicator assembly 64 to rotate and axially retract in the proximal direction with respect to the handle assembly 32. As depicted in FIGS. 30 and 31, axial retraction of inner applicator assembly 64 urges the cam surface 75 of upper ring securement element deployer 72 into engagement with cooperating cam surfaces 27 of upper ring securement elements 26. As the tapered portion of the upper ring securement element deployer 72 forming the cam surface 75 further advances through the lumen of the upper ring 18 in the proximal direction, the cam surface 75 engages cooperating cam surfaces 27 on the inner facing surface of the upper ring securement elements 26. Engagement of the cam surface 75 with the cam surfaces 27 of the upper ring securement elements 26 displaces the upper ring securement elements 26, thereby urging the securement elements 26 to pivot around a pivot pin 43 and extend outward towards the deployed position.

FIG. 28 shows the arrangement of the anastomosis system 10 with the upper ring securement elements 26 in the deployed position. FIG. 29-31 show in detail the operation of the upper ring 18 with upper ring securement elements 26 in the retracted position (FIGS. 29 and 30) and subsequently moved to a deployed position (FIG. 31). Arrows in FIG. 31 illustrate the direction of movement of the deployment of the upper securement elements 26. The outward movement of the upper ring securement elements 26 to the deployed position causes the securement elements 26 to engage the bladder neck, such as by piercing the bladder tissue. The surgeon may compress the bladder tissue around the upper ring 18 to ensure that the securement elements 26 securely engage the bladder.

Figure 34:
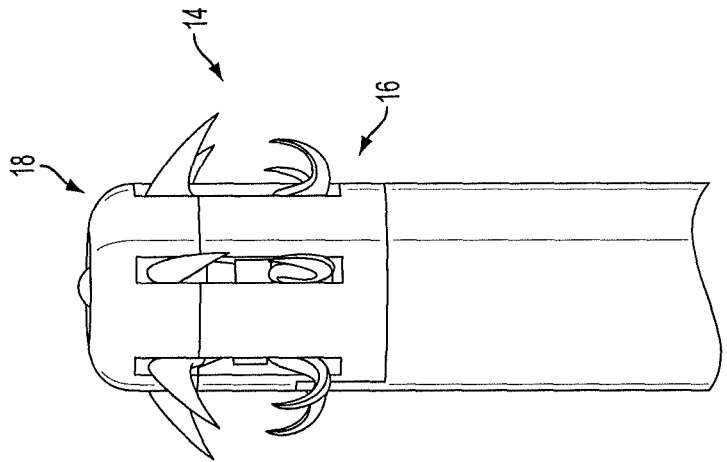
FIG. 34 is a side view of a portion of the anastomosis system depicted in FIG. 1, showing a two-part coupling assembly with securement elements in the deployed position and the upper and lower coupling rings joined together.
Figure 33:
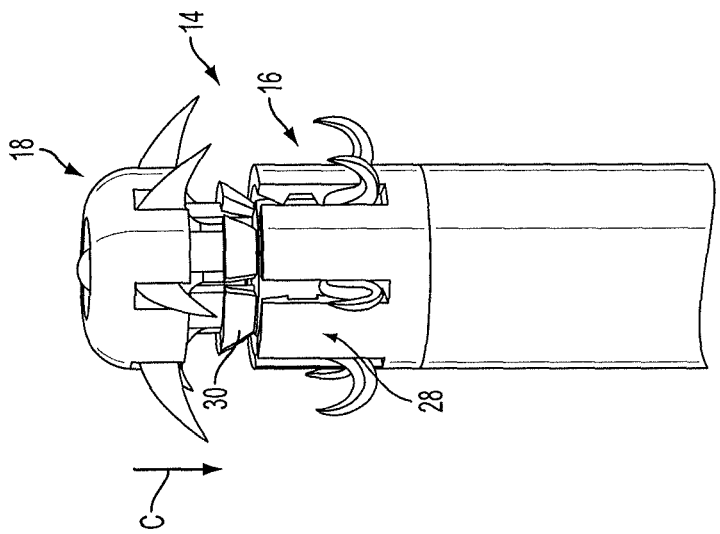
FIG. 33 is a side view of a portion of the anastomosis system depicted in FIG. 1, showing a two-part coupling assembly with securement elements in the deployed position.

Referring now to FIGS. 32-34, with the bladder neck securely engaged by the upper ring securement elements 26 of the upper ring 18, the surgeon may rotate the lock nut 76 in a second angular direction, for example counter clockwise, to unlock the intermediate applicator assembly 40. Arrow "A" in FIG. 32 shows the counter clockwise rotation of the lock nut 76. Then, as shown in FIG. 32, the surgeon rotates of the knob 60 of intermediate applicator assembly 40 counter-clockwise to cause the intermediate applicator assembly 40 to axially retract (i.e., translate backward) without rotating. Arrow "B" in FIG. 32 shows the counter clockwise rotation of the knob 60. Axial retraction of the intermediate applicator assembly 40 causes lower ring securement element deployer 48 to axially retract with respect to the handle assembly 32 through the lumen of lower ring 16 and to also retract the upper ring 18 mounted thereon. The operation of the instrument 12 to cause axial retraction of the upper ring 18 with respect to the handle assembly is the inversion of the operation to cause the axial extension of the upper ring 18 described above and shown in FIG. 27. Axial retraction of the upper ring 18 brings the upper ring 18 towards the lower ring 16, thereby drawing the urethra neck and bladder neck closer together.

Figure 37:
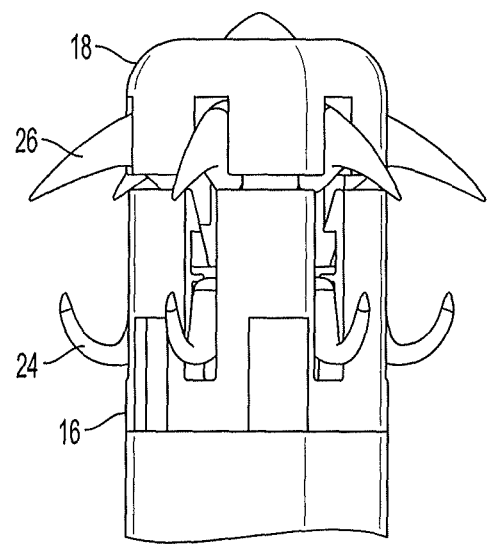
FIG. 37 is a side view of a portion of the anastomosis system depicted in FIG. 1, showing a two-part coupling assembly with securement elements in the deployed position and the upper and lower coupling parts coupled together.
Figure 38:
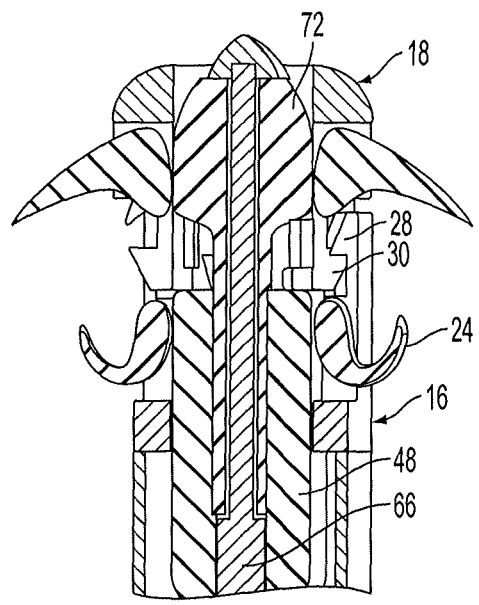
FIG. 38 is a cross sectional view of the two-part coupling assembly depicted in FIG. 37, shown with securement elements in the deployed position and the upper and lower coupling parts coupled together.

FIG. 33 shows the arrangement of the anastomosis system 10 and, more specifically, the ring assembly 14, after axial retraction of the intermediate applicator assembly 40 in the direction of arrow "C." As shown, the upper ring 18 is adjacent the lower ring 16. As shown in FIG. 34, further rotation of knob 60 causes the upper ring 18 to axially retract towards the lower ring 16 until interconnectors 28 and 30 engage to couple the upper and lower rings 18, 16 together with a snap- or press-fit connection. FIGS. 35-38 show in detail the axial retraction of upper ring 18 towards the lower ring 16 (FIGS. 35 and 36) and coupling of the upper and lower rings 18, 16 to each other (FIGS. 37 and 38).

Figure 39:
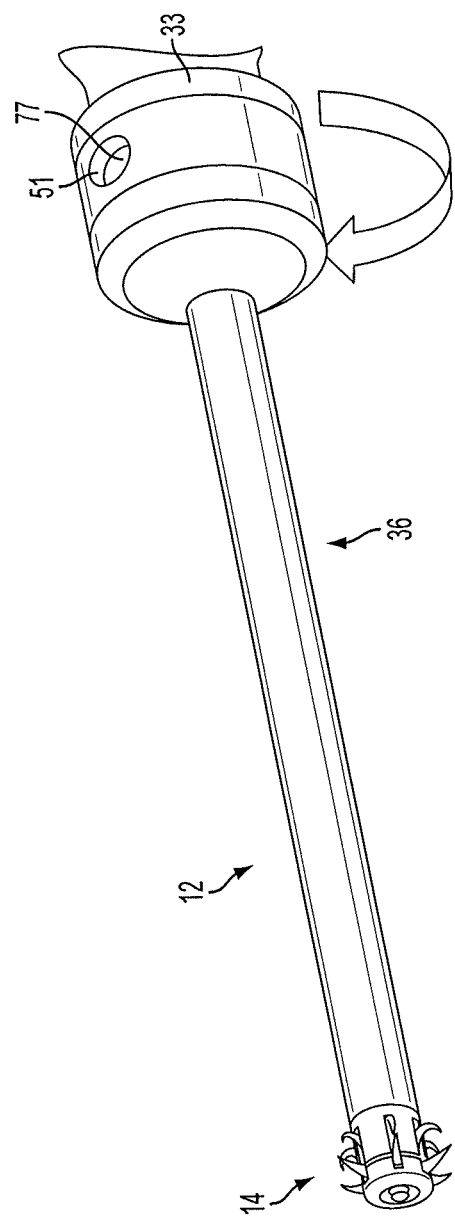
FIG. 39 is a perspective view of a portion of the anastomosis system depicted in FIG. 1, showing a handle assembly and tube.
Figures 40, 41:
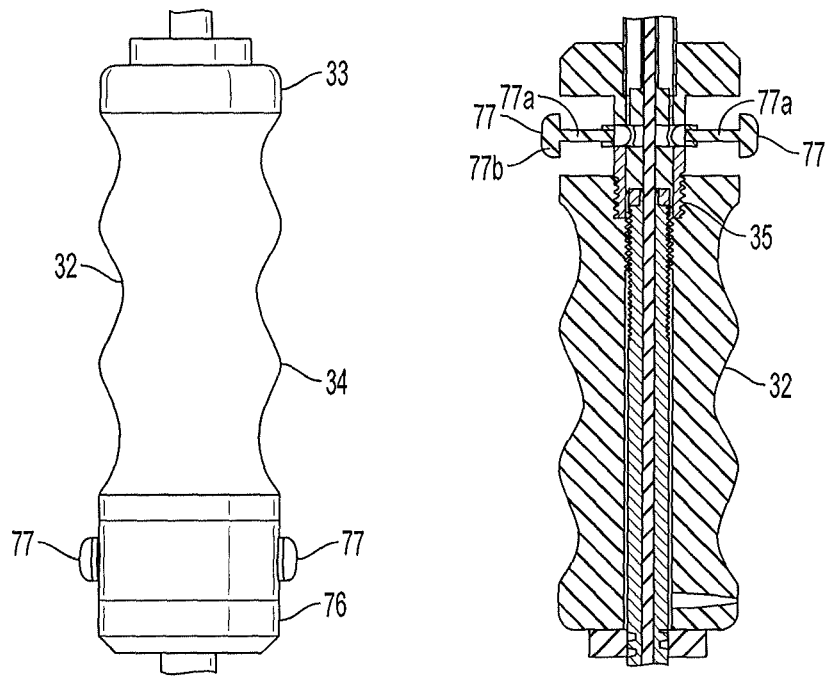
FIG. 40 is a side view of a handle assembly of the anastomosis system depicted in FIG. 1.
FIG. 41 is a cross sectional view of the handle assembly depicted in FIG. 40.
Figure 42:
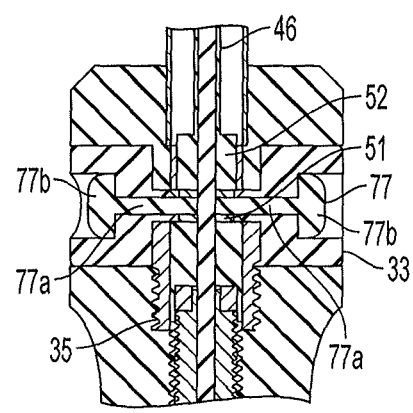
FIG. 42 is a side view of a portion of handle assembly depicted in FIG. 40, shown with a depressed locking button.
Figure 43:
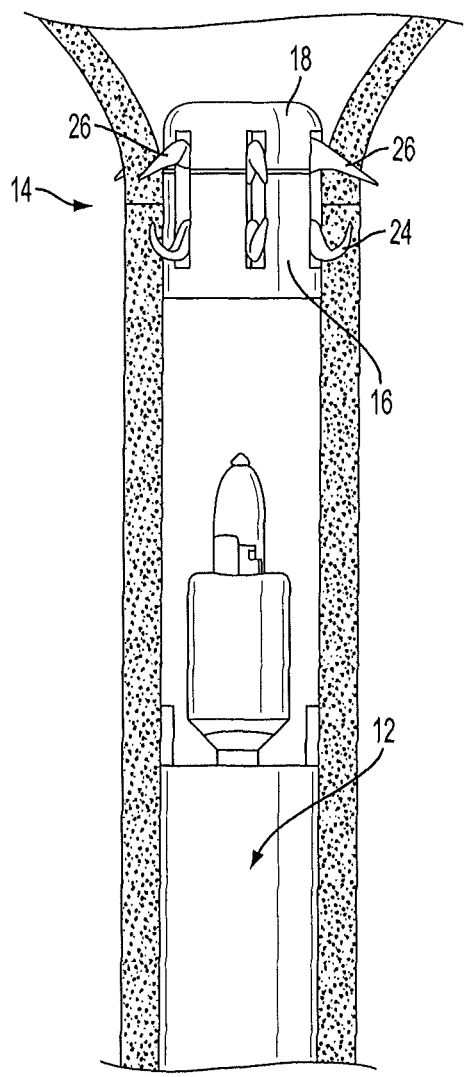
FIG. 43 is a side view of a portion of the anastomosis system showing a ring assembly installed in the bladder neck and urethra neck of a patient.

Referring now to FIG. 39, when the ring assembly 14 is in position and the upper and lower rings 18, 16 are coupled together, the ring assembly 14 may be released from the surgical instrument 12. To do this, the surgeon depresses locking button 77 inward into recess 51 of proximal end 52 of upper tube 46 of the intermediate applicator assembly 40. FIGS. 40-42 show the handle assembly 32 before (FIGS. 40 and 41) and after pressing locking button 77 (FIG. 42). Depression of the locking button 77 permits counter-clockwise rotation of the lock ring 33 with respect to the grip member 34 (as shown by the arrow in FIG. 39) which induces rotation of angular slots 50 of lower ring securement element deployer 48 out of engagement with cooperating elements on upper ring 18. The surgeon may then release lower ring 16 from the friction fit with handle tube 36 by pulling grip member 34 proximally. Finally, as shown in FIG. 43, the surgical instrument 12 may be withdrawn from the urethra leaving the ring assembly 14 to hold the urethra and bladder in anastomosis. The ring assembly 14 may be removed after a period of healing or, alternatively, may be permitted to biodegrade in place.

Figure 97:
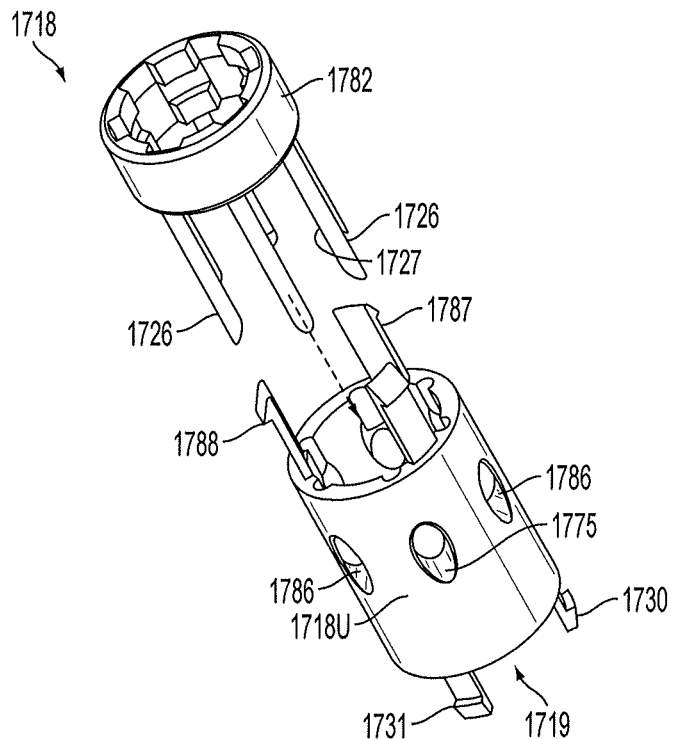
FIG. 97 a perspective view of a further alternative embodiment of an upper coupling part.
Figure 98:
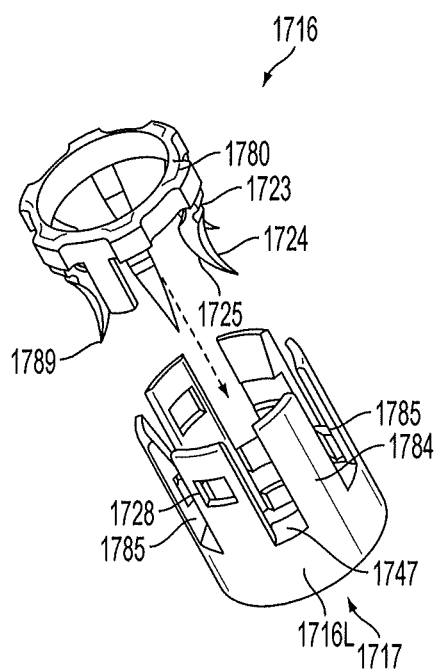
FIG. 98 is a perspective view of a further alternative embodiment of a lower coupling part.
Figure 99C:
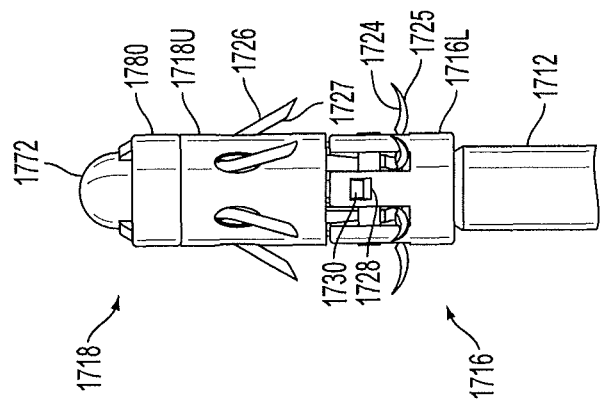
FIG. 99C is a side view of an anastomosis system with the upper and lower coupling parts depicted in FIGS. 97 and 98 coupled together.
Figure 99B:
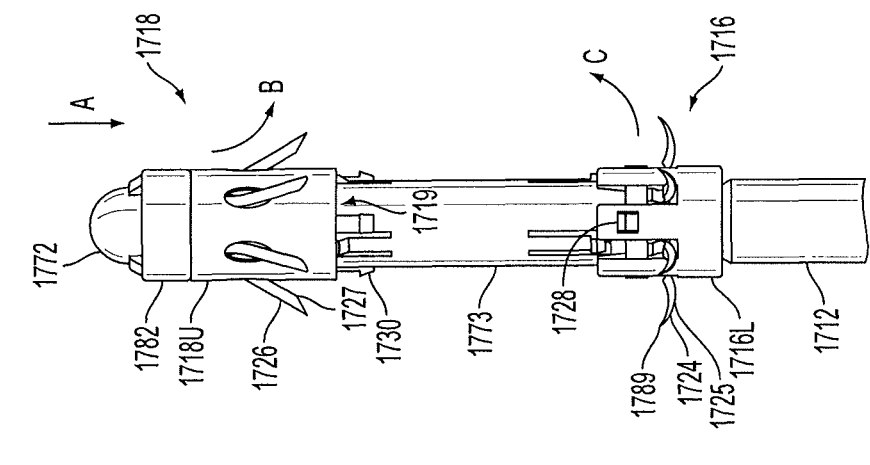
FIG. 99B is a side view of an anastomosis system with the upper and lower coupling parts depicted in FIGS. 97 and 98, both in the deployed position.
Figure 99A:
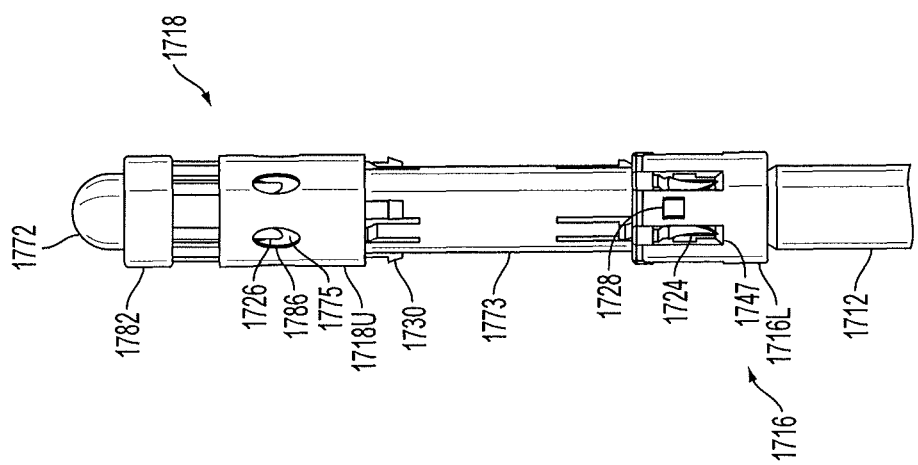
FIG. 99A is a side view of an anastomosis system with the upper and lower coupling parts depicted in FIGS. 97 and 98, both in the undeployed position.

The structure and deployment operation of an alternative embodiment of the device will now be described with respect to FIGS. 97-99c. FIGS. 97 and 98 show the structure of an alternative embodiment of a ring assembly 1714, where FIG. 97 depicts the upper ring assembly 1718 and FIG. 98 depicts the lower ring assembly 1716. The ring assembly 1714 comprises a lower ring assembly 1716, having a lower ring 1716L and a lower central ring 1780, and an upper ring assembly 1718, having an upper ring 1718U and an upper central ring 1782. The body of the upper ring 1718U defines a plurality of guide structures 1786, which extend through the circumferential wall of the upper ring 1718. As shown, the guide structures 1786 comprise openings in the sidewall of the upper ring 1718U that are sized and positioned to permit passage of securement elements 1726 therethrough, in a proximal and radial outward direction. The guide structures 1786 have angled deployer surfaces 1775 adapted to engage inner surfaces 1727 of the securement elements 1726. When the upper central ring 1782 is mounted on the upper ring 1718U, the securement elements 1726 extend through the lumen 1719 of upper ring 1718 and into the guide structures 1786 such that inner surfaces 1727 of the securement elements 1726 at least partially engage the angled deployer surfaces 1775. This engagement occurs in both the undeployed position, as shown in FIG. 99A, and the deployed position, as shown in FIGS. 99 B and 99C.

The securement elements 1726 are formed of a resiliently flexible material and may be of unitary construction with the upper central ring 1782. The securement elements 1726 are moveable between an undeployed position in which the securement elements 1726 are at least partially recessed in the upper ring 1718U and a deployed position where the securement elements 1726 extend proximally and radially outward from the upper ring 1718U so that they are able to engage and secure to the wall of the bladder. The securement elements 1726 are moveable between the retracted and deployed positions by flexing due to engagement with the angled deployer surfaces 1775 of the guide structures 1786, as the upper central ring 1782 is moved in a proximal direction with respect to the upper ring 1718U. FIG. 99A shows the securement elements 1726 in the retracted position and FIG. 99B shows the securement elements 1726 in the deployed position. The arrow "B" in FIG. 99B illustrates the direction of motion of the securement elements 1726 during deployment, as the upper central ring 1782 is moved proximally, in the direction of arrow "A," with respect to the upper ring 1718U. The upper ring securement elements 1726 may pivot towards the deployed position on living hinges (not shown), or through the use of an actual hinge element (not shown) or via the inherent flexibility of the upper central ring 1782. Preferably, when in the deployed position, the securement elements 1726 have at least some sort of bias in the radial inward and proximal directions, to facilitate engagement and retainment of a vessel such as the bladder.

Alternatively, the securement elements 1726 may be physically locked or held in position. As shown in FIG. 97, the upper ring 1718U comprises ring mounting elements 1787 extending distally from the upper ring 1718U and defining locking elements 1788. The ring mounting elements 1787 may be adapted to extend into the central opening of the upper central ring 1782 and engage an inner surface of the upper central ring 1782 such that the locking elements 1788 engage a corresponding structure in the inner surface of the upper central ring 1782 by snap-fit engagement after the upper central ring 1782 is moved in a proximal direction to fully deploy the securement elements 1726. Thus, when the upper central ring 1782 is locked adjacent to the upper ring 1718U, it is positioned distally of the upper ring 1718U, further extending the central lumen 1719 of the upper ring 1718U. As seen in FIG. 99B, this extension of the central lumen 1719 provides a path for fluid to flow through after the anastomosis device is deployed within a patient. The ring mounting elements 1787 may also engage and lock the upper central ring 1782 by friction fit or other means.

Turning now to FIG. 98, lower ring 1716L is shown comprising a body that defines a central lumen 1717. The central lumen 1717 of the lower ring 1716L is adapted to receive the upper ring securement element deployer 1772 and a deployment shaft 1773 therethrough. The lower ring 1716L is provided with a lower central ring 1780 having securement elements 1724 extending axially therefrom, in the undeployed position. The securement elements 1724 are preferably formed from a resiliently flexible material and may be of unitary construction with the lower central ring 1780. The lower central ring 1780 may be mounted at the distal end of the lower ring 1716L, and may be at least partially disposed with an inner circumference defined by the lower ring 1716L. However, as one would appreciate from the embodiment shown in FIG. 91, the lower central ring 1780 may also be mounted on a proximal side of the lower ring 1716L upon appropriate alteration of the mechanisms for deployment.

Like the upper ring 1718U, the lower ring 1716L may comprise ring mounting elements defining one or more locking elements (not shown) that engage and lock the lower central ring 1780 in contact with the lower ring 1716L to hold securement elements 1724 in the deployed position. The locking elements may engage the lower central ring 1780 by snap-fit, friction fit or other means.

The body of the lower ring 1716L contains a plurality of axial slots 1785 defined by a plurality of axially extending members 1784 located on the distal end of the lower ring 1716L. The axial slots 1785 are sized and positioned to engage with and receive a portion of securement elements 1724. In an undeployed position, the lower central ring 1780 is spaced distally from the lower ring 1716L, such that the securement elements 1724 reside within the axial slots 1785 of the lower ring 1716L. FIG. 99A shows the securement elements 1724 extending into the axial slots 1785 of the lower ring 1716L when the central ring 1780 is mounted on the lower ring 1716L. The axial slots 1785 are provided with angled deployer surfaces 1747 that engage the curved inner surfaces 1725 of the securement elements 1724 during operation of the device 1712.

Similar to the upper securement elements 1726, the lower securement elements 1724 are moveable between an undeployed position where they are at least partially recessed into the lower ring body 1716 and a deployed/extended position in which the securement elements 1724 extend outward from the lower ring 1716L so that the securement elements 1724 engage and secure to the wall of the urethra. The curved inner surface 1725 of the securement elements 1724 engages with the deployer surfaces 1747 of axial slots 1785, thus urging and flexing the securement elements 1724 radially outward when the central ring 1780 is moved in a proximal direction with respect to the lower ring 1716L. Additionally or alternatively, the lower ring securement elements 1724 may pivot towards the deployed position on living hinges 1723. Arrow "C" in FIG. 99B illustrates the movement of the securement elements 1724 towards a deployed position. Preferably, when in the deployed position, the securement elements 1724 have at least some sort of bias in the radial inward and distal directions, to facilitate engagement and retainment of a vessel such as the urethra. Alternatively, the securement elements 1724 may be physically locked or held in position.

As shown in FIGS. 97 and 98, the upper and lower assemblies 1718, 1716 also comprise interconnecting elements 1730 and 1728, respectively, for coupling the rings together. The interconnecting elements 1728 and 1730 may be similar to the connector elements 28 and 30 of rings 16 and 18. As shown, the upper interconnecting elements 1730 comprise an extending member with an engagement surface 1731 adapted to engage the lower interconnecting elements 1728, which define an opening in the body of the lower ring 1716, by snap fit connection.

Figure 94:
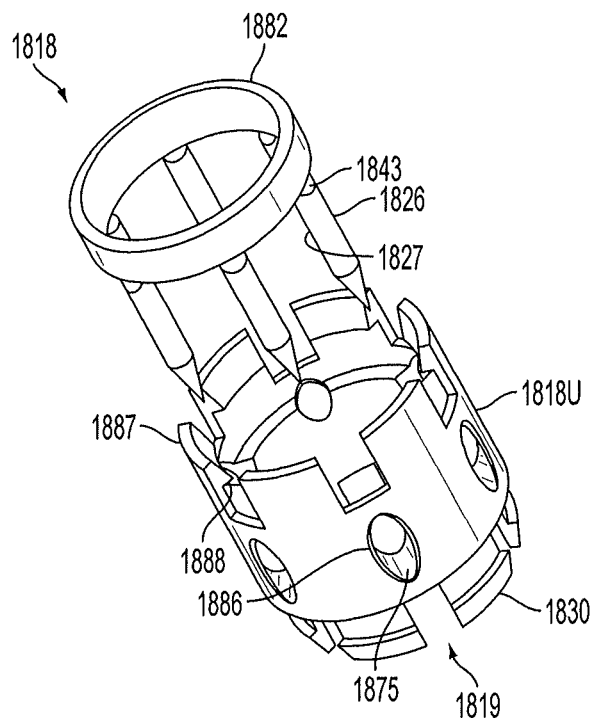
FIG. 94 is a perspective view of a further alternative embodiment of an upper coupling part.
Figure 95:
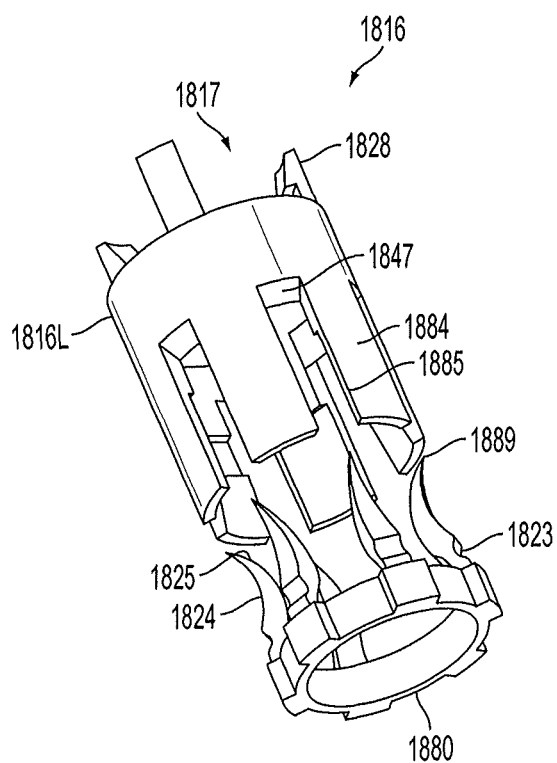
FIG. 95 is a perspective view of a further alternative embodiment of a lower coupling part.

FIGS. 94 and 95 show a further alternative embodiment of a ring assembly 1814 comprising a lower ring assembly 1816 and upper ring assembly 1818. The upper and lower ring assemblies 1818, 1816 are structurally similar to ring assemblies 1718 and 1716 shown in FIGS. 97 and 98. For example, each ring assembly comprises a central ring 1880, 1882 on which the lower and upper securement elements 1824, 1826 are mounted and interconnecting elements 1828, 1830 for coupling the ring assemblies together. The securement elements of upper and lower ring assemblies 1818, 1816 may be deployed by similar mechanism and instrument as lower and upper ring assemblies 1716, 1718. However, the upper ring assembly 1818 differs from upper ring assembly 1718 of FIG. 97 in that the ring mounting elements 1887 define one or more resiliently flexible ring mounting elements 1887 and locking elements 1888 that engage and lock the outer surfaces of the upper central ring 1882. Thus, when the upper central ring is locked in contact with the upper ring 1818U, it is received within the lumen 1819 of the upper ring 1818U. As shown, the locking elements 1888 engage the upper central ring 1882 through a snap-fit connection after the upper central ring 1882 is moved in a proximal direction to fully deploy the securement elements 1826. The locking elements 1888 may also engage and lock the upper central ring 1882 by friction fit or other means.

Turning now to FIGS. 99A-99C, the deployment operation of a ring assembly 1714 will be discussed. During deployment of the ring assembly 1714, the lower central ring 1780 is mounted distally with respect to the lower ring 1716L. As shown in FIGS. 99A and 99B, the upper ring assembly 1718 is mounted on the distal end of surgical instrument 1712, adjacent the upper ring securement element deployer 1772, and distally of the deployment shaft 1773 with the upper central ring 1782 mounted on distal side of the upper ring 1718.

As shown in FIGS. 99A and 99B, the securement elements 1726 of upper ring 1718U are deployed by axial retraction of the upper ring securement element deployer 1772 with respect to the upper ring 1718U, which carries with upper central ring 1782 proximally and urges inner surfaces 1727 of the securement elements 1726 against deployer surfaces 1775 of the guide structures 1786 of the upper ring 1718U. In FIG. 99B, the direction of axial movement of the upper ring securement element deployer 1772 is shown by arrow "A" and the resulting deployment of the securement elements 1726 by radial extension is shown by arrow "B."

As shown in FIGS. 99A and 99B, the securement elements 1724 of the lower ring assembly 1716 are deployed by axial movement of the lower central ring 1780 in a proximal direction with respect to the lower ring 1716L. Axial movement of the lower central ring 1780 in the proximal direction with respect to the lower ring 1716L can be achieved by mounting the lower ring 1716L proximally with respect to the lower ring securement element deployer (not shown) with the distal surface of the central ring 1780 in engagement with the lower ring securement element deployer. With this arrangement, axial retraction of the lower ring securement element deployer with respect to the lower ring 1716L urges the lower central ring 1780 to move proximally with respect to the lower ring 1716L. The securement elements 1724 are moved towards the deployed position when the inner surfaces 1725 of the securement elements 1724 are urged against the deployer surface 1747 of the lower ring 1716L. As shown, the securement elements 1724 are also curved and the curvature of the securement elements 1724 causes the piercing tips 1789 to follow an arced path, as indicated by arrow "C" in FIG. 99B, when the inner surfaces 1725 are urged against the deployer surfaces 1747 of the lower ring 1716L.

Deployment of the upper and lower securement elements 1726, 1724, through operation of the device (as shown between FIGS. 99A and 99B) will preferably result in engagement of vessel tissue, such as engagement of the bladder neck with the upper securement elements 1726 and engagement of the urethra with the lower securement elements 1724. Once the vessel tissue is engaged, the upper ring assembly 1718 and lower ring assembly 1716 are retracted towards each other until the interconnecting elements 1728, 1730 engage each other, thereby retaining the upper and lower ring assemblies 1716, 1718 together and securing the anastomosis of the vessels. The retracted upper and lower ring assemblies 1716, 1718 are illustrated in FIG. 99C.

Figure 84:
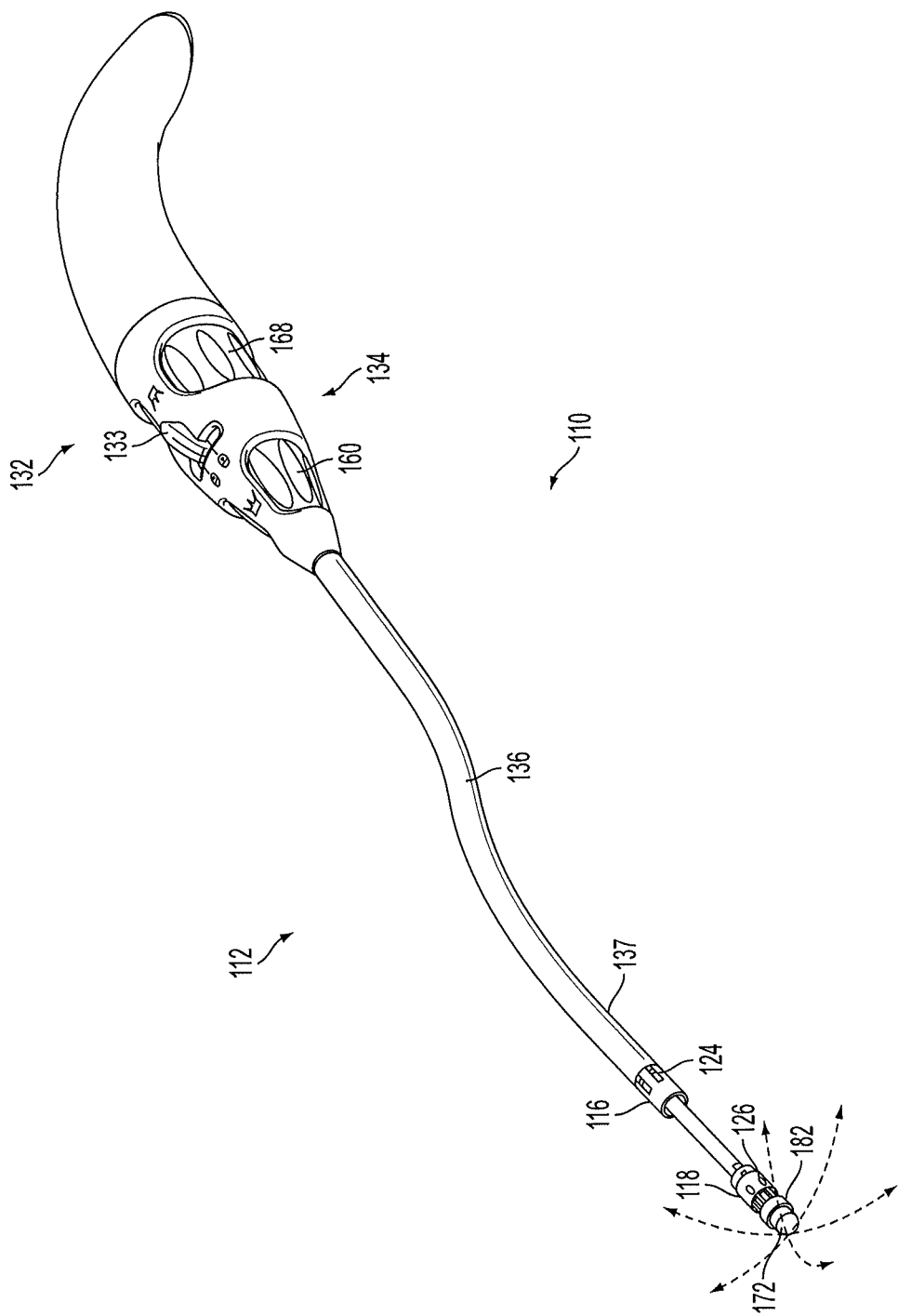
FIG. 84 is a side view of a further alternative embodiment of an assembled anastomosis system.
Figure 85:
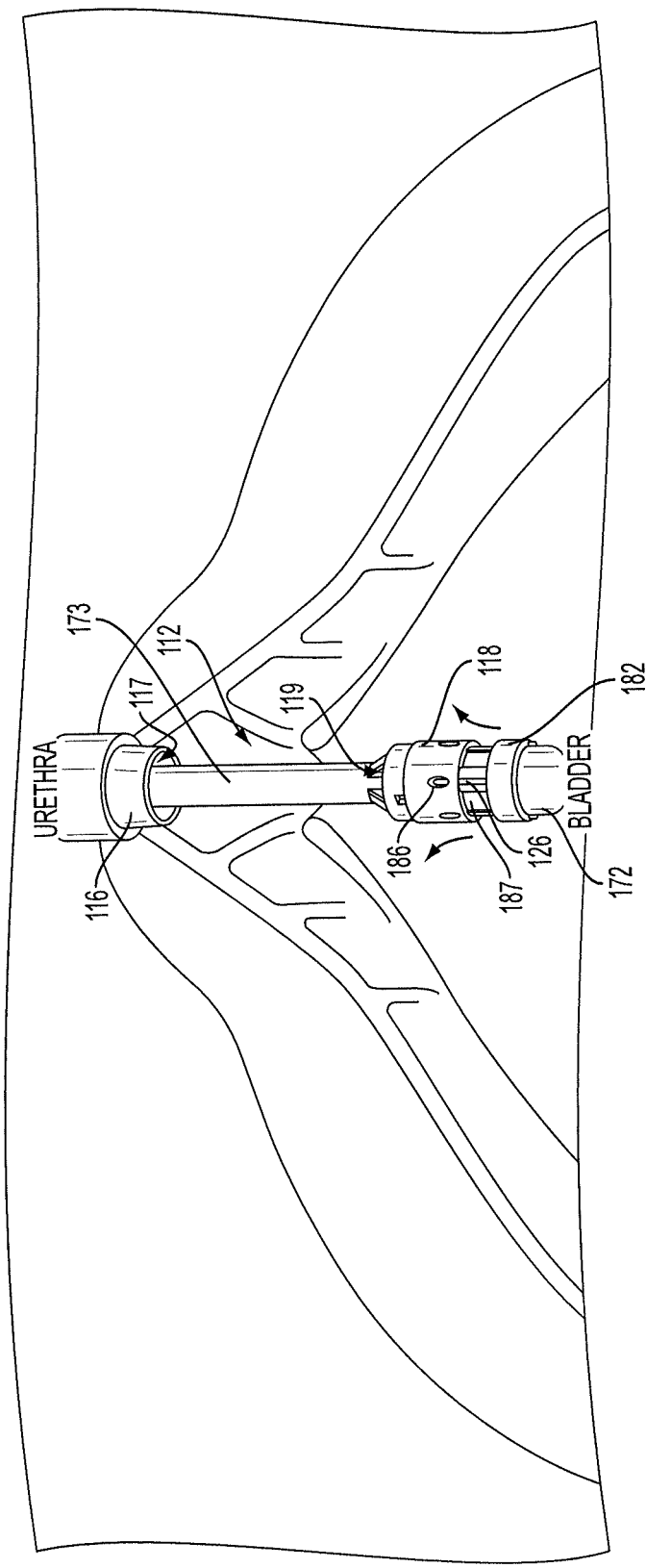
FIG. 85 is a perspective view of a portion of the anastomosis system depicted in FIG. 84 showing an upper coupling part with securement elements in the undeployed position.

Referring generally to FIGS. 84 to 93 and 96, an alternate structure of a ring assembly 114 and its method of deployment will now be described. First, the structural details of the alternative embodiment of the ring assembly 114 and upper and lower rings 118, 116 are depicted in FIGS. 85-93. As shown in FIG. 85, the upper ring 118 comprising a body that defines a central lumen 119. The central lumen 119 is adapted to receive the upper ring securement element deployer 172 and a deployment shaft 173 therethrough. The upper ring 118 is provided with an upper central ring 182 having securement elements 126 extending axially therefrom, in the undeployed position, as shown in FIG. 85. The securement elements 126 are preferably formed from a resiliently flexible material and may be of unitary construction with the upper central ring 182. The upper central ring 182 is mounted at the proximal end of the upper ring 118, and may be mounted near ring mounting elements 187.

Figure 93:
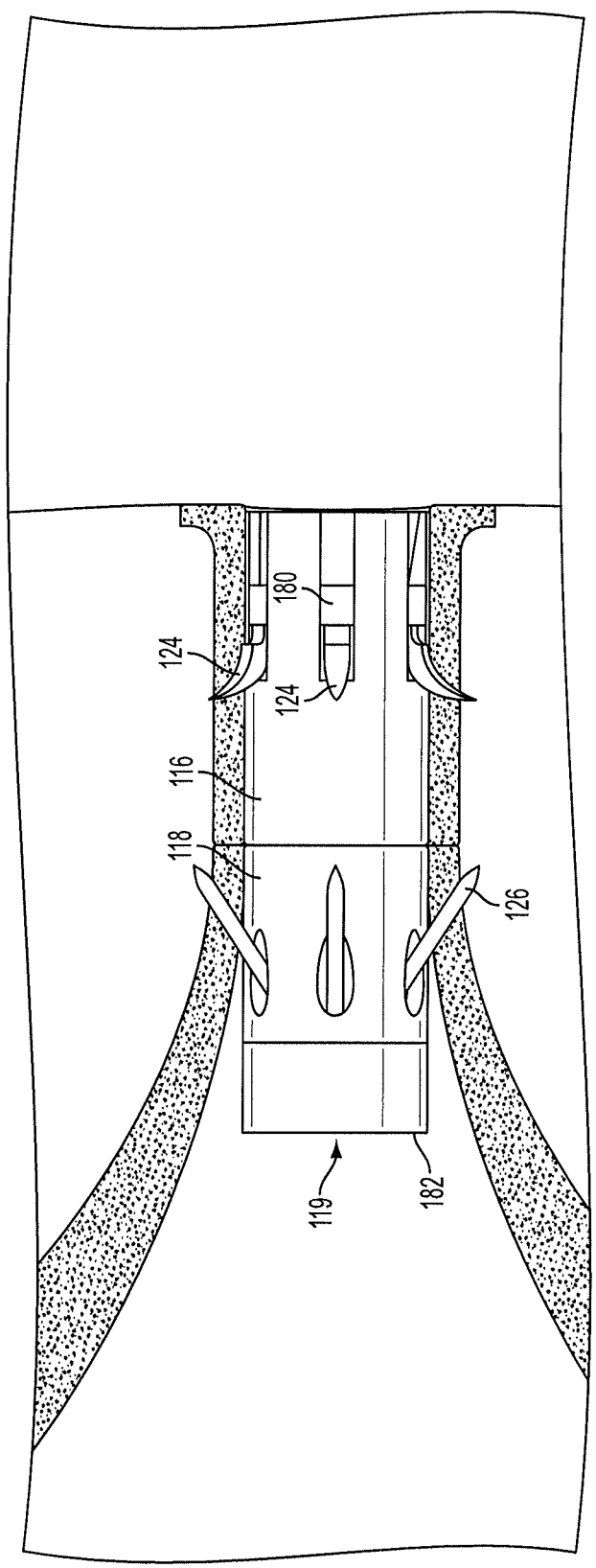
FIG. 93 is a side view of a portion of the anastomosis system showing the ring assembly depicted in FIG. 84 installed in the bladder neck and urethra neck of a patient.

The ring mounting elements 187 of the upper ring 118 may define one or more locking elements (not shown) that engage and lock the upper central ring 182 in contact with the upper ring 118 to hold securement elements 126 in the deployed position. As shown, the locking elements extend distally from the upper ring 118 into the central of the upper central ring 182 to engage an inner surface of the upper center ring 182 by snap-fit engagement after the upper central ring 182 is moved in a proximal direction to fully deploy the securement elements 126. Thus, when the upper central ring 182 is locked adjacent to the upper ring 118, it is positioned distally of the upper ring 118, further extending the central lumen 119 of the upper ring 118. As seen in FIG. 93, this extension of the central lumen 119 provides a path for fluid to flow through after the anastomosis device is deployed within a patient. The ring mounting elements 187 may also engage and lock the upper central ring 182 by friction fit or other means.

Figure 91:
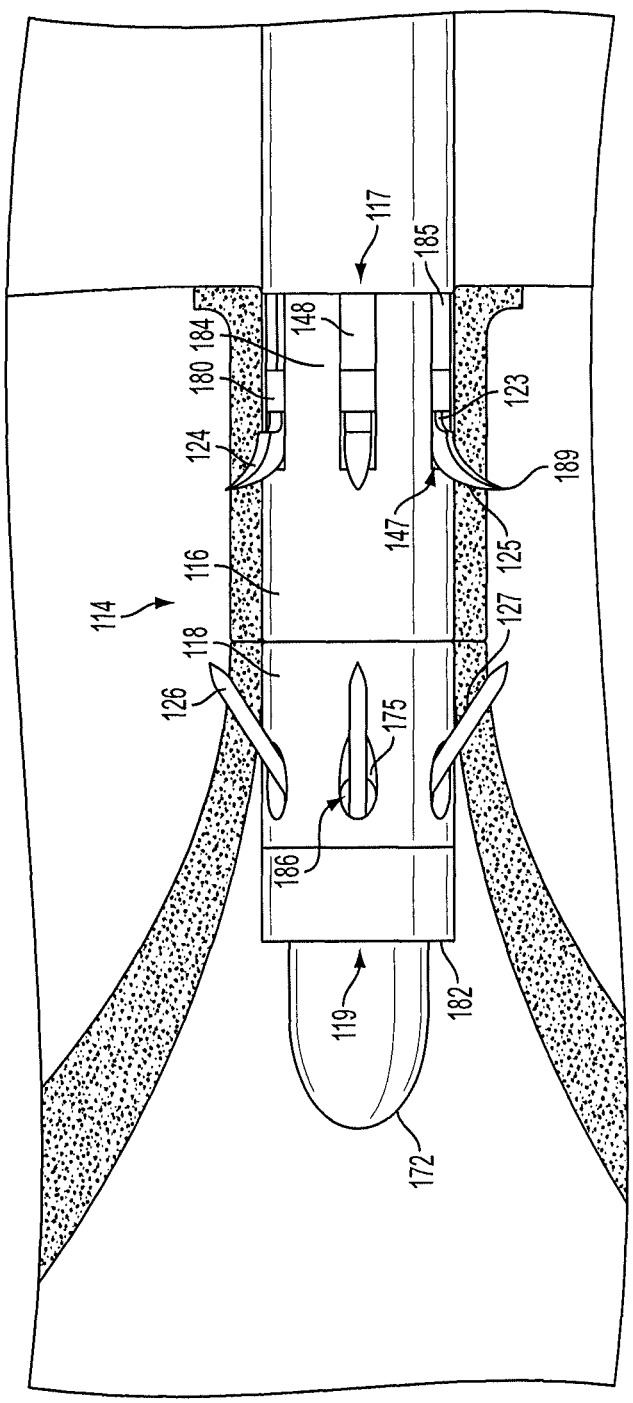
FIG. 91 is a side view of a portion of the anastomosis system showing the ring assembly installed in the bladder neck and urethra neck of a patient and mounted on the anastomosis system depicted in FIG. 84.
Figure 92:
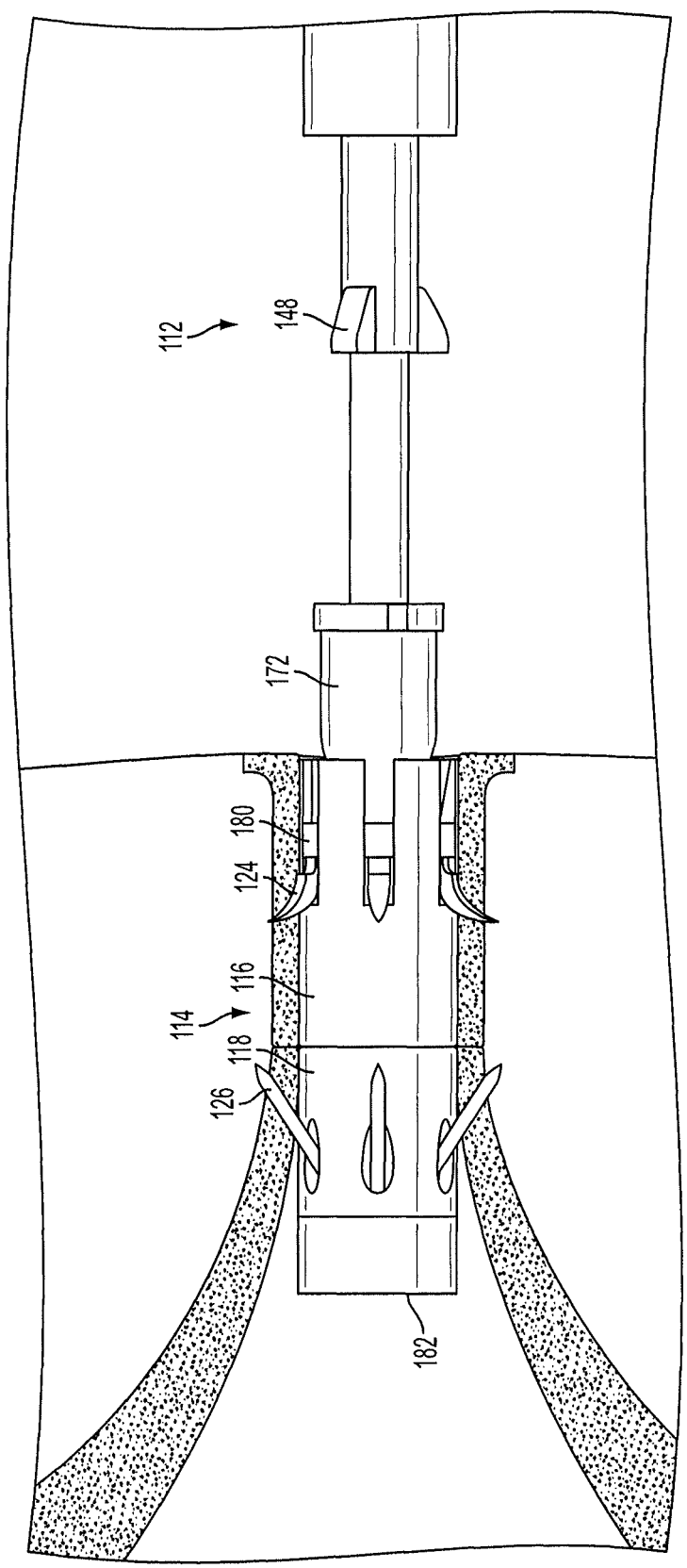
FIG. 92 is a side view of a portion of the anastomosis system showing the ring assembly depicted in FIG. 84 installed in the bladder neck and urethra neck of a patient and the anastomosis system depicted in FIG. 84.

Referring now to FIG. 91, the body of the upper ring 118 defines a plurality of guide structures 186, which extend through the circumferential wall of the upper ring 118. As shown, the guide structures 186 comprise openings in the sidewall of the body of the upper ring 118 that are sized and positioned to permit passage of securement elements 126 therethrough, in a proximal and radially outward direction. As best seen in FIG. 91, the guide structures 186 have angled deployer surfaces 175 adapted to engage inner surfaces 127 of the securement elements 126. When the central ring 182 is mounted on the upper ring 118, the securement elements 126 extend through the lumen 119 of upper ring 118 and into the guide structures 186 such that inner surfaces 127 of the securement elements 126 engage the angled deployer surfaces 175. This engagement occurs in both the undeployed position, as shown in FIG. 85, and the deployed position, as shown in FIGS. 91 and 92.

Figure 86:
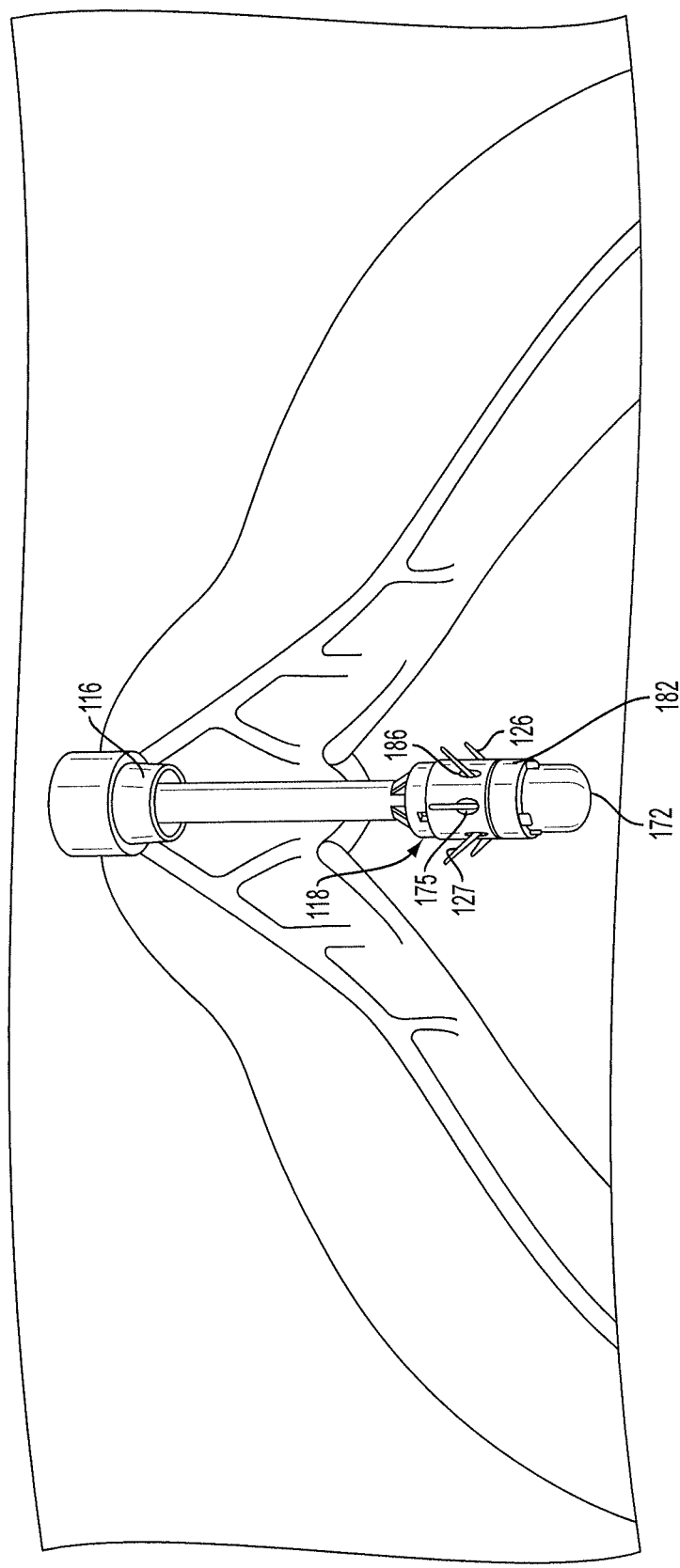
FIG. 86 is a perspective view of a portion of the anastomosis system depicted in FIG. 84 showing an upper coupling part with securement elements in the deployed position

The securement elements 126 are formed of a resiliently flexible material and may be of unitary construction with the central ring 182. The securement elements 126 are moveable between an undeployed position in which the securement elements 126 are at least partially recessed in the upper ring body 118 and a deployed position where the securement elements 126 extend proximally and radially outward from the upper ring body 118 so that they are able to engage and secure to the wall of the bladder. The securement elements 126 are moveable between the retracted and deployed positions by flexing due to engagement with the angled deployer surfaces 175 of the guide structures 186, as the upper central ring 182 is moved in a proximal direction with respect to the upper ring 118. FIG. 85 shows the securement elements 126 in the retracted position and FIG. 86 shows the securement elements 126 in the deployed position. The arrows in FIG. 85 illustrate the direction of motion of the securement elements 126 during deployment. The upper ring securement elements 126 may pivot towards the deployed position on living hinges 183, such as shown in FIG. 85, or through the use of an actual hinge element (not shown) or via the inherent flexibility of the securement elements 126. Preferably, when in the deployed position, the securement elements 126 have at least some sort of bias in the radial inward and proximal directions, to facilitate engagement and retainment of a vessel such as the bladder. Alternatively, the securement elements 126 may be physically locked or held in position.

Figure 87:
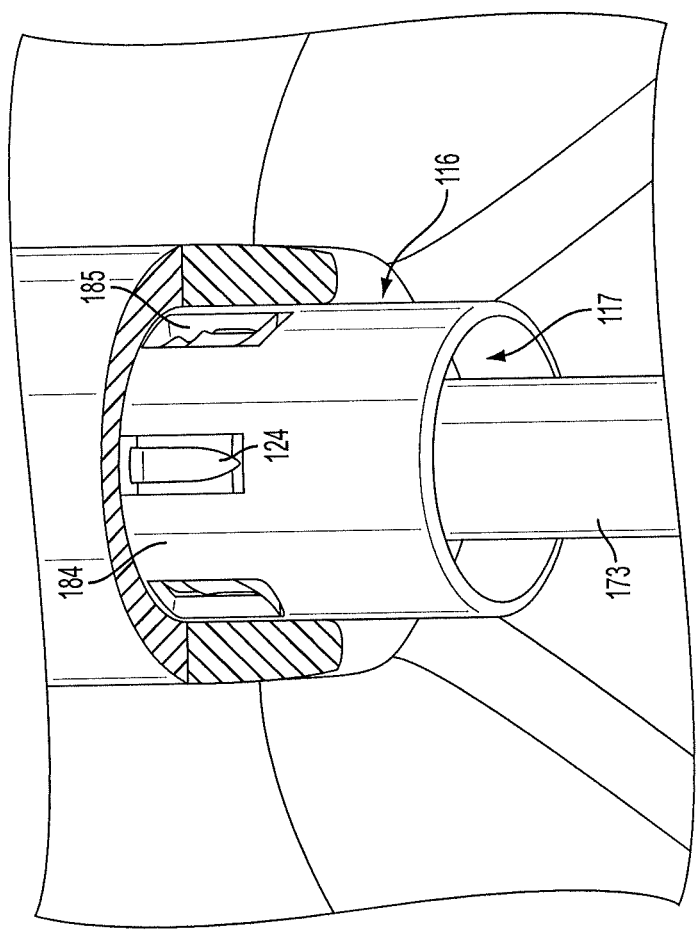
FIG. 87 is a perspective view of a portion of the anastomosis system depicted in FIG. 84 showing a lower coupling part with securement elements in the undeployed position.

Turning to FIGS. 87-91, a lower ring 116 comprising a body that defines a central lumen 117 is shown. The central lumen 117 of the lower ring 116 is adapted to receive the upper ring securement element deployer 172 and a deployment shaft 173 therethrough. The lower ring 116 is provided with a lower central ring 180 (see FIG. 91) having securement elements 124 extending axially therefrom, in the undeployed position, as shown in FIG. 87. The securement elements 124 are preferably formed from a resiliently flexible material and may be of unitary construction with the lower central ring 180. The lower central ring 180 is mounted at the proximal end of the lower ring 116, and may be at least partially disposed with an inner circumference defined by the lower ring 116.

Like the upper ring 118, the lower ring 116 may comprise ring mounting elements defining one or more locking elements (not shown) that engage and lock the lower central ring 180 in contact with the lower ring 116 to hold securement elements 124 in the deployed position. The locking elements may engage the lower central ring 180 by snap-fit, friction fit or other means.

The body of the lower ring 116 contains a plurality of axial slots 185 defined by a plurality of axially extending members 184 located on the proximal end of the lower ring 116. The axial slots 185 are sized and positioned to engage with and receive a portion of securement elements 124. In an undeployed position, the lower central ring 180 is spaced proximally from the lower ring 116, such that the securement elements 124 reside within the axial slots 185 in the lower ring 116. FIG. 91 shows the securement elements 124 extending into the axial slots 185 of the lower ring 116 when the central ring 180 is mounted on the lower ring 116. The axial slots 185 are provided with angled deployer surfaces 147 that engage the curved inner surfaces 125 of the securement elements 124 during operation of the device 112.

Figure 88:
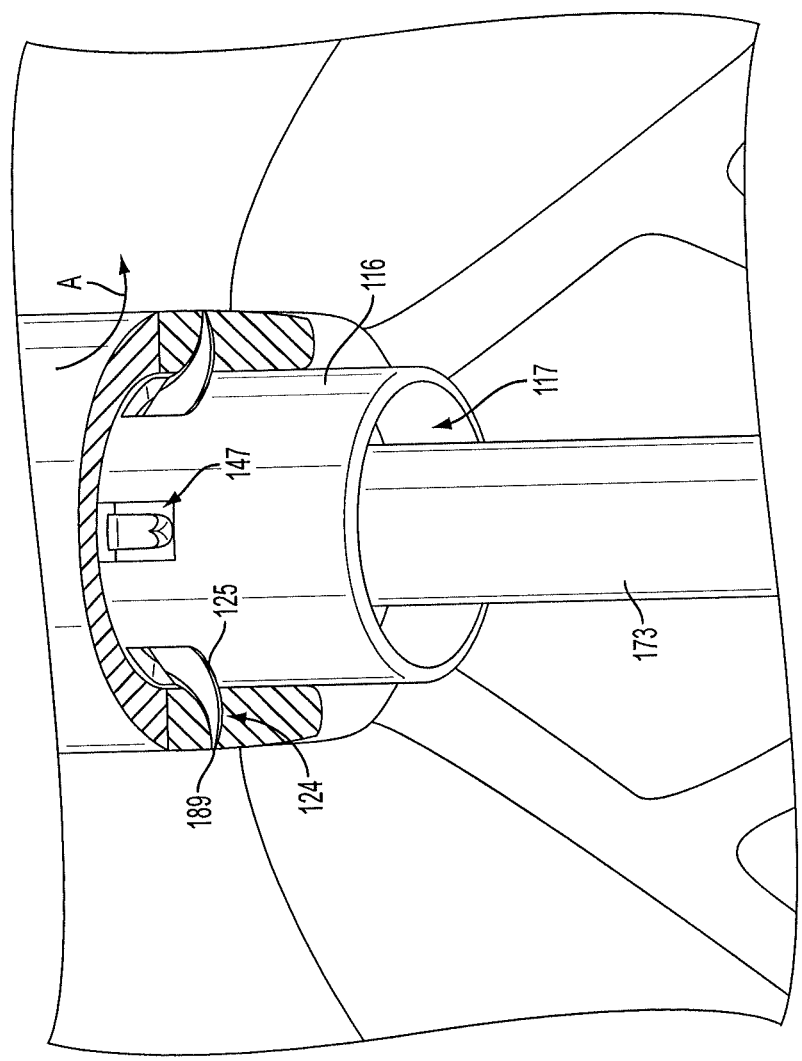
FIG. 88 is a perspective view of a portion of the anastomosis system depicted in FIG. 84 showing a lower coupling part with securement elements in the deployed position.

Similar to the upper securement elements 126, the lower securement elements 124 are moveable between an undeployed position where they are at least partially recessed into the lower ring body 116 and a deployed/extended position in which the securement elements 124 extend outward from the lower ring body 116 so that the securement elements 124 engage and secure to the wall of the urethra. The curved inner surface 125 of the securement elements 124 engages with the deployer surfaces 147 of axial slots 185, thus flexing the securement elements 124 radially outward when the central ring 180 is moved in a distal direction with respect to the lower ring 116. Additionally or alternatively, the lower ring securement elements 124 may pivot towards the deployed position on living hinges 123. Arrow "A" shown in FIG. 88 illustrate the movement of the securement elements 124 towards a deployed position. Preferably, when in the deployed position, the securement elements 124 have at least some sort of bias in the radially inward and distal directions, to facilitate engagement and retainment of a vessel such as the urethra. Alternatively, the securement elements 126 may be physically locked or held in position.

In the assembled anastomosis system shown best in FIGS. 85 and 91, the upper ring 118 and the lower ring 116 are mounted on the surgical instrument 112 with the upper ring securement element deployer 172 and deployment shaft 173 extending through the center of the upper and lower rings 118, 116. The upper ring 118 is positioned distally from the lower ring 116. As best seen in FIG. 91, the upper central ring 182 is retained on the distal side of the upper ring 118 and, and the lower central ring 180 is retained within the proximal portion of the lower ring 116. The upper ring securement element deployer 172 engages the distal surface of the upper central ring 182 of the upper ring 118.

Figure 96:
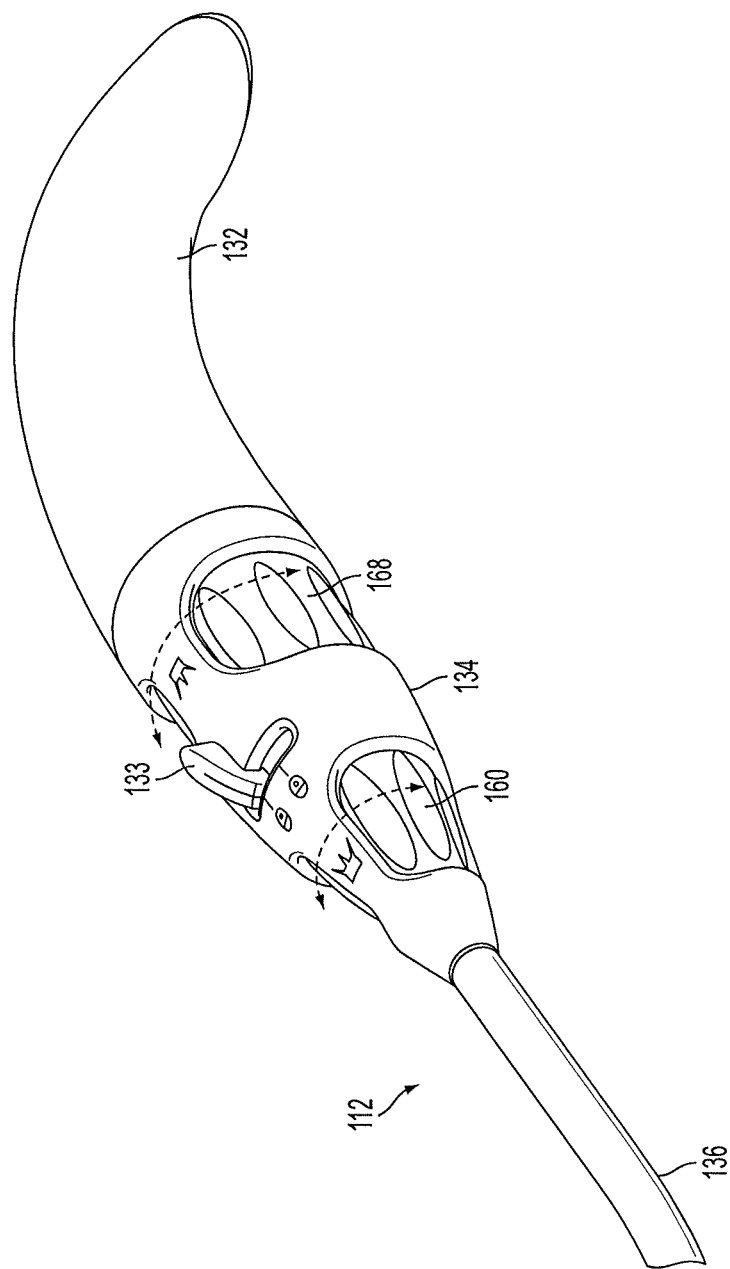
FIG. 96 is a perspective view of the handle assembly of the surgical instrument depicted in FIG. 84.

The method of delivering and implanting a ring assembly 114 similar to the ring assemblies shown in FIGS. 94, 95 and 97-99c is now discussed. FIGS. 84 and 96, depict an alternative embodiment of a surgical instrument 112, which includes a handle assembly 132, grip member 134, handle tube 136, upper tube 137, and the upper ring securement element deployer 172. The handle assembly 132 comprises first and second knobs 160, 168. The first knob 160 operates to deploy the securement elements 124 of the lower ring 116 and the second knob 168 operates to deploy the securement elements 126 of the upper ring 118. Arrows in FIG. 96 illustrate the rotational motion of the knobs 160 and 168. The surgical instrument 112 may comprise a rotary-translatory motion converter, such as the rotary bearing 58 of previously described surgical instrument 12, that converts rotational motion of knobs 160 and/or 168 to axial motion of the deployer mechanisms in either or both the proximal and distal directions. Additionally, the handle assembly 132 includes a release switch 133 which, like locking ring 33 of the previously described surgical instrument 12, operates to release the ring assembly 114 from the surgical instrument 112 after emplacement similar to the previously described embodiments. The handle tube 136 is preferably flexible, with a 360° range of motion, as indicated by arrows in FIG. 84. The flexibility assists in insertion of the surgical instrument 112 through the urethra and can accommodate the naturally curved pathways of the patient's anatomy.

As shown in FIG. 84, a ring assembly 114 comprising a lower ring 116 and upper ring 118 is mounted on the distal end of the surgical instrument 112 with the upper ring securement element deployer 172 passing through the lower and upper rings 116, 118, in the undeployed position. The upper ring 118 is mounted on the distal end of surgical instrument 112 (shown in FIGS. 84 and 96) with an upper central ring 182 mounted on the distal side of the upper ring 118. The lower ring 116 is mounted on the surgical instrument 112 proximally with respect to upper ring 118. The lower ring 116 is mounted on the surgical instrument 112 with a lower central ring 180 positioned on the proximal side of the lower ring 116 (best seen in FIG. 91). However, the surgical instrument 112 can be adapted to deliver and deploy lower rings having distally mounted lower central rings by altering the position and direction of movement of the deployer mechanism (see e.g. FIGS. 99A-99C). The upper ring 118 and lower ring 116 may be provided with interconnecting elements (not shown) similar to those described in previous embodiments for coupling the rings together, thereby joining vessel portions together in anastomosis.

Referring now to FIGS. 85 and 86, during operation the upper ring 118 is positioned within a cavity, such as the bladder. The securement elements 126 are deployed by axial retraction of the upper ring securement element deployer 172 in a proximal direction with respect to the upper ring 118. The upper ring securement element deployer 172 may be axially retracted by rotating the knob 168 of surgical instrument 112 with respect to the handle assembly 132, shown in FIG. 96. When the upper ring securement element deployer 172 axially retracts with respect to the upper ring 118, the upper ring securement element deployer 172 urges the upper central ring 182 in a proximal direction with respect to the upper ring 118. As the upper central ring 182 is moved in a proximal direction with respect to the upper ring 118, the inner surfaces 127 of the securement elements 126 are urged towards engagement with the angled deployer surfaces 175 of the guide structures 186 of the upper ring 118 (similar to the operation of the embodiments described above with respect to FIGS. 97-98).

As shown in FIG. 86, engagement of the inner surfaces 127 of the securement elements 126 with the angled deployer surfaces 175 deploys the securement elements 126 by forcing the securement elements 126 to flex and deflect radially outward from the upper ring 118, through the guide structures 186 of the upper ring 118. As discussed above, ring mounting elements 187 may lock and secure the upper central ring 182 to hold the securement elements 126 in the deployed position. To engage the vessel tissue, the upper ring 118 is moved in a proximal direction such that the securement elements 126 engage and/or pierce the vessel, as a result of the radially outward and proximal extension of the securement elements 126 and their radial inward and proximal bias (see e.g. FIG. 89 for engagement of the securement elements 126 with tissue).

After the upper ring 118 engages a vessel, such as the bladder neck, the lower ring 116 may be secured to an opposing vessel, such as the urethra neck, as follows. Turning now to FIG. 87, the lower ring 116, with securement elements 124 in the retracted position, is positioned within the urethra neck. The securement elements 124 may be deployed by turning knob 160 with respect to the handle assembly 132 to axially extend the lower ring securement element deployer 148, as shown in FIGS. 84 and 96. As best understood from FIG. 91, when the lower ring securement element deployer 148 axially extends in a distal direction with respect to the lower ring 116, the lower ring securement element deployer 148 urges the lower central ring 180 to move in a distal direction with respect to the lower ring 116. Axial movement of the lower central ring 180 in a distal direction with respect to the lower ring 116 urges the securement elements 124 to move distally though the axial slots 185 until the inner surfaces 125 of the securement elements 124 engage the deployer surfaces 147 of the lower ring body 116. Continued axial movement of the lower central ring 180 with respect to the lower ring 116 forces the securement elements 124 against the deployer surfaces 147 and urges the securement elements 124 to flex and/or deflect radially outward from the lower ring 116.

As shown, the inner surfaces 125 of the securement elements 124 are curved. Due to the curvature of the securement elements 124, the piercing tips 189 of the securement elements 124 follow an arched path in a generally radially outward direction with respect to the lower ring 116. The length and angle of the path of the piercing tip 189 may depend on the curvature of the securement element 124. As shown in FIG. 88, the securement elements 124 follow the path indicated by the arrow "A" when deployed to extend radially outward from the lower ring body 116 to engage the urethra.

Figure 89:
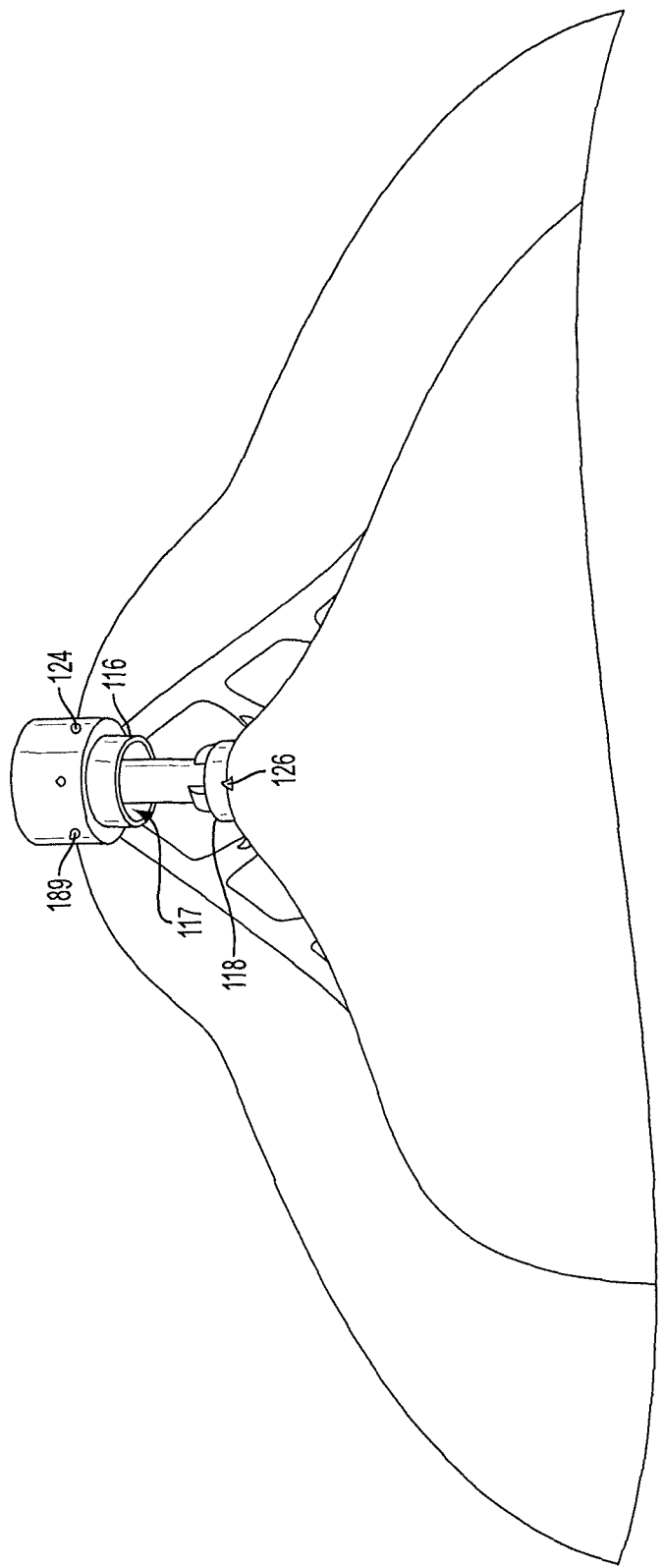
FIG. 89 is a perspective view of a portion of the anastomosis system depicted in FIG. 84 showing securement elements of an upper coupling part and lower coupling part engaged with bladder and urethra.

FIG. 89 shows an external view of the securement elements 124, 126 of the lower and upper rings 116, 118 after deployment and the engagement with the urethra and bladder tissue by piercing the vessel tissue. As shown, after engaging the respective vessels, the upper ring 118 is moved into proximity with the lower ring 116, thereby drawing the bladder and urethra necks closer together.

An exemplary method of drawing the lower and upper rings together may include grasping knob 168 and shifting it proximally with respect to the grip member 134. Upon proximal shifting, the knob 168 engages a separate mechanism in the surgical instrument 112 (not shown) that permits rotation of the knob 168 to rotate a threaded element (not shown) flexibly linked to the upper securement element deployer 172, thereby allowing the upper securement element deployer 172 to be moved proximally and/or distally in relation to the lower ring 116. Alternatively, further rotation of the first knob 160 (after deployment of the securement elements 124, 126, may retract the upper securement element deployer 172, thereby drawing the upper ring 118 towards the lower ring 116. Alternatively, a lever mechanism (not shown) may be included in the end of handle 132 and may be extended and used to move the upper securement element deployer 172 proximally and/or distally in relation to the lower ring 116. In a further alternative method, the surgical instrument 112 can be provided with a third knob (not shown) on the proximal end of the handle assembly 132 that may be pulled proximally with respect the handle assembly 132. Once the knob is proximally pulled, a portion of the knob can engage a threaded element (not shown) connected to the upper securement element deployer 172 such that, when the knob is rotated, it draws the upper securement element deployer 172 proximally and/or distally in relation to the lower ring 116.

Figure 90:
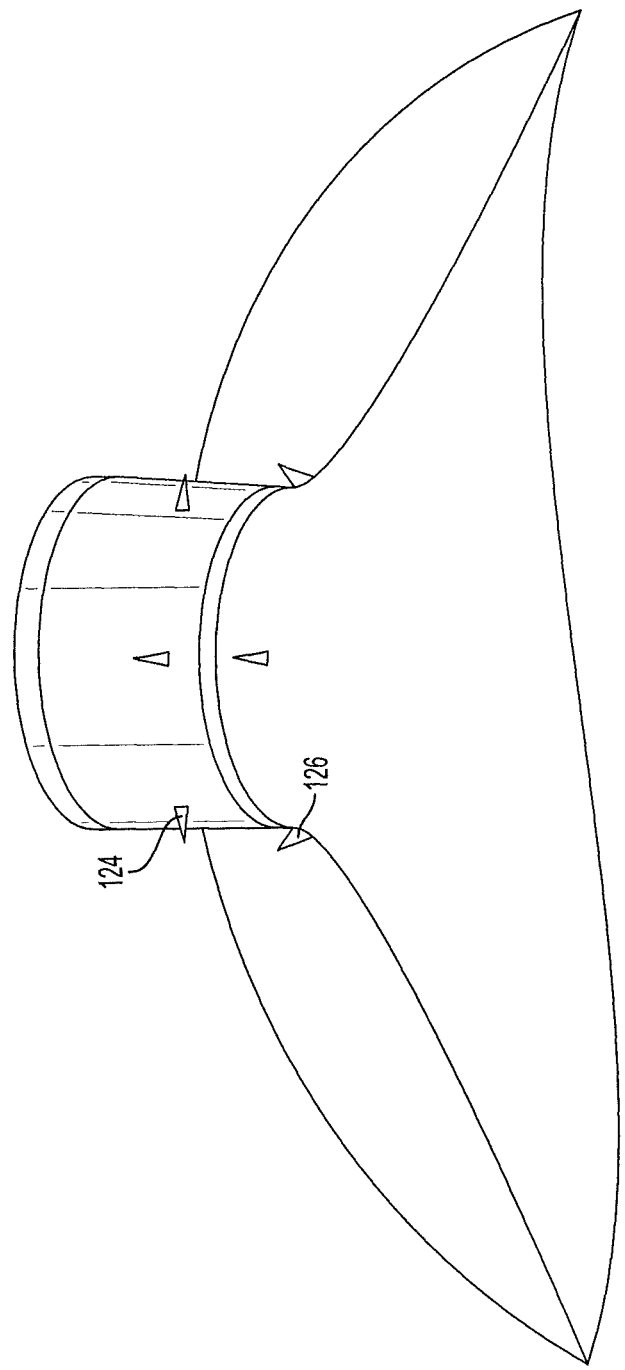
FIG. 90 is a perspective view of anastomosis of the bladder and urethra by upper coupling part and lower coupling part of the anastomosis system depicted in FIG. 84.

As shown in FIGS. 90 and 91, the lower and upper rings 116, 118 are brought into contact and are coupled together, thereby forming an anastomosis of the bladder and urethra. Although FIGS. 85-93 do not show the upper and lower rings 118,116 comprising interconnecting elements, the rings can be provided with coupling mechanisms as described with respect to the previously discussed ring assembly 14 shown in FIG. 3, snap fit elements as shown in FIGS. 94, 95, or grooves (not shown) provided on an inner luminal surface of the rings 116 and 118 that engage the respective upper and lower central rings 182, 180 when the rings are moved to deploy the securement elements.

As shown in FIG. 92, the ring assembly 114 may be released from the surgical instrument 112 after the upper ring 118 and lower ring 116 are coupled together. The ring assembly 114 is released by depressing release switch 133. As shown, release switch 133 comprises a safety type mechanism that prevents inadvertent triggering by requiring a two-step action, such as depression of the release switch 133 and urging the release switch 133 in a direction transverse to the handle assembly. In one example, release switch 133 may actuate a cam-type mechanism that releases the ring assembly 114.

Referring now to FIG. 93, when the upper and lower rings 118, 116 are coupled together with the securement elements 126 and 124 deployed, preferable, the vessel tissue is retained in place and allowed to heal. The upper securement elements 126 are oriented to extend in a radial outward and proximal direction from the upper ring 118, thereby extending into the vessel tissue, such as a bladder neck, at an angle in a general direction towards the opposing vessel. Likewise, the lower securement elements 124 extend radially outward, and generally distally into an opposing vessel tissue, such as the urethra. The general direction that the securement elements 126, 124 extend into the respective vessel parts is opposite to the direction of movement that would separate the opposing vessels, and separate the anastomosis. As a result, any tension on the vessel tissue in a direction away from the opposing vessel tissue, or vice versa, serves to further embed the securement elements 126, 124 in the vessel tissue, thereby securing the anastomosis. After deployment and securement of the ring assembly, the surgical instrument 112 may be withdrawn from the urethra leaving the ring assembly 114 in place.

The preferred materials for the ring assembly 14 are now discussed. However, it will be understood that this discussion of materials can apply equally to all embodiments disclosed and contemplated herein. The ring assembly 14 is preferably formed of materials that are compatible with the environment (e.g. range of pH, variable constituents of urine and variable flow). The entirety of the ring assembly 14 may be formed from resorbable material(s) or at least a portion of the assembly may be formed from permanent material(s). Alternatively, one or more portions of the ring assembly 14 may be formed of resorbable material(s) while one or more other portions are formed from permanent material(s). In some embodiments, the securement elements 24 and 26, in particular, are formed from resorbable material, whereas other portions are formed from permanent materials. In some examples, a ring assembly 14 can be formed with a resorbable element that connects two non-resorbable elements and breaks down to permit the ejection of the permanent elements in the urine stream. In other examples, portions of the ring assembly may be formed from mixtures of different resorbable materials and/or different permanent materials.

As used herein, "permanent materials" refers to materials that are not expected to undergo dramatic changes in strength or composition during the period of time that the ring assembly 14 is needed to allow healing of tissues and the establishment of a tissue-based channel for urine flow. Permanent materials include, but are not limited to, polymeric materials or metals. Examples of permanent polymeric materials include PEEK, polyethylene, polypropylene and others currently used in medical devices both in the United States and worldwide. Permanent metals include those used in surgery such as, but not limited to, stainless steel and titanium, both in a range of compositions and alloys.

As used herein, "resorbable materials" refers to materials that exhibit the ability to change over time, such as breaking down and eventually being eliminated from the body of the patient. Resorbable materials include, but are not limited to, bioabsorbable and biodegradable materials. Preferably, Resorbable materials may be used as elements of implantable devices where over a period of time the implant breaks up and is absorbed, shed, or ejected from the body.

Resorbable materials are well known in the literature. See, Principles of Tissue Engineering (Lanza and Vacanti, eds., Elsevier Academic Press 3d ed. 2007) (1997). Suitable resorbable materials include, but are not limited to, homopolymers and co-polymer blends from families including polylactic acid, polyglcolic acid, ϵ-caprolactone, and trimethylene carbonate. Other resorbable polymers may include polyphosphazenes, polydioxanones, polyanhydrides and polyurethane materials. Additionally, materials based on naturally occurring substances including, but not limited to polyhydroxyalkanoates, chitin and its derivatives, cellulose and certain other starches that can be fabricated to useful forms may be used. Additionally, suitable resorbable materials may comprise metals, such as magnesium, that can be broken down by the body when used as an implantable device.

Additionally, the ring assembly may be formed from ceramics, such as calcium phosphate and hydroxyapatite based ceramics. By way of background, see e.g., Biomaterials Science: An Introduction to Materials Medicine 64-73 (Buddy D. Ratner ed., Academic Press, Ltd., 1996). The ceramic materials may be permanent or resorbable depending on their chemistry, blending and even manufacturing methods used. The ring assembly 14 may also be formed of a biocompatiable, resorbable and/or permanent materials, such as those described in the following US patents, the contents of which are incorporated by reference in their entirety herein: U.S. Pat. Nos. 5,432,395, 4,976,715, 5,273,964, 4,157,378, 4,429,691, 4,612,053, 4,684,673, 4,737,411, 4,849,193, 4,880,610, 4,917,702, 4,938,938, 4,959,104, 5,034,059, 5,037,639, 5,047,031, 5,053,212, 5,085,861, 5,129,905, 5,149,368, 5,152,836, 5,164,187, 5,178,845, 5,262,166, 5,279,831, 5,281,265, 5,286,763, 5,336,264, 5,427,754, 5,470,803, 5,496,399, 5,516,532, 5,522,893, 5,525,148, 5,542,973, 5,545,254, 5,562,895, 5,565,502, 5,605,713, 5,650,176, 5,665,120, 5,691,397, 5,700,289, 5,782,971, 5,846,312, U.S. Pat. No. RE33,161, U.S. Pat. No. RE33,221, U.S. Pat. Nos. 5,658,593, 6,752,938, 8,048,443, and 8,048,857.

Figure 100:
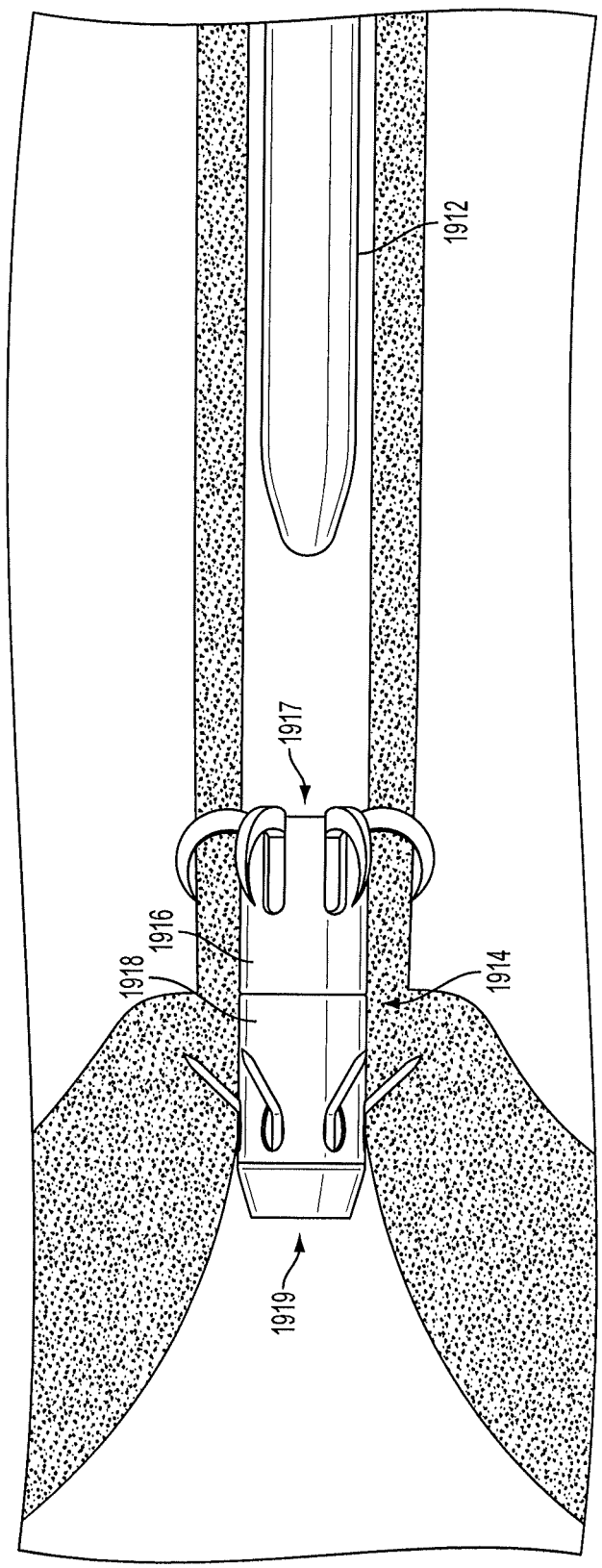
FIG. 100 is a side view of a portion of a further alternative embodiment of an anastomosis system showing the ring assembly installed in the bladder neck and urethra neck of a patient.
Figure 101A:
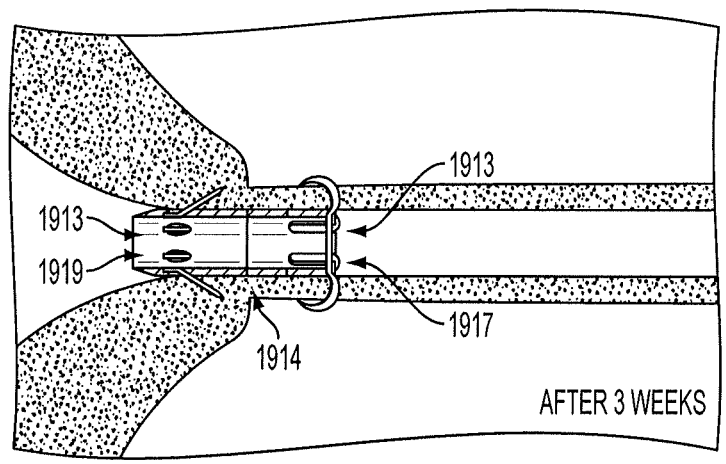
FIG. 101A is a side view of the ring assembly of the anastomosis system depicted in FIG. 100 showing the ring assembly installed in the bladder neck and urethra neck of a patient at three weeks post-implantation.
Figure 101B:
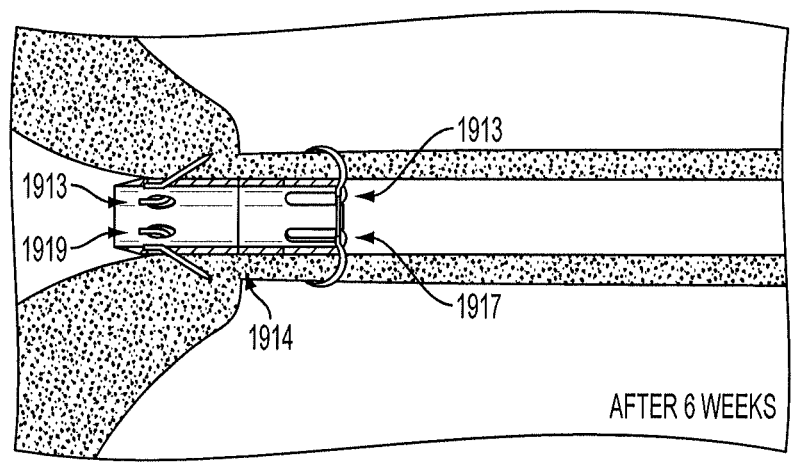
FIG. 101B is a side view of the ring assembly of the anastomosis system depicted in FIG. 100 showing the ring assembly installed in the bladder neck and urethra neck of a patient at six weeks post-implantation.
Figure 101C:
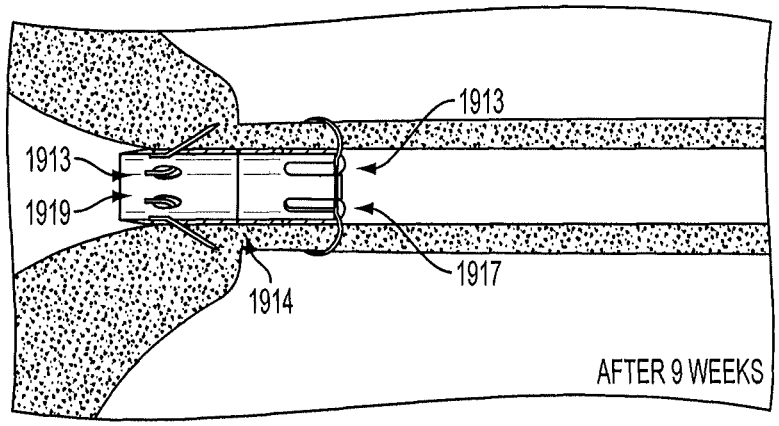
FIG. 101C is a side view of the ring assembly of the anastomosis system depicted in FIG. 100 showing the ring assembly installed in the bladder neck and urethra neck of a patient at nine weeks post-implantation.
Figure 101D:
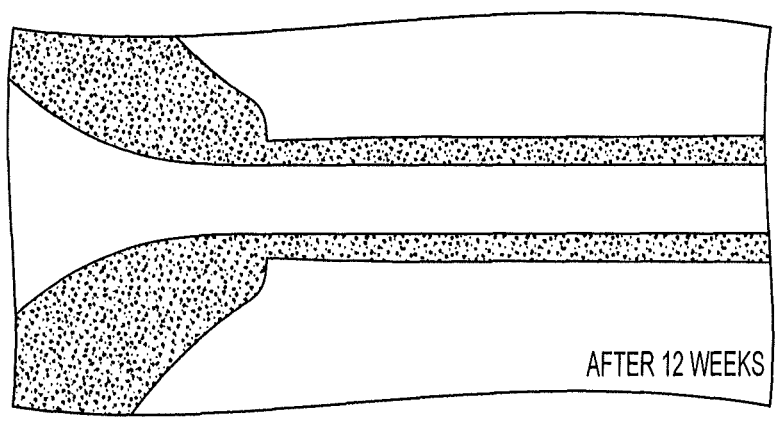

Now, an exemplary embodiment of the ring assembly 1914, depicted in FIGS. 100-101D, will be used to demonstrate an anastomosis and degradation of the ring assembly. It will be understood that, although the embodiment of the ring assembly 1914 is discussed, the degradation described herein will apply equally to all embodiments disclosed and contemplated herein. As mentioned above, when the ring assembly 1914 is formed from resorbable and/or biodegradable materials, it gradually degrades after implantation in the body. Preferably, the material is selected to degrade at a slower rate than the natural healing process, so as to allow healing of the anastomosis before degradation. For example, the ring assembly 1914 can be formed from a material that will (i) remain intact for approximately to six weeks after implantation before degradation and (ii) be completely resorbed or degraded after twelve weeks. Thus, the ring assembly 1914 can be removed or expelled from the patient's body without a follow-up surgical procedure when the ring assembly 1914 is no longer needed to hold the anastomosis.

In the interim, the ring assembly 1914 permits urine to flow from the bladder through a passageway 1913 defined by the lumens 1917, 1919 of the coupling parts 1916, 1918. As shown in FIG. 100, when the upper ring 1918 and the lower ring 1916 are coupled together, lumens 1917 and 1919 define a passageway 1913 extending from the distal end of the upper ring 1918 through to the proximal end of lower ring 1916. Thus, the passageway 1913 permits the flow of urine from the bladder into the urethra while the anastomosis is healing.

Preferably, the ring assembly 1914 forms a leak-proof passageway, so as to reduce or eliminate the chance of leakage of urine into the abdominal cavity. The flow of urine through the ring assembly may operate to degrade the ring assembly and carry non-resorbed materials and portions of the ring assembly out of the body.

FIG. 100 shows a ring assembly 1914 formed from a resorbable material immediately after emplacement, as the surgical instrument 1912 used to implant the ring assembly 1914 is removed, and prior to any degradation. FIGS. 101A to 101D depict the progression of the degradation of the ring assembly 1914 over time, as the anastomosis heals. As shown in FIG. 101A, after three weeks post-implantation, the ring assembly 1914 continues to hold the bladder neck and urethra neck together and permits urine to flow through the passageway 1913. However, as seen by comparison to FIG. 100, a small amount of the material forming the ring assembly 1914 has degraded and been resorbed or carried away by urine flow. FIG. 101B shows that, after six weeks post-implantation, the ring assembly 1914 continues to hold the bladder neck and urethra neck together, but the material comprising the ring assembly 1914 has further degraded. As seen in FIG. 101C, at approximately nine weeks post-implantation, the ring assembly 1914 has degraded substantially. After twelve weeks, the ring assembly 1914 has degraded completely, and the natural healing process has typically progressed sufficiently to permanently hold the bladder and urethra tissue together without the assistance of the ring assembly 1914, hooks or other tissue fastening apparatus, as shown in FIG. 101D.

Details of several additional example embodiments of the ring assembly of the present invention are depicted and described in FIGS. 44-64B. Some of these ring assemblies, such as those described with respect to FIGS. 61-64B, can be adapted for use with the surgical instrument 12 of the first embodiment and/or with adapted versions thereof, with such adaptations being within the capabilities of one of ordinary skill in the art. It will be noted that the concepts described in the embodiments discussed above may be incorporated into the embodiments depicted and described in FIGS. 44-64B, and vice versa.

Figure 62:
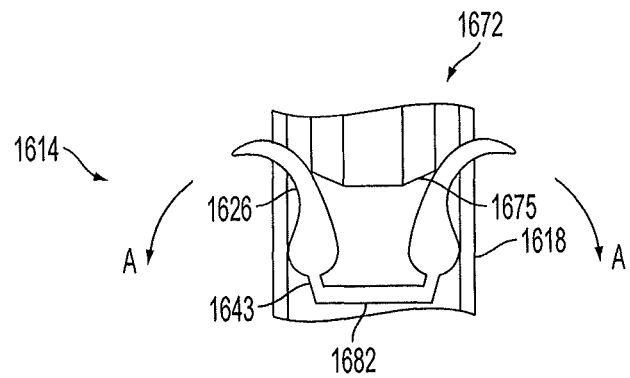
FIG. 62 is a cross sectional view of the anastomosis device depicted in FIG. 61 with securement elements in the process of being deployed.

Referring now to FIGS. 61-64B, a further embodiment of a ring assembly 1614 comprising a collar 1618 is shown. The ring assembly could be used as an upper ring or lower ring, with similar positioning to the previously discussed upper and lower rings 18, 16. The ring assembly includes a central ring that is pivotally attached to securement elements 1626, which are moveable between a stored/retracted/delivery position in which the securement elements 1626 are recessed into the upper collar 1618 and a deployed/extended position in which the securement elements 1626 extend outward from the collar 1618 so that they engage and secure to the surrounding tissue. Securement elements 1626 may be mounted on a central ring 1682 and moveable between the retracted and deployed positions by pivoting around the central ring 1682 which forms a common pivot point 1643 (as shown in FIG. 64A). Arrows "A" in FIGS. 62 and 64A illustrate the movement of the securement elements 1626 towards a deployed position. Alternatively, the securement elements 1626 may be of unitary construction with the central ring 1682 and may be moveable between the retracted and deployed positions by pivoting on a flexible living hinge.

Figure 64A:
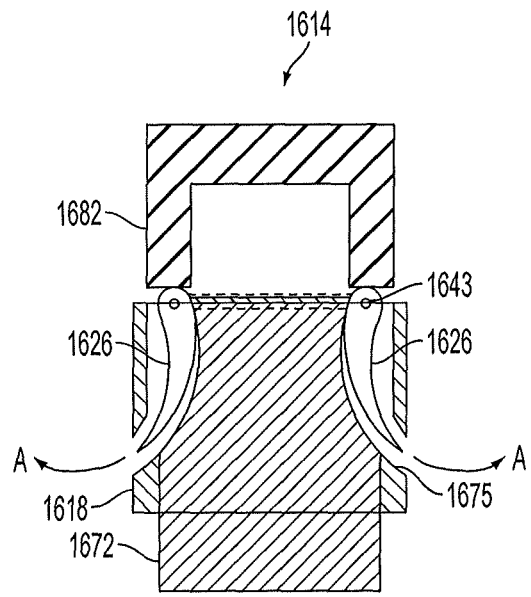
FIG. 64A is a cross sectional view of a further alternative exemplary embodiment of an anastomosis ring device with securement elements in the undeployed position.
Figure 64B:
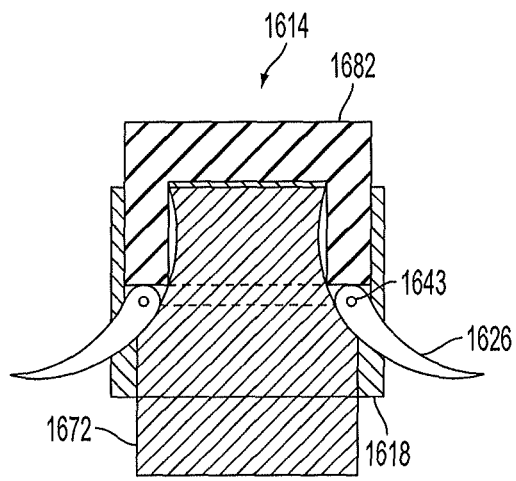
FIG. 64B is a cross sectional view of the anastomosis device depicted in FIG. 64A with securement elements in the deployed position.

FIGS. 64A and 64B, show collar 1618 and securement elements 1626 in greater detail. The arrows "A" in FIG. 64A illustrates the movement of the securement elements 1626 towards a deployed position. In this view, the securement elements 1626 are pivotably mounted to a central ring 1682. The central ring 1682 is visible in cross-section only at pivot points 1643, and is shown in phantom for illustration.

Figure 63:
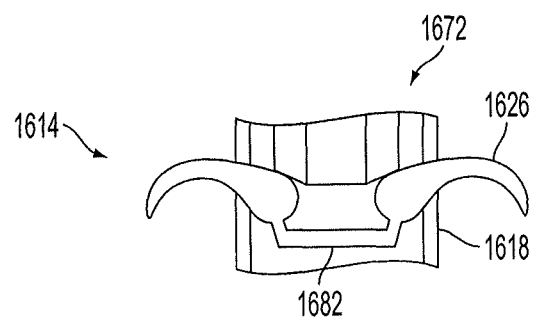
FIG. 63 is a cross sectional view of the anastomosis device depicted in FIG. 61 with securement elements in the deployed position.

FIGS. 61-64B show the securement elements 1626 being guided outward by contact with surface 1675 of the collar 1618 when deployer 1672 is axially moved with respect to the collar 1618. The securement elements 1626 are guided outward to effect piercing of tissue upon axial motion of central ring 1682 towards contact surface 1675, which extends through a portion of the collar 1675. The initial action of guiding the securement elements 1626 to an appropriate position may be aided by the inclusion of a guiding element or anvil 1672 that is part of the implant or insertion instrument. Additionally, the inclusion of notches (not shown) on the securement elements 1626 as shown in FIG. 63 may act as locks to hold the securement elements 1626 in a preferred location with respect to the collar 1618.

The securement elements 1626 may pivot outwardly and axially between 60 and 120 degrees from the stored to the deployed position, such that the securement elements are oriented to maintain a compression fit between the urethra and the bladder for good sealing.

Figure 45:
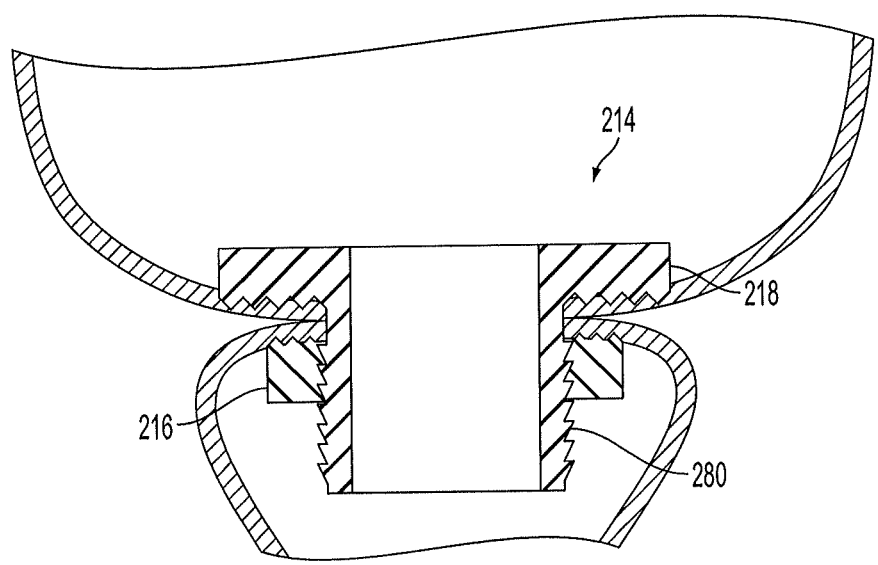
FIG. 45 is a cross sectional view of a further alternative exemplary embodiment of a biodegradable clamp for anastomosis.

FIG. 45 shows a third exemplary embodiment of an anastomosis ring assembly 214 biodegradable clamp for anastomosis. As shown, the anastomosis ring assembly 214 comprises an upper clasp 218 and a lower clasp 216, each generally having a ring or disk shape and having axially-facing surfaces with teeth. The upper clasp 218 also includes a ratchet mechanism 280 that extends axially from the upper clasp 218 and is sized and shaped to engage the inner ring surface of the lower clasp 216. The ratchet mechanism may be of a length that accounts for variable tissue thickness. The ratchet mechanism 280 has resiliently deflectable ratcheting teeth on its outer surface that engage ratcheting teeth on the inner surface of the lower clasp 216 to tighten and hold the upper clasp 218 and lower clasp 216 together. The anastomosis ring assembly 214 maintains the bladder and urethra in compression during healing.

Figure 46:
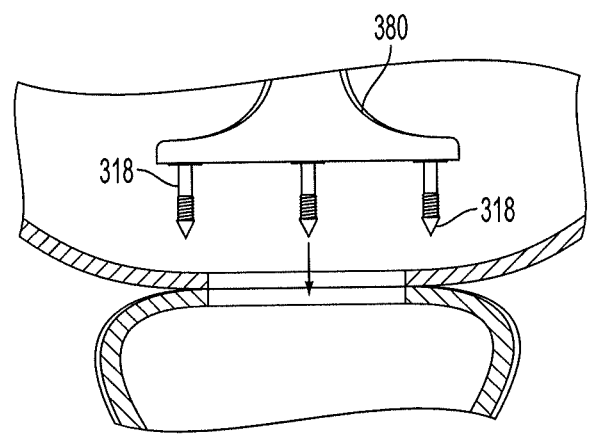
FIG. 46 is a cross sectional view of a further alternative embodiment of an anastomosis device comprising an applicator and biodegradable pins being positioned in the bladder neck.
Figure 47:
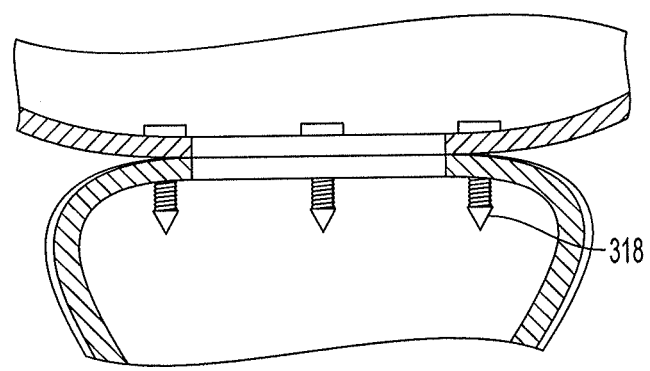
FIG. 47 is a further cross sectional view of the anastomosis device depicted in FIG. 46.
Figure 48:
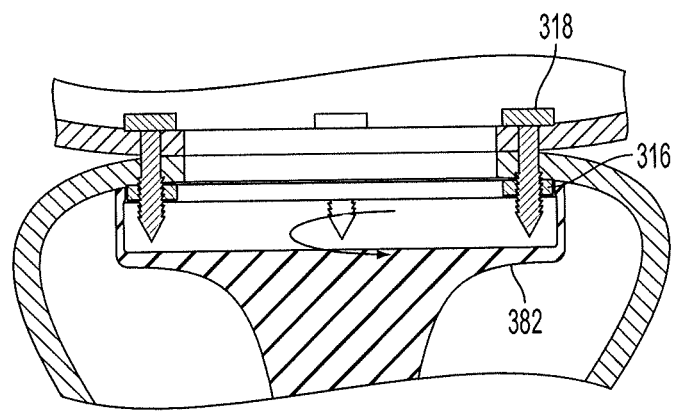
FIG. 48 is a further cross sectional view of the anastomosis device depicted in FIG. 46.
Figure 49:
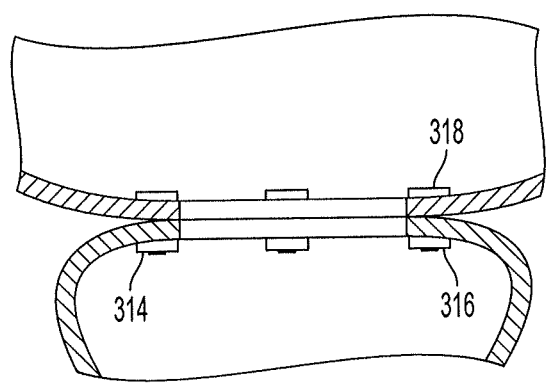
FIG. 49 is a further cross sectional view of the anastomosis device depicted in FIG. 46.

FIGS. 46-49 show a fourth exemplary embodiment of an anastomosis device 314 comprising biodegradable pins 318. As shown in FIGS. 46 and 47, the anastomosis device 314 is positioned by piercing the bladder and urethra walls with metal-tipped bio-degradable pins 318 using a first removable applicator 380. As shown in FIG. 48, bio-degradable lower clasps 316 are attached to the bio-degradable pins 318 using a second removable applicator 382. The bio-degradable lower clasps 316 secure the bio-degradable pins 318 in position. The lower clasps 316 may be threaded and engage a threaded outer surface of the bio-degradable pins 318, or may be secured by press-fit, compression-fit, friction-fit, or the like. After the bio-degradable pins 318 are positioned piercing the bladder and urethra tissue, the metal tips may be removed as shown in FIG. 49. The anastomosis device 314 maintains the bladder and urethra in compression during healing.

Figure 50:
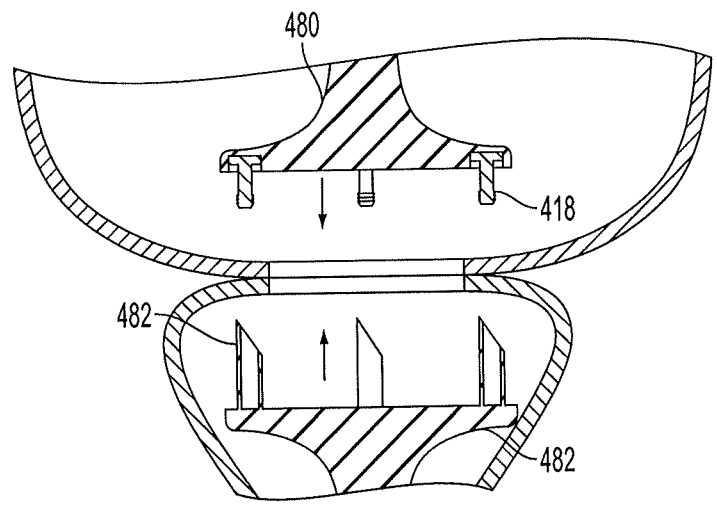
FIG. 50 is a cross sectional view of a further alternative exemplary embodiment of an anastomosis device comprising an applicator with needles and biodegradable pins being positioned in the bladder neck.
Figure 51:
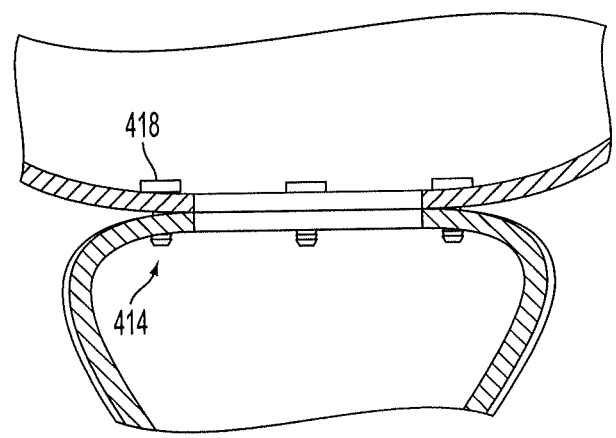
FIG. 51 is a further cross sectional view of the anastomosis device depicted in FIG. 50.

FIGS. 50-51 show a fifth exemplary embodiment of an anastomosis device 414 comprising biodegradable pins 418. As shown in FIG. 50, needles on a lower applicator 482 are used to pierce the tissue of the urethra and bladder. The biodegradable pins 418 may be inserted into the pierced holes using an applicator 480 as shown in FIG. 51. The anastomosis device 414 maintains the bladder and urethra in compression during healing.

Figure 52:
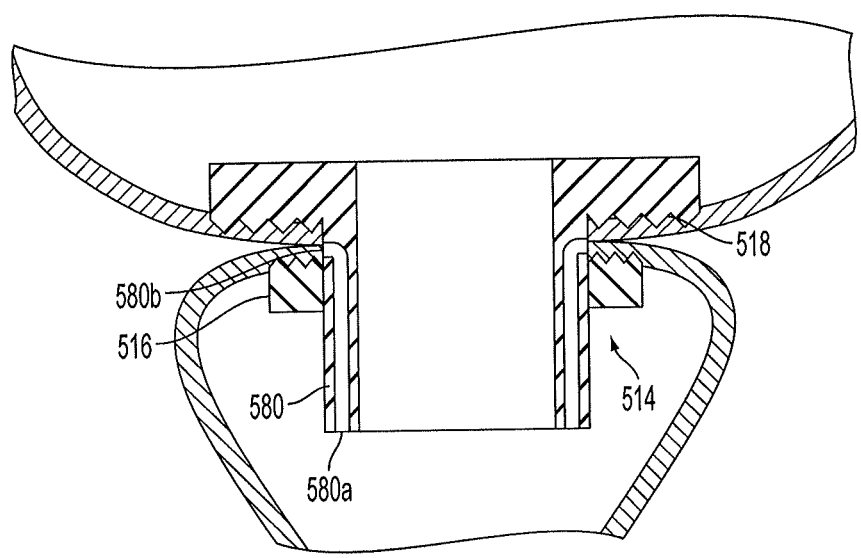
FIG. 52 is a cross sectional view of a further alternative exemplary embodiment of an anastomosis device comprising upper and lower clasps and a channel for gluing the clasps together.

FIG. 52 shows a sixth exemplary embodiment of an anastomosis ring assembly 514. As shown, the anastomosis ring assembly 514 comprises an upper clasp 518 and a lower clasp 516, each having axially-facing surfaces with teeth. The upper clasp 518 also has a structure defining a glue channel 580 with an inlet 580a and outlet 580b. The glue channel outlet 580b is preferably positioned to align with the interface of the bladder neck and urethra neck when the anastomosis ring assembly 514 is emplaced.

The anastomosis ring assembly 514 is positioned by purse-stringing the bladder and fitting the bladder neck with the upper jaw 518. A lower clasp 516 is attached to the upper jaw 518 and engages the urethra. The teeth of the axially-facing surfaces of the upper jaw 518 and lower clasp 116 securely engage with the tissue of the bladder and urethra, respectively.

Once properly positioned, a biocompatible liquid adhesive, such as glue, may be injected into the glue channel inlet 580a. The liquid adhesive travels through the glue channel 580 and exits at the glue channel outlet 580b adjacent the bladder and urethra between the upper and lower clasps 518, 516. After tightening the upper and lower clasps 518, 516 together and curing the liquid adhesive, the liquid adhesive securely adheres the bladder and urethra together. The upper and lower clasps 518, 516 can then be removed leaving only the cured adhesive holding the anastomosis in place.

Figure 53:
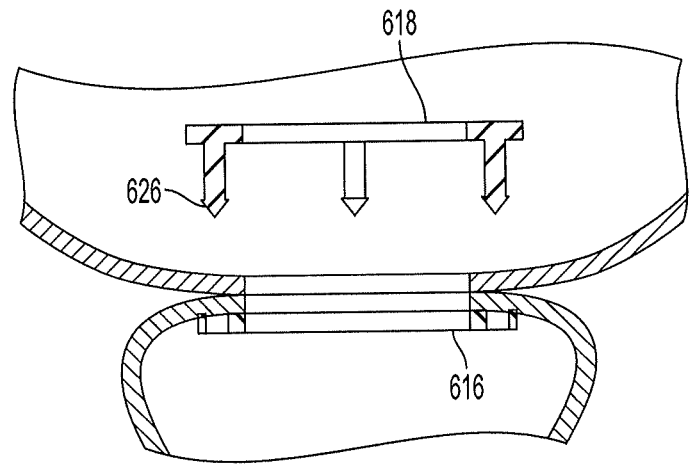
FIG. 53 is a cross sectional view of a further alternative exemplary embodiment of an anastomosis device comprising an upper disk with biodegradable pins being positioned in the bladder neck and a lower disk with holes corresponding to the pins positioned in the urethra neck.
Figure 54:
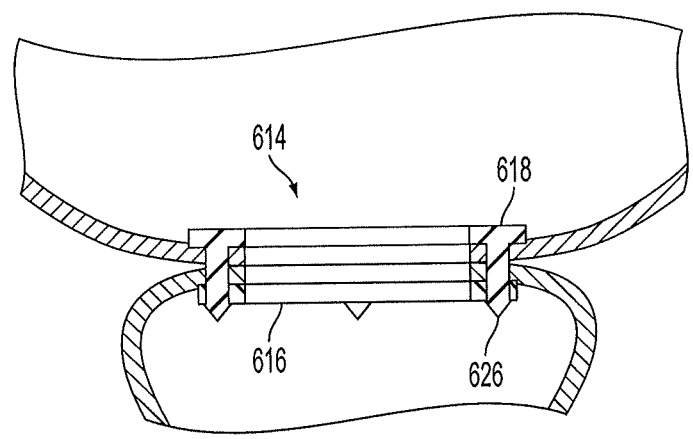
FIG. 54 is a further cross sectional view of the anastomosis device depicted in FIG. 50.

FIGS. 53 and 54 show a seventh exemplary embodiment of an anastomosis ring assembly 614. As shown, the anastomosis ring assembly 614 comprises an upper disk 618 and a lower clasp 616. As shown, the upper disk 618 has securement members 626 extending from a lower surface and the lower disk 616 has openings sized and positioned to receive the securement members of upper disk 618. The securement members 626 of the upper disk 618 may be barbed or hook-shaped.

The bladder and urethra are connected by being clamped between the upper disk 618 and lower disk 616. The securement members 626 of the upper disk 618 pierce the tissue and insert into the openings of the lower clamp 616 to lock the upper disk 618 and lower clamp 616 together. The entire assembly may be formed from bio-degradable material.

Figure 55:
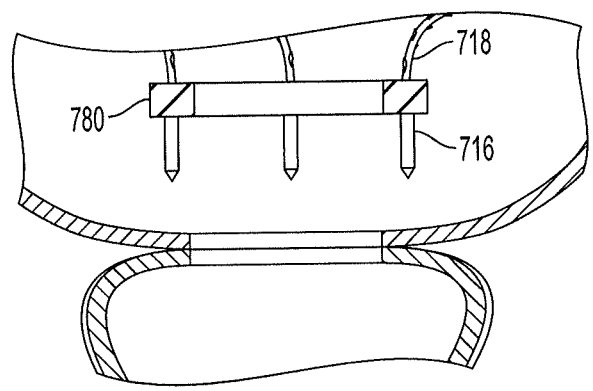
FIG. 55 is a cross sectional view of a further alternative embodiment of an anastomosis device comprising an applicator with needles and barbed sutures.
Figure 56:
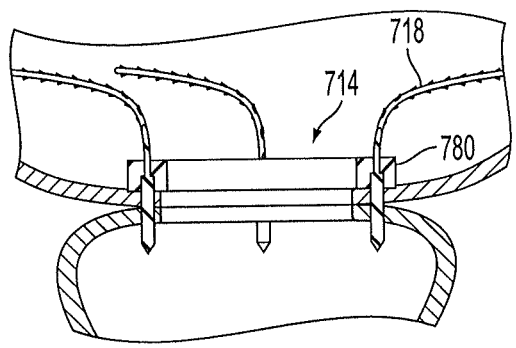
FIG. 56 is a cross sectional view of the anastomosis device depicted in FIG. 55 comprising an applicator with needles and barbed sutures being positioned in the bladder neck.
Figure 57:
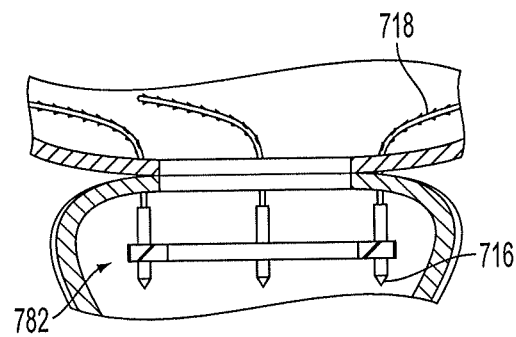
FIG. 57 is a cross sectional view of the anastomosis device depicted in FIG. 55 with an applicator pulling the barbed sutures through the tissue of the bladder neck and urethra neck.
Figure 58:
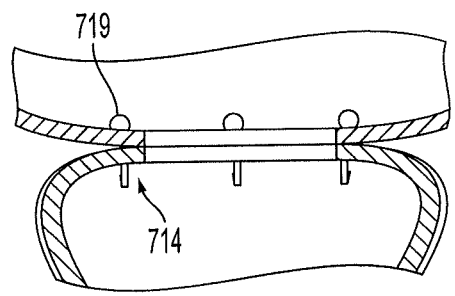
FIG. 58 is a cross sectional view the anastomosis device depicted in FIG. 55 with sutures positioned in the bladder neck and urethra neck.

FIGS. 55-58 show an eighth exemplary embodiment of an anastomosis device 714 comprising biodegradable sutures 718. As shown in FIGS. 55 and 56, the anastomosis device 714 is positioned by piercing the bladder and urethra walls with needles 716 using a first removable applicator 780. As shown, the needles 716 are attached to trailing biodegradable sutures 718 which are barbed, but un-barbed sutures may also be used. As shown in FIG. 57, a second removable applicator 782 is used to advance the needles 716 and pull the biodegradable sutures 718 through the tissue. The bio-degradable sutures 718 may have a preformed knot, bulb or other structure 719 on the end opposite the needle 716 to prevent the trailing end of the suture from continuing to advance through the bladder tissue. The combination of a knot or bulb on the trailing end and barbed sutures (where the barbs anchor into the tissue, thereby preventing the suture from pulling out of the tissue) or a second knot applied to the leading end of the suture secure the anastomosis.

Figure 59:
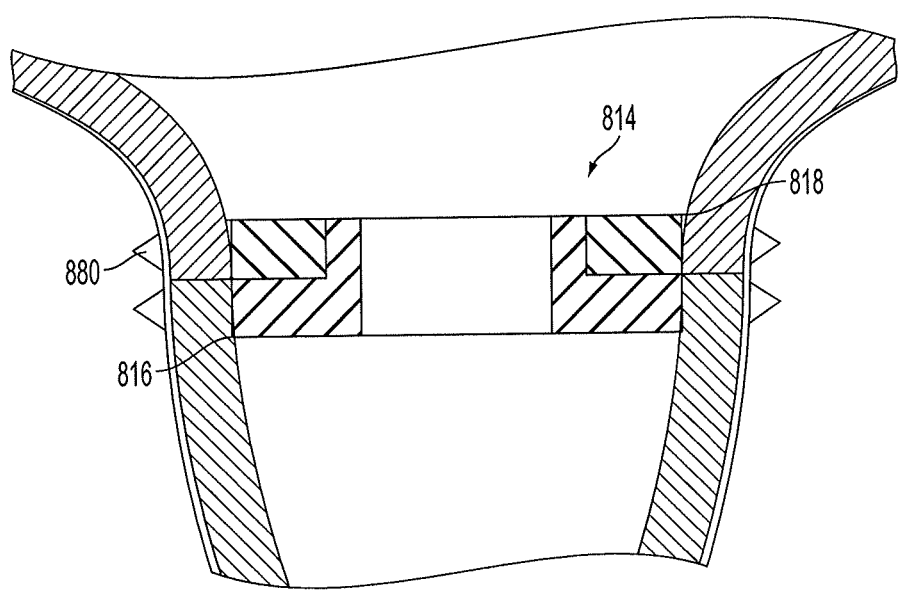
FIG. 59 is a cross sectional view of a further alternative embodiment of an anastomosis device comprising a bio-degradable lateral pin disk.

FIG. 59 shows a ninth exemplary embodiment of an anastomosis ring device 814. As shown, the anastomosis ring device 814 comprises bio-degradable upper and lower disks 818, 816 having lateral/radial outwardly-extending securement members 880 on their outer surfaces. The securement members 880 may be hooks, barbs, or any other shape so long as they have a pointed end capable of piercing the bladder and urethra. The upper and lower disks 818, 816 are fixed to the bladder and urethra, respectively, by compressing the bladder and urethra onto the securement members 880, which pierce and secure to the bladder and urethra walls. The disks are fixed and sealed together (e.g., by snap-fit connector elements) so that the bladder and urethra remain secured together.

Figure 60:
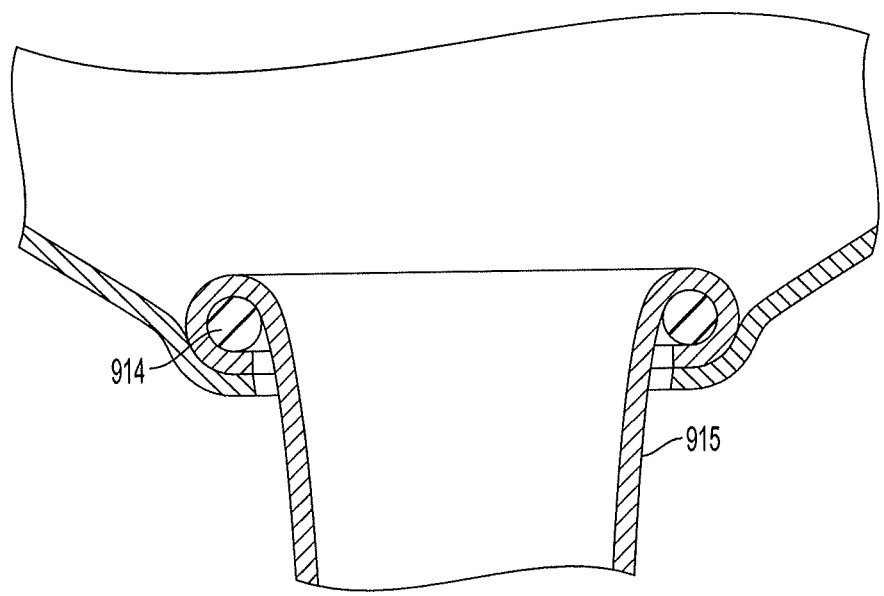
FIG. 60 is a cross sectional view of a further alternative embodiment of an anastomosis device comprising a bio-degradable ring.
Figure 61:
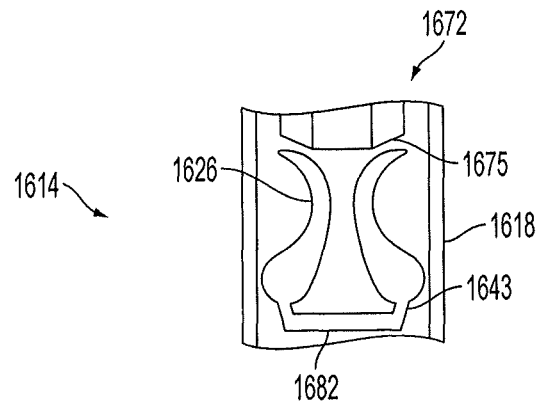
FIG. 61 is a cross sectional view of a further alternative exemplary embodiment of an anastomosis device with securement elements in the undeployed position.

FIG. 60 shows a tenth exemplary embodiment of an anastomosis ring device 914. As shown, the anastomosis ring device 914 is a ring that has a larger diameter than the cut end of the urethra 915 and is preferably resiliently deformable. The mouth of the urethra is formed into a funnel shape by pulling the urethra neck through the central opening and folding the urethra around the anastomosis ring device 914. This funnel-shaped urethral mouth is then inserted into the bladder. The bladder neck is then purse-stringed to reduce the diameter of the bladder mouth around the funnel-shaped urethral mouth thereby preventing the funnel-shaped urethral mouth from pulling out of the bladder.

Figure 44:
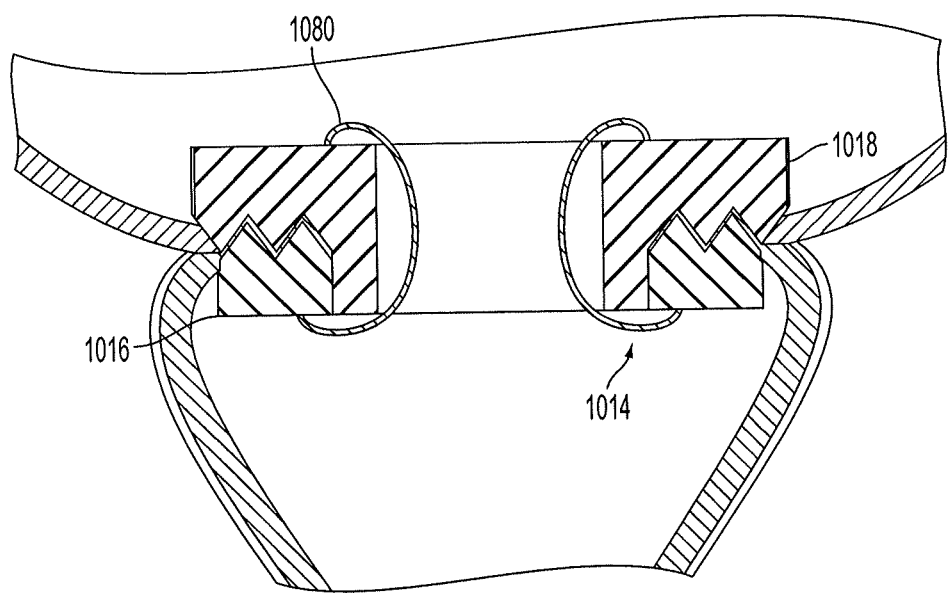
FIG. 44 is a cross sectional view of an alternative exemplary embodiment of an anastomosis ring device.

FIG. 44 shows an eleventh exemplary embodiment of an anastomosis ring assembly 1014 that causes staged necrosis. As shown, the anastomosis ring assembly 1014 comprises an upper jaw 1018 and a lower clasp 1016, each having axially-facing surfaces with mating teeth.

To position the anastomosis ring assembly 1014, the bladder is purse-stringed and fitted with the upper jaw 1018. A lower clasp is attached to the upper jaw 1018 and engages the urethra. The mating teeth of the axially-facing surfaces of the upper jaw 1018 and lower clasp 1016 pierce into the tissue of the bladder and urethra, respectively. As shown in FIG. 44, the lower clasp 1016 and the upper jaw 1018 are maintained in compression by retaining spring 1018. However, other means of maintaining the lower clasp 1016 and the upper jaw 1018 in compression are possible, including but not limited to mating screw threads. Compression of the bladder and urethra tissue between the lower clasp 1016 and the upper jaw 1018 maintains the anastomosis for several days during healing. However, prolonged compression may lead to necrosis, so the upper jaw and lower clasp is preferably removed after a few days. A thread may be attached to ensure proper pull-out of the device.

Figure 65:
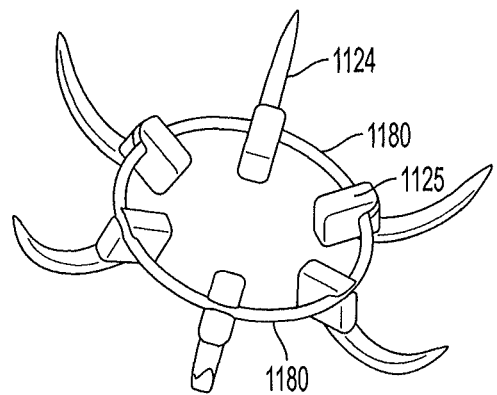
FIG. 65 is a perspective view of a further exemplary embodiment of a central ring of an anastomosis device with securement elements pivotally mounted thereon.

Referring now to FIGS. 65-68B, a twelfth exemplary embodiment is shown. A ring 1116 defines a central lumen and is provided with securement elements 1124 that are moveable between a stored/retracted position in which they are recessed into the ring body and a deployed/extended position in which they extend outwardly from the ring body so that they engage and secure to the wall of the bladder or urethra. As shown in FIG. 65, the securement elements 1124 are pivotably mounted on a central ring 1180 and comprise cooperating cam surfaces 1125 extending within the lumen of the ring 1116. The securement elements 1124 may be moveable between the retracted and deployed positions by pivoting around the central ring 1180 which forms a common pivot point.

Figure 66:
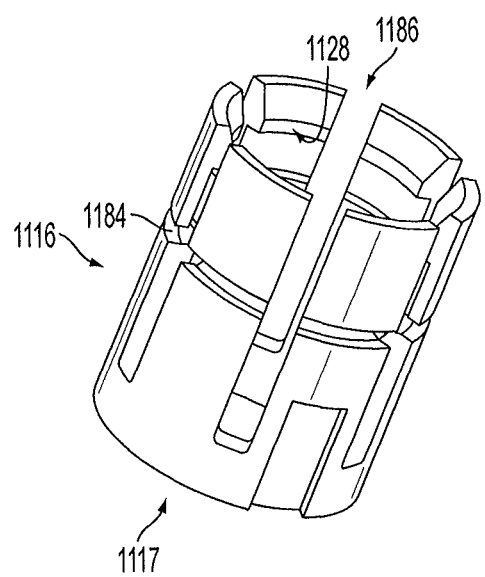
FIG. 66 is a perspective view of a further exemplary embodiment of a lower coupling part of an anastomosis device.

As shown in FIG. 66, the ring 1116 defines a central lumen 1117 that permits the passage of fluid and lower ring deployment mechanism 1148 therethrough. The ring 1116 is provided with a circumferential groove 1184 on its outer surface. Additionally, the body of the ring 1116 defines longitudinal slots 1186. The groove 1184 is sized and shaped to receive the central ring 1180 and the longitudinal slots 1186 are adapted to receive the securement elements 1124 when the central ring 1180 is mounted in the groove 1184. It should also be understood that the lower ring 1116 may have an inner circumferential groove on its inner circumferential surface (not shown) for retaining an appropriately sized version of the central ring within the inner diameter 1116. The inner circumferential groove may replace the circumferential groove 1184, while performing essentially the same function on the inner diameter of the lower ring 1116.

FIGS. 67A and 67B show the central ring 1180 mounted in the groove 1184 of the ring 1116 and the securement elements 1124 in the undeployed position. As shown, the securement elements 1124 are received within corresponding longitudinal slots 1186 of the body of ring 1116. FIGS. 68A and 68B show the securement elements 1124 in the deployed state radially extending from the body of the ring 1116.

Similar to the previously described embodiments, the securement elements 1124 of this embodiment are adapted to be deployed by the lower ring securement element deployer 1148. The lower ring securement element deployer 1148 extends from the tube 1146 and deploys the lower ring securement elements 1124 upon axial translation of the upper tube 1146 in the proximal direction (i.e., axial retraction) with respect to the ring 1116. As illustrated by the cross-sectional views in FIGS. 67B and 68B, the lower ring securement element deployer 1148 defines a cam surface 1147 that engages cooperating cam surfaces 1125 of the lower ring securement elements 1124 to pivot securement elements 1124 towards the deployed position when the upper tube 1146 is axially retracted with respect to the handle assembly 1132. In this embodiment, the lower ring securement element deployer 1148 may have circumferential ridges extending radially from the upper tube 1146. As shown, the ridges define the cam surfaces 1147 that engage the cooperating cam surface 1125 of the lower ring securement elements 1124.

Additionally, as mentioned with respect to the previously discussed embodiments, the lower ring securement element deployer 1148 may be adapted to mount an upper ring to its distal end. While the upper ring is not shown, the upper ring may also have a central lumen and upper ring securement elements may be pivotally mounted on a ring fitted into a circumferential groove on the outer surface. The upper ring securement element deployment mechanism of this embodiment may be similar to the upper ring securement element deployer 72 of the previously discussed embodiments.

As shown in FIG. 66, the ring 1116 has interconnector elements 1128 provided by resiliently deflectable arms. The interconnector elements 1128 are adapted to couple with corresponding interconnector elements on the upper ring and can be snap-fit connectors, screw-together connectors, or other conventional connector assemblies, whether detachable for decoupling or intended for one-time connection only. As with the previously discussed embodiments, the interconnector elements couple the ring 1116 when the ring is brought into proximity and urged towards an interconnecting relationship.

Referring now to FIGS. 69A-70B, a thirteenth embodiment of the upper and lower rings 1218, 1216 with securement elements 1226 and 1224 connected to the upper and lower rings 1218, 1216 by living hinges is shown. In this embodiment, the securement elements 1224, 1226 are deployed by pivoting about the living hinge 1222 in the direction of the arrows in FIGS. 69B and 70B. As shown, the upper and lower ring 1218, 1216 each have a unitary construction and may be injection molded.

In the undeployed position shown in FIGS. 69-70, the securement elements 1224 and 1226 reside within recesses in the body of the lower and upper rings 1216, 1218. The securement elements 1224 of the lower ring 1216 are adapted to be deployed by a lower ring securement element deployer (not shown) according to a mechanism similar to that of the first embodiment. Specifically, the lower ring securement element deployer extends through the central lumen of the lower ring and defines a cam surface that engages cooperating cam surfaces 1229 of the securement elements 1224. Axial retraction of the lower ring securement element deployer against the lower ring securement elements 1224 urges the securement elements to pivot at the living hinges 1222 and radially extend.

The securement elements 1226 of the upper ring 1218 are also adapted to be deployed by an upper ring securement element deployer (not shown) according to a mechanism similar to that of the first embodiment. Specifically, the upper ring securement element deployer extends through the central lumen of the lower and upper rings 1216, 1218 and defines a cam surface that engages cooperating cam surfaces 1227 of the upper ring securement elements 1226. Axial retraction of the upper ring securement element deployer against the cooperating cam surfaces of the upper ring securement elements 1226 urges the securement elements to pivot at the living hinges 1222 and radially extend from the upper ring body 1218.

Figure 71:
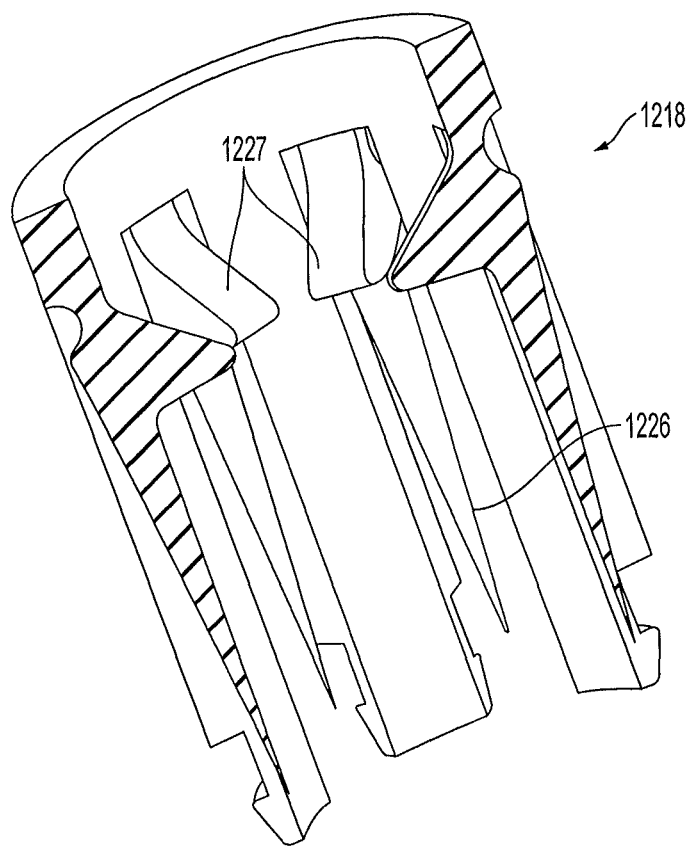
FIG. 71 is a perspective view of a further exemplary embodiment of an anastomosis device showing an upper coupling part with securement elements in the undeployed position.

As shown in 69B, the cooperating cam surfaces 1227 of the upper ring securement elements 1226 may be provided with a notch or ridge to aid in engagement with the deployer cam surface (not shown). Alternatively, as shown in FIG. 71, the upper ring securement element 1226 may lack a ridge or notch such that cooperating cam surfaces 1227 smoothly extend from the inner wall of the upper ring 1218.

Figure 69A:
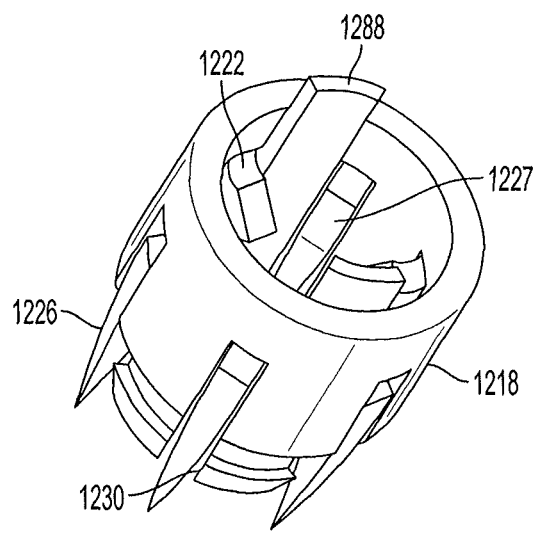
FIG. 69A is a perspective view of a further alternative exemplary embodiment of an anastomosis device showing upper coupling part with securement elements in the undeployed position.
Figure 69B:
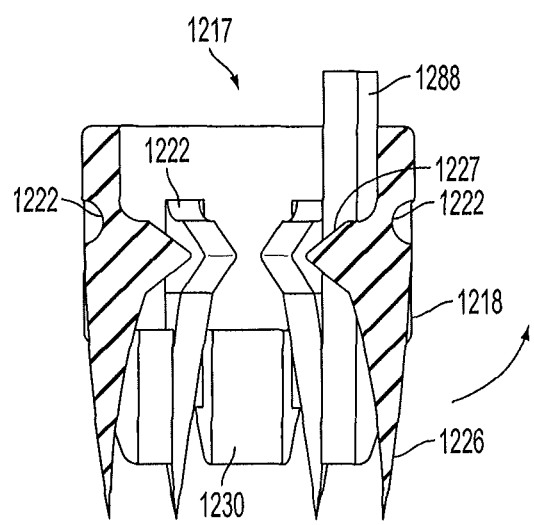
FIG. 69B is a cross sectional view of the anastomosis device depicted in FIG. 69A.
Figure 70A:
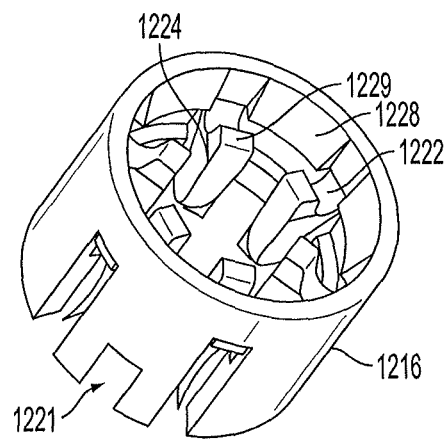
FIG. 70A is a perspective view of a further exemplary embodiment of an anastomosis device showing a lower coupling part with securement elements in the undeployed position.
Figure 70B:
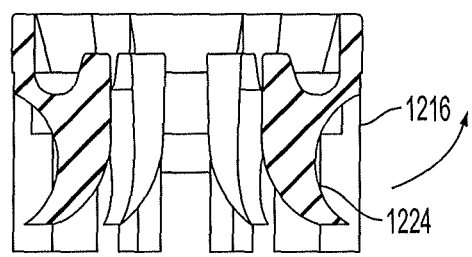
FIG. 70B is a cross sectional view of anastomosis device depicted in FIG. 70A.

Additionally, as shown in FIGS. 69A and 70A, the lower ring 1216 and upper ring 1218 are provided with interconnector elements 1228 and 1230 adapted to couple the upper ring 1218 and lower ring 1216 together. As with the previously discussed embodiments, the interconnector elements 1230, 1228 couple the upper and lower ring 1218, 1216 when the rings are brought into proximity and urged towards an interconnecting relationship. The upper ring 1218 defines a lumen 1217 and is provided with a slidable locking member 1288. The locking member 1288 is mounted axially within the lumen 1217 of the upper ring 1218 and is movable though the lumen 1217 towards the lower ring 1216 when the upper and lower rings 1218, 1216 are coupled together. The locking element 1288 engages a securement element 1224 of the lower ring 1216 when in the deployed position and restricts movement of the engaged securement elements 1226 towards the retracted position.

Figure 72A:
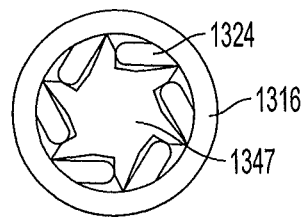
FIG. 72A is a cross sectional view of a further alternative exemplary embodiment of an anastomosis device showing coupling part with securement elements in the undeployed position and a securement element deployer.
Figure 72B:
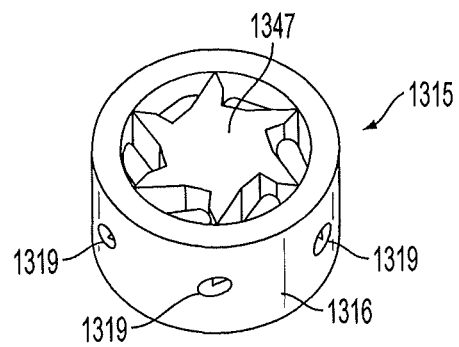
FIG. 72B is a perspective view of the anastomosis device depicted in FIG. 72A.
Figure 73A:
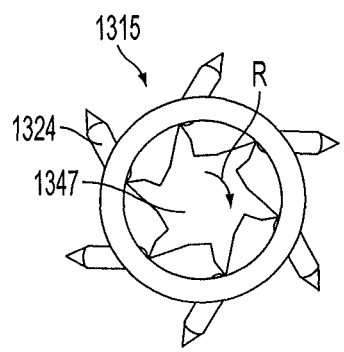
FIG. 73A is a cross sectional view of the anastomosis device depicted in FIG. 72A with securement elements in the deployed position and a securement element deployer.
Figure 73B:
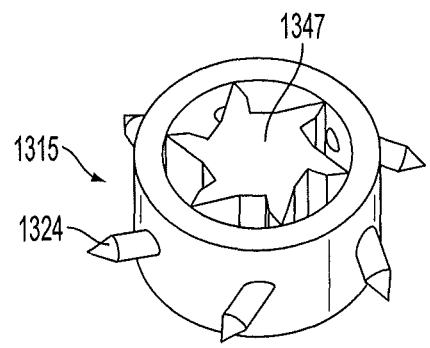
FIG. 73B is a perspective view of the anastomosis device depicted in FIG. 73A.
Figure 74:
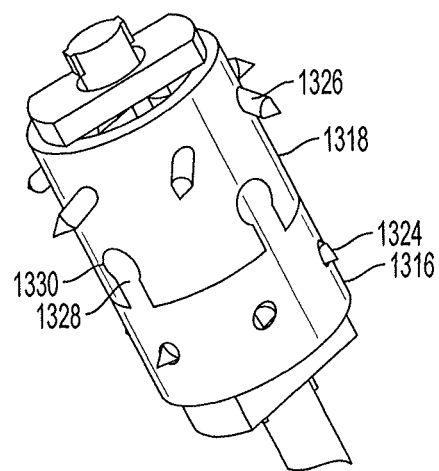
FIG. 74 is a perspective view of the anastomosis device depicted in FIGS. 72 and 73 as a coupled ring assembly and a securement element deployer.

Referring now to FIGS. 72-74, a fourteenth embodiment of a coupling ring 1315 is shown. The coupling ring 1315 has rigid securement elements 1324 and a central lumen with a deployment mechanism 1347 extending therethrough. The body of the coupling ring 1315 defines openings 1319 adapted to receive the securement elements 1324 therethrough. As shown in the undeployed position, the securement elements 1324 are recessed within the body of the coupling ring 1315 with the tips positioned in alignment with the openings 1319 in the body of the coupling ring 1315. A rotary deployment mechanism 1347 having tangentially extending teeth is also positioned in the lumen of the coupling ring 1315. The teeth of the deployment mechanism 1347 engage the inward facing end of the securement elements 1324.

The deployment mechanism 1347 is adapted to deploy the securement elements 1324 upon clock-wise rotation with respect to the coupling ring 1315. The arrow "R" in FIGS. 72A and 72B illustrates the rotation of the deployment mechanism 1347. Clockwise rotation of the deployment mechanism 1347 drives the securement elements 1324 at an angle through the openings 1319 in the body of the coupling ring 1315, thereby extending the securement elements 1324 tangentially from the coupling ring 1315. The angle of the securement elements 1324 may be selected to cause the tissue to be drawn towards the coupling ring 1315 when axial force is placed on the coupling ring 1315.

FIGS. 72 and 73 show the deployment mechanism that may be used in both the upper and lower rings of ring assembly. Accordingly, the coupling ring 1315 as shown in FIGS.

72-73 is generic to the upper and lower coupling parts and lacks interconnecting elements. However, the generic coupling ring 1315 can be modified to include interconnecting elements to permit two corresponding coupling rings to couple together. For example, FIG. 74 shows the lower ring and upper ring 1316, 1318 with interlocking connector elements 1328 and 1330. As shown, the securement elements 1326 of the upper ring 1318 extend at an angle, whereas the securement elements 1324 of the lower ring 1316 remain within the body.

Figure 75:
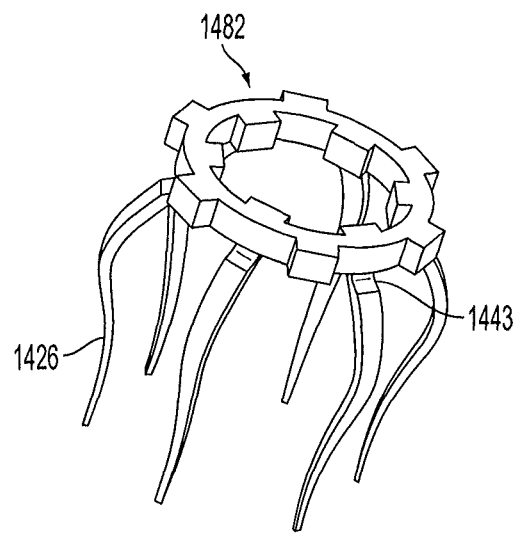
FIG. 75 is a perspective view of a further alternative exemplary embodiment of an anastomosis device showing a central ring with resilient securement elements mounted thereon.

FIGS. 75-81 show a fifteenth embodiment of an anastomosis ring device. This embodiment includes a central ring 1482 having resiliently flexible securement elements 1426 extending axially from the central ring 1482. The securement elements 1426 can bend and flex in a radial direction when a force is applied thereto, but are biased to return to the position of axially extending from the central ring 1482 as shown in FIG. 75. As shown, the securement elements 1426 are provided with a living hinge 1443 to further increase flexibility. However, the flexibility of the securement elements 1426 may be due solely to the flexibility of the material forming the securement elements 1426 rather than living hinge 1443.

Figure 76:
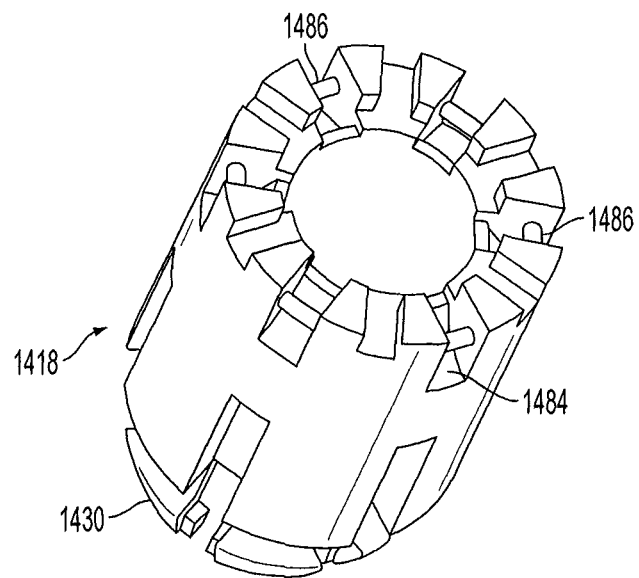
FIG. 76 is a perspective view of the anastomosis device depicted in FIG. 75, showing an upper coupling part.
Figure 77:
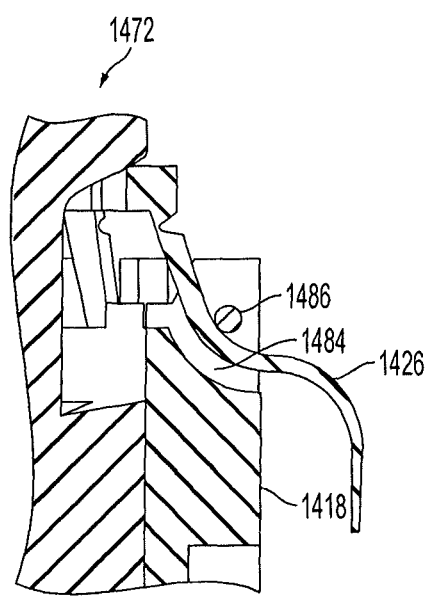
FIG. 77 is a cross sectional view of the anastomosis device depicted in FIG. 74, showing the central ring with resilient securement elements and an upper coupling part.

FIG. 76 shows an example of an upper ring 1418 having a central lumen extending therethrough and interconnector elements 1430 adapted to couple to corresponding interconnecting elements of a lower ring (not shown). The upper ring 1418 has axial grooves 1484 and guide structures 1486 provided on the end opposite the interconnector elements 1430. As shown in FIG. 77, the axial grooves 1484 and guide structures 1486 cooperate to receive there between and guide the securement elements 1426 during deployment.

Figure 78A:
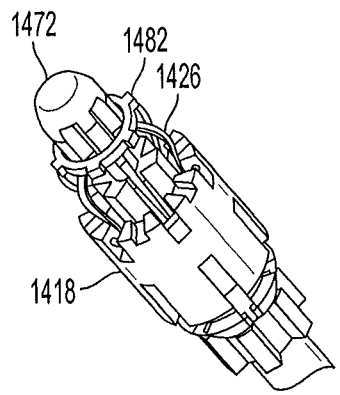
FIG. 78A is perspective view of a further alternative exemplary embodiment of an anastomosis device showing an upper coupling part and a central ring with resilient securement elements mounted on a deployment mechanism.
Figure 78B:
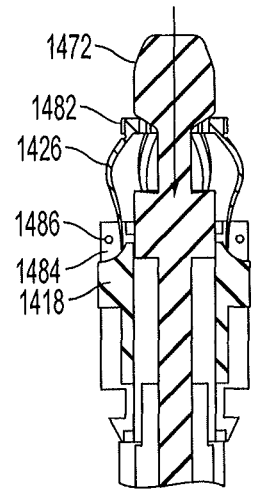
FIG. 78B is cross sectional view of the anastomosis device depicted in FIG. 78A.
Figure 79A:
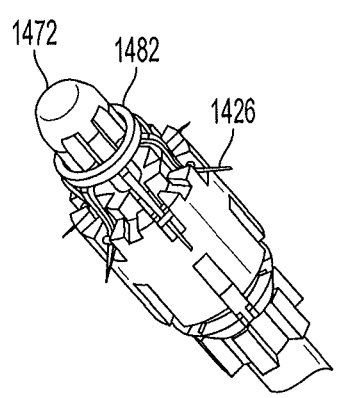
FIG. 79A is perspective view of the anastomosis device depicted in FIG. 78A, shown in an initial stage of deployment.
Figure 79B:
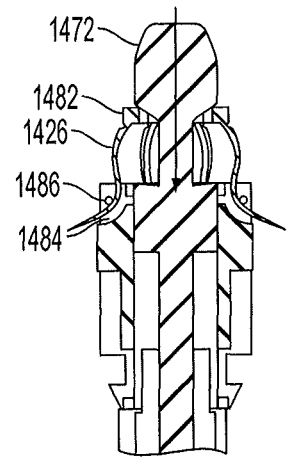
FIG. 79B is cross sectional view of the anastomosis device depicted in FIG. 78A, shown in an initial stage of deployment.
Figure 80A:
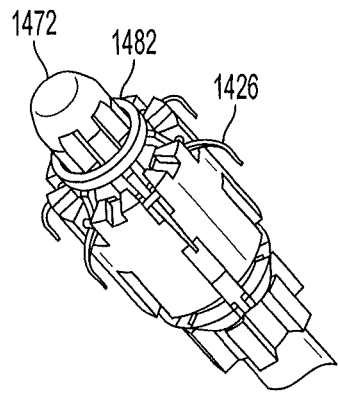
FIG. 80A is perspective view of the anastomosis device depicted in FIG. 78A, shown in an intermediate stage of deployment.
Figure 80B:
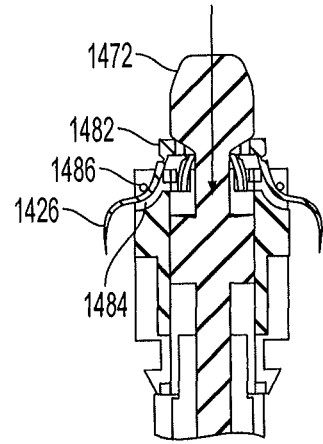
FIG. 80B is cross sectional view of the anastomosis device depicted in FIG. 78A, shown in an intermediate stage of deployment.
Figure 81A:
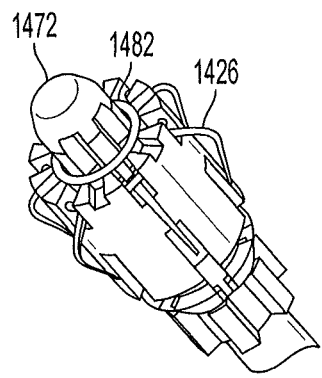
FIG. 81A is perspective view of the anastomosis device depicted in FIG. 78A, shown in a final stage of deployment.
Figure 81B:
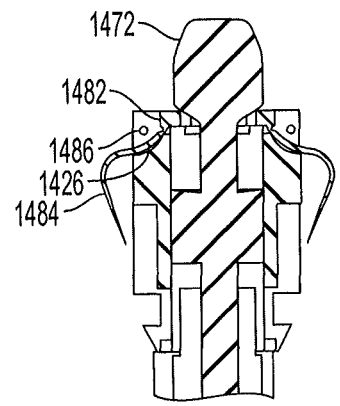
FIG. 81B is cross sectional view of the anastomosis device depicted in FIG. 78A, shown in a final stage of deployment.

As shown in FIGS. 78A and 78B, the central ring 1482 is mounted on an upper ring securement element deployer 1472, which extends through the lumen of the upper ring 1418. Axial retraction of the upper ring securement element deployer 1472 with respect to the upper ring 1418 draws the central ring 1482 proximally and the securement elements 1426 are received by the axial grooves 1484 and guide structures 1486. As the upper ring securement element deployer 1472 is retracted further with respect to the upper ring 1418, the securement elements 1426 are urged against the guide structures 1486, which causes the securement elements 1426 to flex and deflect outwardly as shown in FIGS. 79A and 79B. As shown in FIGS. 80A and 80B, continued axial retraction of the upper ring securement element deployer 1472 pushes the central ring 1482 proximally and forces the securement elements 1426 to pass between the axial grooves 1484 and guide structures 1486 until the securement elements 1426 are positioned such that the axial grooves 1484 and guide structures 1486 no longer apply a force on the securement elements 1426. As shown in FIGS. 81A and 81B, when the upper ring securement element deployer 1472 carries the central ring 1482 into engagement with the upper ring 1418, the securement elements 1426 return to their unbiased configuration, thereby securing the upper ring 1418 to the vessel tissue.

While the deployment mechanism of the fifteenth embodiment is only illustrated by means of the upper ring 1418, it can be adapted for use with a lower ring. Additionally, as with other embodiments, after deployment of the securement elements, the upper and lower ring can be brought into proximity and coupled together.

Figure 82A:
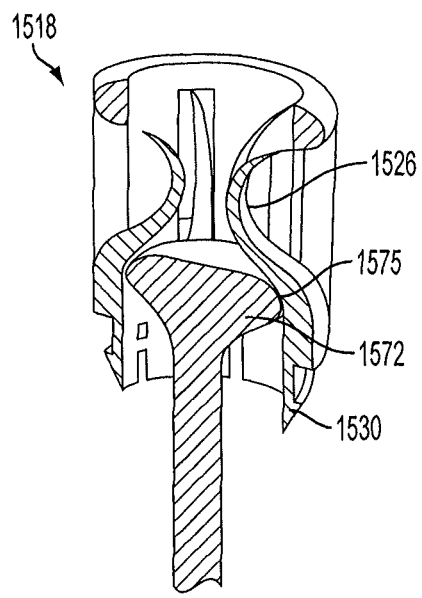
FIG. 82A is cross sectional view of a further alternative exemplary embodiment of an anastomosis device showing an upper coupling member in an undeployed position.
Figure 82B:
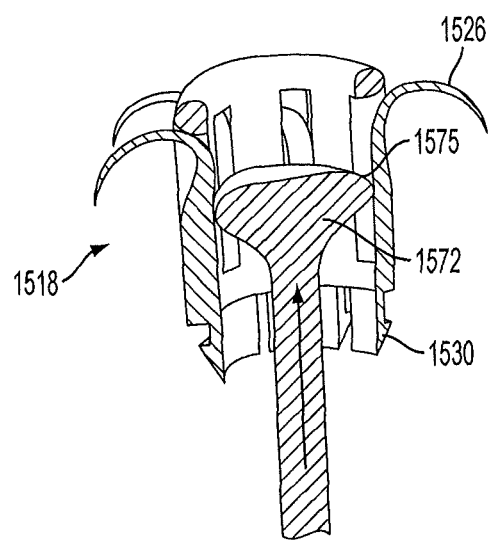
FIG. 82B is cross sectional view of the anastomosis device depicted in FIG. 82A, shown in the deployed position.

Referring now to FIGS. 82A and 82B, a sixteenth embodiment of an upper ring 1518 of an anastomosis ring assembly is shown. As shown, the upper ring 1518 has a unitary construction and may be injection molded. The upper ring 1518 has a central lumen, interconnecting elements 1530, and securement elements 1526 that extend into the lumen. The securement elements 1526 are formed from a flexibly resilient material and are adapted to engage upper ring securement element deployer 1572.

As shown, axial extension of the upper ring securement element deployer 1572 (as indicated by the arrow in FIG. 82B) through the lumen of the upper ring 1518 brings the cam surface 1575 of the upper ring securement element deployer 1572 into engagement with the securement elements 1526. Further axial extension of the upper ring securement element deployer 1572 displaces the securement elements 1526 and causes the cam surface 1575 to urge the securement elements 1526 to project outward.

While the deployment mechanism of the sixteenth embodiment is only illustrated with respect to the upper ring 1518, it can be adapted for use with a lower ring. Additionally, as with other embodiments, after deployment of the securement elements, the upper and lower ring can be bought into proximity and coupled together.

Turning now to FIGS. 83 A-C, an example profile of securement elements for use with the various embodiments of the present invention are shown from top and side viewpoints and in cross-section. As shown, the securement element 24 is curved and has a ridge extending 25 along the curved outer surface. When mounted to a coupling ring and deployed, the ridge extends away from the coupling ring and the flat side faces the coupling body. The upper or lower securement element 24 as shown in FIGS. 83A-83C may used as upper and/or lower securement elements and may be adapted for use with any of the embodiments of coupling rings disclosed herein.

It will be noted that in some other embodiments, the mating screw threads can be reversed so that the operations described are performed by rotating the components in the opposite angular directions. In some other embodiments, the ring-mounting steps and the securement element-deploying steps can be performed by other components of the system. In some other embodiments, the securement elements can be spring-biased to their deployed positions and deployed by actuation of a release member.

It should be understood that, although this disclosure describes different embodiments separately, that one skilled in the art may combine the features different embodiments without departing from the anastomosis devices and system disclosed herein. For example, one skilled in the art may incorporate the securement elements and deployment mechanism of one embodiment in an upper ring (e.g., rigid pivotable hooks, etc.) while incorporating a different securement element and deployment mechanism (e.g., resilient flexible hooks, etc.) in the lower ring. Furthermore, it should be apparent to those skilled in the art that the tissue capture elements referred to as "upper" and lower" may be adapted for use interchangeably. In other words, a ring shown engaging the bladder or described as "upper" may be adapted to engage the urethra or used as a "lower" ring. Likewise, a ring shown engaging the urethra or described as "lower" may be adapted to engage the bladder or used as an "upper" ring.

Additionally, all US patents, applications, and published literature cited herein are incorporated by reference in their entireties.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein. And any dimensions shown the attached drawings are representative and not limiting of the invention, as larger or smaller dimension can be used as desired.

Although the present invention has been described above in terms of exemplary embodiments, it is not limited thereto. Rather, the appended claims should be construed broadly to include other variants and embodiments of the invention which may be made by those skilled in the art without departing from the scope and range of equivalents of the invention.

What is claimed is:

1. A two-part coupling assembly for re-connecting a first hollow body part to a second hollow body part and for emplacement by an instrument, the coupling assembly comprising:
   a first coupling part having a first outer circumference and first securement elements for deployment, by actuation of a first deployment mechanism of the instrument, to attach to the first body part, the first securement elements comprising first securement element cam surfaces adapted for engagement of corresponding first deployment mechanism cam surfaces disposed on the first deployment mechanism; and
   a second coupling part having a second outer circumference and second securement elements for deployment, by actuation of a second deployment mechanism of the instrument, to attach to the second body part, the second securement elements comprising second securement element cam surfaces adapted for engagement of corresponding second deployment mechanism cam surfaces disposed on the second deployment mechanism;
   wherein, prior to deployment of the first and second securement elements, the first and second securement elements are disposed radially within the first and second outer circumferences of the first and second coupling parts,
   wherein the first and second securement elements are deployed through engagement of the first and second securement element cam surfaces with the corresponding first and second deployment mechanism cam surfaces to deploy at least a portion of each of the first and second securement elements to a radial position outside of the first and second outer circumferences for respective engagement with the first and second hollow body parts, and
   wherein the first and second coupling parts having interconnecting elements for coupling together.

2. The two-part coupling assembly of claim 1, wherein the securenient elements of at least one of the first or second coupling parts are movably mounted to the first coupling part or the second coupling part.

3. The two-part coupling assembly of claim 1, wherein the securement elements are pivotally mounted to the first and second coupling parts and adapted to extend radially outward from the first and second coupling parts when deployed.

4. The two-part coupling assembly of claim 1, wherein the first and second coupling parts further comprise interconnecting elements adapted to secure the first coupling part to the second coupling part, wherein the interconnecting elements are selected from the group consisting of snap-fit connectors, detents, push-pin assemblies, threaded connectors, and releasably interlocking catch surfaces.

5. The two-part coupling assembly of claim 1, wherein the first coupling part comprises an upper ring defining a lumen, and the second coupling part comprises a lower ring defining a lumen that is generally coaxial with the lumen defined by the upper ring.

6. The two-part coupling assembly of claim 1, wherein the securement elements of at least one of the first or second coupling parts are flexibly mounted to said first or second coupling part.

7. The two-part coupling assembly of claim 1, wherein the two-part coupling assembly is formed from a biodegradable material.

8. An anastomosis device for joining a first vessel portion to a second vessel portion comprising:
   a first ring assembly defining a first internal passageway therethrough and adapted to engage the first vessel portion, the first ring comprising:
      a plurality of first securement elements being movable between a first position wherein the first securement elements are located within an outer circumference of the first ring and a second position and adapted to at least partially penetrate tissue of the first vessel portion in the second position; and
      at least one first connecting element;
   a second ring assembly defining a second internal passageway therethrough and adapted to engage the second vessel portion, the second ring comprising:
      a plurality of second securement elements being movable between a first position wherein the second securement elements are located within an outer circumference of the second ring and a second position and adapted to at least partially penetrate tissue of the second vessel portion in the second position; and
      at least one second connecting element adapted to engage the at least one first connecting element, wherein when the at least one first connecting element engages the at least one second connecting element, the first and second internal passageways are adjacent to each other to form a single anastomosis passageway extending through the first and second rings; and
   a deployer device having the first and second ring assemblies positioned at least partially on an exterior thereof for insertion into the first and second vessel portions;
   wherein, prior to deployment of the first and second securement elements, the first and second ring assemblies are axially spaced apart from each other, and
   wherein after deployment of at least one of the first and second securement elements, the first and second ring assemblies are drawn axially together towards each other until the first and second connecting elements engage each other.

9. The anastomosis device of claim 8, wherein the at least one first connecting element engages the at least one second connecting element, the first and second internal passageways are coaxial thereby forming a single anastomosis passageway extending through the first and second ring assemblies.

10. The anastomosis device of claim 8, wherein the first ring assembly has an outer circumference, and wherein, when the plurality of first securement elements are in the first position, the plurality of first securement elements are disposed radially inward of the outer circumference, and
   wherein when the plurality of first securement elements are in the second position, at least a portion of the plurality of first securement elements is disposed radially outward of the outer circumference.

11. The anastomosis device of claim 8, wherein the second ring assembly has an outer circumference, and wherein, when the plurality of second securement elements are in the first position, the plurality of second securement elements are disposed radially inward of the outer circumference, and
wherein when the plurality of second securement elements are in the second position, at least a portion of the plurality of second securement elements is disposed radially outward of the outer circumference.

12. The anastomosis device of claim 8, wherein the deployer device comprises proximal and distal ends and an elongated portion extending therebetween, wherein the deployer device includes a deployment mechanism located at the distal end thereof and operable to actuate each of the first and second securement elements from the first position to the second position.

13. The anastomosis device of claim 12, wherein the deployer device is further operable to: (i) actuate the first and second securement elements when the first and second ring assemblies are spaced apart from each other; and (ii) draw the first and second ring assemblies towards each other until the first connecting element mates with the second connecting element.

14. The anastomosis device of claim 8, wherein at least one of the first and second pluralities of securement elements is movably mounted to the respective first or second ring assembly.

15. The anastomosis device of claim 8, wherein the first and second ring assemblies are formed from a biodegradable material.

16. An anastomosis device for performing an anastomosis of two vessels comprising:
a first ring assembly means for engaging a first vessel, the first ring assembly means comprising a first connector element;
a second ring assembly means for engaging a second vessel, the second ring assembly means comprising a second connector element; and
an insertion device that inserts the first and second ring assembly means into the respective first and second vessels,
wherein the first and second ring assembly means are spaced apart during insertion into the respective first and second vessels and the first and second ring assembly means are drawn together after engagement of the first and second vessels;
wherein at least one of the first or second ring assembly means further comprises tissue engagement means for engaging the first or second vessel through penetration of the first or second vessel in an axial and radially outward direction from the respective first or second ring assembly means; and
wherein the first and second connector elements join the first and second ring assemblies.

17. The anastomosis device of claim 16, wherein the first and second ring assembly means each comprise tissue engagement means and the tissue engagement means of the first ring assembly means is positioned in an opposing direction to the tissue engagement means of the second ring assembly means.

18. A method of performing an anastomosis of two vessels comprising:
providing an anastomosis device comprising:
a first ring assembly having (i) at least one first securement element adapted to engage a first vessel and (ii) at least one first connecting element,
a second ring assembly having (i) at least one second securement element adapted to engage a second vessel and (ii) at least one second connecting element adapted to matingly engage the at least one first connecting element, and
an insertion device adapted to insert the first ring assembly and second ring assembly into the first and second vessels, wherein the first and second ring assemblies are releasably mounted on the insertion device;
inserting the insertion device into an area to be anastomosed, wherein the first ring assembly is inserted within the first vessel and the second ring assembly is inserted within the second vessel wherein the first and second ring assemblies are spaced apart by the insertion device;
actuating the at least one first securement element to engage the first vessel by positioning the first securement element to extend in a generally radially outward and axial direction from the first ring assembly, thereby securing the first ring assembly to the first vessel;
actuating the at least one second securement element to engage the second vessel by positioning the second securement element to extend in a generally radially outward and axial direction from the second ring assembly, thereby securing the second ring assembly to the second vessel;
after actuation of the first and second securement elements, drawing the first and second ring assemblies together until the at least one first connecting element mates with the at least one second connecting element;
releasing the insertion device from the first and second ring assemblies; and
withdrawing the insertion device from the area to be anastomosed.

19. The method of claim 18, wherein the step of actuating the first securement element further comprises the step of moving at least a portion of the first ring assembly in a first direction with respect to one of the insertion device or the second ring assembly in order to deploy the at least one first securement element.

20. The method of claim 18, wherein the step of actuating the second securement element further comprises further comprising the step of moving at least a portion of the second ring assembly in a second direction with respect to one of the insertion device or the first ring assembly in order to deploy the at least one second securement element.

21. The method of claim 18, wherein the first and second ring assemblies are constructed of biodegradable material.

* * * * *